(12) United States Patent
Movva et al.

(10) Patent No.: US 10,463,277 B2
(45) Date of Patent: Nov. 5, 2019

(54) METHODS AND SYSTEMS FOR LOCATING PATIENTS IN A FACILITY

(71) Applicant: CarePredict, Inc., Fort Lauderdale, FL (US)

(72) Inventors: Satish Movva, Davie, FL (US); Srinaag V. Samudrala, Hollywood, FL (US); Hassan Waqar Azeem Chaudhary, Coconut Creek, FL (US); Joshua David Paladeni, Plantation, FL (US); Gregory B. Zobel, Murrieta, CA (US)

(73) Assignee: CarePredict, Inc., Fort Lauderdale, FL (US)

( * ) Notice: Subject to any disclaimer, the term of this patent is extended or adjusted under 35 U.S.C. 154(b) by 11 days.

(21) Appl. No.: 15/891,107

(22) Filed: Feb. 7, 2018

(65) Prior Publication Data
US 2019/0239775 A1 Aug. 8, 2019

(51) Int. Cl.
G08B 1/08 (2006.01)
A61B 5/11 (2006.01)
(Continued)

(52) U.S. Cl.
CPC .......... A61B 5/1112 (2013.01); A61B 5/0004 (2013.01); A61B 5/0017 (2013.01);
(Continued)

(58) Field of Classification Search
CPC ....... A61B 5/1113; A61B 5/0024; H04W 4/02
See application file for complete search history.

(56) References Cited

U.S. PATENT DOCUMENTS 5,917,425 A 7/1999 Crimmins et al.
8,249,547 B1 8/2012 Fellner
(Continued)

FOREIGN PATENT DOCUMENTS

WO 2007/144419 12/2007
WO 2014/006543 A1 1/2014

OTHER PUBLICATIONS

Search Report from corresponding French Application No. 2,838,232 dated Feb. 26, 2016.
(Continued)

Primary Examiner — Hongmin Fan
(74) Attorney, Agent, or Firm — DLA Piper LLP (US)

(57) ABSTRACT

Embodiments of the present disclosure relate to systems and methods of locating a patent within a facility. In one example, the system includes a beacon and a sensor. The beacon is positioned in a location of the facility. The beacon includes an infrared emitter and a processor. The processor is in communication with the infrared emitter. The processor is configured to instruct the infrared emitter to periodically emit an infrared emission. The processor modulates the infrared emission with a unique identification of the beacon that corresponds to the location of the beacon. The sensor is worn by the sensor wearer. The sensor includes an infrared receiver and a processor. The processor is in communication with the infrared received. The infrared receiver is configured to demodulate the received infrared emission to identify the unique identification of the beacon.

20 Claims, 31 Drawing Sheets

(51) Int. Cl.
*A61B 5/00* (2006.01)
*A61B 5/0205* (2006.01)

(52) U.S. Cl.
CPC .......... *A61B 5/0022* (2013.01); *A61B 5/1116* (2013.01); *A61B 5/0205* (2013.01); *A61B 5/1113* (2013.01); *A61B 5/1118* (2013.01); *A61B 2562/0219* (2013.01)

(56) References Cited

U.S. PATENT DOCUMENTS

| | | |
|---|---|---|
| 2006/0047538 A1 | 3/2006 | Condurso et al. |
| 2009/0278696 A1 | 11/2009 | Lindh et al. |
| 2009/0284367 A1 | 11/2009 | Pfafman et al. |
| 2012/0256742 A1 | 10/2012 | Snodgrass et al. |
| 2013/0085780 A1 | 4/2013 | Braunstein et al. |
| 2013/0095459 A1 | 4/2013 | Tran |
| 2013/0135097 A1 | 5/2013 | Doezema |
| 2016/0029160 A1* | 1/2016 | Theurer ................ H04W 4/02 455/456.1 |
| 2016/0260296 A1* | 9/2016 | Shirriff .................. G08B 5/22 |
| 2017/0171719 A1* | 6/2017 | Igarashi ................ H04W 4/043 |
| 2017/0171754 A1* | 6/2017 | South .................... H04W 4/90 |
| 2017/0222980 A1* | 8/2017 | Revashetti ............ H04L 63/04 |
| 2017/0289760 A1 | 10/2017 | Sainfort et al. |
| 2018/0356520 A1* | 12/2018 | Booij ..................... G01S 15/66 |

OTHER PUBLICATIONS

Office Action from corresponding U.S. Appl. No. 13/896,306 dated Aug. 28, 2015.

Office Action from corresponding U.S. Appl. No. 13/896,306 dated Feb. 13, 2015.

Office Action from corresponding U.S. Appl. No. 13/896,306, dated Mar. 10, 2016.

Office Action from corresponding U.S. Appl. No. 14/674,813, dated Feb. 1, 2016.

International Search Report and Written Opinion from corresponding International Application No. PCT/US2018/017241, dated Jul. 12, 2018.

* cited by examiner

METHODS AND SYSTEMS FOR LOCATING PATIENTS IN A FACILITY

TECHNICAL FIELD

The exemplary teachings herein pertain to methods and systems for determining levels of healthcare interventions, and in particular, to methods and systems which monitor a patients activity and location to determine if healthcare interventions are warranted, and what level of healthcare interventions are deemed necessary or required. Specifically, the present disclosure relates to methods and systems which keeps patients in the lowest cost setting of care, the home, for as long as possible, through the use of wearable sensor technology to determine when a patient's health may be degrading to trigger progressively higher levels of care and involvement, from "free" hands and eyes to skilled clinicians.

BACKGROUND

The Baby Boomer wave is yet to peak and already they are electing Medicare at the rate of 11,000 a day since June, 2012. Patients with chronic care conditions are on the rise, especially those with the so-called "life style" diseases such as Diabetes and Obesity. The funding model of our healthcare system cannot keep pace with the demand. As in any system, higher level of resources cost more. The highest cost care setting is the Hospital, and the lowest is care at home. Further, the staffing model of our healthcare system cannot keep pace with the demand. The ratio between available professional caregivers and seniors with healthcare needs is set to dramatically escalate as the baby boomer wave rolls inexorably towards its peak in 2023. The advantages of a low cost care setting can be wiped out in an instant, if the patient health degrades unnoticed and they end up in the ER or an Acute care setting.

The Patient Protection and Affordable Care Act (ACA) enshrines and encourages the concept of Accountable Care Organizations (ACO). According to the ACA, an ACO "must define processes to promote evidence-based medicine and patient engagement, report on quality and cost measures, and coordinate care, such as through the use of tele-health, remote patient monitoring, and other such enabling technologies." In essence this means that healthcare providers are responsible for the outcomes of a patient even when the patient is not in their setting of care. For instance an ACO is still accountable when a patient is discharged to an Assisted Living Facility (ALF) or to home care to make certain the patient outcome remains positive, i.e., the ACO's are responsible for the patient outcome even when they are at home or in an ALF setting. This is ensured by the use of financial incentives to the ACO that maintains good patient outcomes. The ACA caused a large number of ACO's to form quickly and they usually consist of a hospital, physicians and increasingly post acute healthcare providers such as Home care or ALF.

The second aspect of the Affordable Care Act is the incentive to set up Health exchanges in which Insurance companies compete to provide healthcare policies. Since pre-existing conditions and cherry picking of the insured are not allowed, this will cause these insurance companies, typically operating as Managed Care Organizations (MCO) to offer attractive benefits to obtain customers but will also force them to use cost containment models to make the care delivery very efficient.

The third aspect of the ACA is that state Medicaid enrolments are set to increase dramatically. Even before ACA, states such as Texas, New Jersey and others were experimenting with outsourcing their entire Medicaid populations to Managed Care entities primarily with a cost containment by utilization management goal. Medicaid populations have a high incidence of lifestyle diseases as well and a tendency to utilize high cost healthcare such as the Emergency Room. This Medicaid expansion brings into the main stream more patients who are homebound and/or have one or more chronic diseases, who were previously completely outside the healthcare system (due to lack of insurance), and whose healthcare system contact was primarily the ER, and who now will fall under the MCO umbrella. This additional patient load can be a very high utilizer of costly services.

Further, hospitals that participate in Medicare are now responsible for the patient's outcome even after discharge; in essence, if the patient is re-hospitalized within 30 days following discharge, for the same diagnosis that they were originally in the hospital for, then the hospital has to absorb all the costs for the patient's subsequent admission. In addition there is potential for extending this warranty period from 30 days to 60 days and beyond. This financial penalty makes the hospital acutely concerned for the patients' welfare post discharge and incentivizes the Hospital to offer services outside their four walls, out of their own pocket, to make sure the patient is not readmitted unnecessarily. These services today range from having a home care agency check on the patient periodically in the 30 days and/or to assign a tele-monitor to remotely collect clinical data on the patient to try to see if a hospitalization is needed.

The use of Tele-Monitoring has been well documented for several decades. Tele-monitoring as used today is primarily a device installed in the home with various sensors such as Blood Pressure cuffs, pulse-oximetry and weight scales that are designed to collect clinical "Vitals" of the patient. These devices require the patient to be an active participant in the process and diligently use the device at prescribed times to collect the data. The device then transmits the data to a central clearing house or to a Live Ops center for action.

Tele-monitoring has been used extensively in the past to monitor "Clinical Vitals" such as pulse, blood oxygen levels, ECG, EEG etc. Tele-monitoring is usually not a wearable device but a static device in a home with various attachments that a patient needs to actively use at prescribed times by applying its various measuring devices to their body (ECG leads, pulse oximetry sensor, BP cuffs etc.). Tele-monitoring usually sends data to a LiveOps center where a nurse monitors readings and calls a patient back for abnormal vitals results. There is no inclusion of "free" resources such as resident caregivers, family and friends, to help determine the patient state. There is no tracking of functional state or detecting anomalies in patterns of activity.

The adoption of Tele-monitoring has not taken off primarily due to the high cost of these proprietary devices and lack of reimbursement from the payers for installing them in a patient home. An additional hurdle has been the requirement for active participation by the patient in using the devices.

In the early 2000's with the widespread availability of RFID, several large companies (Intel, GE among others) tried to deploy the model of a fully instrumented patient home with the use of ambient monitoring. This ranged from sensors in the carpet to measure weight, to pressure mats that detect steps, to cameras that detect presence of the patient and attempt to deduce the activity they were involved in.

This overly ambitious idea failed due to several reasons: one being the very high cost of retrofitting a home for ambient monitoring systems (sensor laden carpets, door mats, cameras, wiring, RFID tags on everyday objects and RFID readers), and a second being patient disenchantment with the surveillance systems that reeked of "big brother" style lack of privacy.

Ambient monitoring came into vogue with the widespread use of RFID in 2000. Ambient monitoring uses cameras, pressure mats, carpet sensors and RFID tags on household items to try to detect activity that a patient is engaged in. It is very expensive to fit a home with ambient monitoring. Mostly targeted towards group Senior Living Facilities, it is highly intrusive and the lack of privacy means low adoption rates. Also, ambient monitoring has trouble distinguishing the patient from other residents. Wearable sensors bypass the need for ambient monitoring as the patient is instrumented and not the home.

Wearable Sensors utilizing MEMS (Micro Electro Mechanical Systems) are ubiquitous now in personal health and fitness (e.g., fitbit, Jawbone, Nike etc.). Sensors typically have Accelerometers, Gyros, Inclinometers and Magnetometers among other MEMS. Sensors can detect walking, running, sleeping, sitting, falling, and rolling among other functional states of a wearer by combining the readings from the multiple on-board MEMS. Sensors can have radios to communicate with a base station, smartphone, computing device or directly to the internet.

Over the last 3-5 years and especially the last 12 months, there has been a sharp increase in the number of health and fitness devices targeting consumers directly. These range from wearable sensors for counting steps, sleep state, and other fitness metrics to disease monitoring by use of clinical FDA approved consumer devices such as blood pressure monitors, weight scales, BMI and heart rate monitors. One common aspect of these devices is that they all interact with a consumer's Tablet, Smartphone or other computing device and present information graphically to the consumer. Some also allow the data to be uploaded to a web site and either printed and shared with a clinician, or in a few cases to be sent to a Clinician's email, or in rare cases to be sent electronically to the system the Clinician uses to store that patient's records. In almost all cases, these readings sit unattended until the clinician and patient have another reason to interact, such as a scheduled appointment. This is because the U.S. health care system is still based on a patient encounter between a Clinician and Patient to trigger any kind of interaction with the patient measurements.

Unlike the methods and systems of the present disclosure, other than recent use in fall detection, wearable MEMS sensors have not been used previously in a home setting with patients. Sensors have not been used as near real-time feedback sources in remote monitoring of directed demonstration of activity that is disease specific. Wearable sensors have not been used previously in a home setting with patients to track activity and track which room/area of a home the activity occurs in to deduce type of activity.

Further, unlike the methods and systems of the present disclosure, systems have not previously been used in conjunction with remote sensors to predict disease progression or decline in functional status of a patient in a home setting. Systems have not been used previously to ask disease specific questions in an automated manner (previously this required a clinical actor to present questions, observe patient and record answers). Automated systems have not been used previously to ask resident care givers, family members and friends of a patient to actively participate in the observation and interrogation of a patient with disease specific questions. Also, automated systems have not been used to triage through all available "free" resources before progressively costly resources are utilized.

Accordingly, to address the above stated issues, a method and system for remotely determining the need for healthcare interventions, and which keeps patients in the lowest cost setting of care, the home, for as long as possible is needed. The methods and systems disclosed herein fulfill such needs, and the costs and disadvantages associated with prior attempts at tele-monitoring, ambient monitoring and/or consumer self-monitoring are diminished or eliminated. It is desired that the disclosed methods and systems for providing the above benefits be applicable to any instances or applications wherein a patient's health is monitored to determine healthcare interventions.

SUMMARY

The exemplary technique(s), system(s) and method(s) presented herein relate to methods and systems for remotely determining levels of healthcare interventions, comprising wearable sensor technology in association with a computerized system utilizing a set of software and databases operating on a set of physical hardware in a remote location. The system monitors a patients activity and location, and determines when a patient who may have one or more chronic diseases or is otherwise homebound, requires progressively higher levels of care from family member interventions to a nurse phone call, to a medication change, to a nurse visit, to a physician visits and to a hospital visit.

Most patients have varying circles of care surrounding them from, a resident spouse or other family caregiver, to non-resident family members or friends to nurses from home care agencies to physicians and finally hospitals. However, the first two circles of care, resident family caregiver and family members/friends, are not actively involved in the chain of care today. They are passive bystanders for the most part even though they are the most readily available, have a vested interest and are in effect "free" hands and eyes in the care of the patient. By using sensors to detect change in a patient's functional state or to detect changes in patterns of activities of daily living of the patient, the disclosed methods and systems co-opt the available family caregivers or family members to act as eyes and ears to observe and report the state of the patient and to interrogate and report answers from the patient based on clinically established and disease specific questions generated by the disclosed methods and systems, as well as general questions to establish that the state of the patient is congruent with the system determination. This is the lowest cost steady state both in funding and staffing for patients who are either elderly or have a history of hospitalization or have one or more chronic care conditions.

The data from the sensors in conjunction with data observed/reported by members of the immediate circles of care is used to determine the likelihood that a patient may need a higher cost clinical intervention such as a nurse phone call to the patient, a nurse visit to the patient, a physician appointment or communication to a physician to change meds, or ultimately hospitalization.

This conservative and progressive escalation to higher levels of care is attractive to both the ACQ and MCO customers as they struggle to manage outcomes (and thus reimbursement) as well as manage scarce resources in human staff. Both ACOs and MCOs prefer a low cost steady state to a high cost asymptotic event such as a hospital admission being the first inkling that a member patient health had deteriorated. Further, this model wherein family resources are being activated by the System first promotes a caring social network around a patient that could foster a better quality of life. Previously, family members and friends were only aware post an adverse event and could not help prior to that, as they were more likely not aware of the gradual decline that the System is now able to detect and warn.

Accordingly, it is an object of the methods and systems disclosed herein to function as an early warning system to all persons involved with a patient, including the ACO/MCO, that a patient degradation is underway and to help trigger proportionately increasing levels of interventions to return the patient to positive outcomes.

It is another object of the methods and systems disclosed herein to utilize the lowest cost resources, for instance technology and "free" eyes and ears in terms of resident caregivers or non-resident family members and friends, in its capacity as a sentinel or early warning system that only progressively escalates to higher cost interventions.

It is another object of the methods and systems disclosed herein to utilize passive monitoring of functional state and detection of activity patterns and deviations as an indicator of health state, and to co-opt the caregivers around a patient into being the remote "eyes and ears" in collecting additional data and validating the determination for care.

It is another object of the methods and systems disclosed herein to utilize an unobtrusive sensor that is worn on the body and which integrates room/area identification, to allow the system to deduce activity the patient maybe involved in without encroaching on their privacy.

It is another object of the methods and systems disclosed herein to use the readings from the wearable sensor to drive immediate automated analysis and activate the different levels of care surrounding a patient to get additional information, to confirm predicted trends, and ultimately be an early warning system that raises an alert to a Clinician before the patient deteriorates too far to be managed cost effectively.

It is another object of the methods and systems disclosed herein to utilize a sentinel system in conjunction with patient education on wellness and management of their disease through healthier life styles.

In one embodiment, a system for locating an individual within a space is disclosed herein. The system includes a beacon and a sensor. The beacon is positioned in a location of the space. The beacon includes an infrared emitter and a processor. The processor is in communication with the infrared emitter. The processor is configured to instruct the infrared emitter to periodically emit an infrared emission. The processor modulates the infrared emission with a unique identification of the beacon that corresponds to the location of the beacon. The sensor is worn by the sensor wearer. The sensor includes an infrared receiver and a processor. The processor is in communication with the infrared received. The infrared receiver is configured to demodulate the received infrared emission to identify the unique identification of the beacon.

In another embodiment, a method of determining a location of a sensor wearer within a space is disclosed herein. A sensor, positioned on the sensor wearer, receives an infrared emission emitted by a beacon proximate the sensor wearer. The infrared emission is modulated to comprise a unique identification of the infrared sensor. The sensor demodulates the infrared emission to extract the unique identification of the infrared sensor. The sensor determines whether the beacon that emitted the infrared emission is in a list of recent locations. The sensor reports to a remote management entity, the location of the sensor wearer and current time based on information received in the infrared emission, responsive to determining that the beacon is not in the list of recent locations.

In another embodiment, a method of determining a location of a sensor wearer within a space is disclosed herein. A sensor, positioned on the sensor wearer, receives an infrared emission emitted by a beacon proximate the sensor wearer. The infrared emission is modulated to comprise a unique identification of the beacon. The sensor determines a current location of the sensor wearer based on a unique identification of the beacon, by demodulating the infrared emission to extract the unique identification of the beacon. The sensor determines whether the unique identification of the beacon corresponds to a pre-boundary location. Responsive to determining that the unique identification of the beacon corresponds to a pre-boundary beacon, the sensor records the infrared emission.

In another embodiment, a system for locating an individual within a space is disclosed herein. The system includes a beacon, a sensor, a communication hub, and a management entity. The beacon is positioned in a location of the space. The beacon includes an infrared emitter and a processor. The processor is in communication with the infrared emitter. The processor is configured to instruct the infrared emitter to periodically emit an infrared emission. The processor modulates the infrared emission with a unique identification of the beacon that corresponds to the location of the beacon. The sensor is worn by the sensor wearer. The sensor includes an infrared receiver and a processor in communication with the infrared received. The infrared receiver is configured to demodulate the received infrared emission to identify the unique identification of the beacon. The communication hub is positioned within the space. The communication hub is in wireless communication with the sensor. The management entity is in communication with the communication hub, such that the communication hub provides a gateway between the management entity and the communication hub.

In another embodiment, a method of providing assistance to a sensor wearer in a space is disclosed herein. A processor receives a problem scenario message from a sensor of the sensor wearer. The processor generates a message for delivery to a plurality of users via a plurality of client devices of the plurality of users. The processor determines that a user of the plurality of users has accepted the assistance request via a client device of the plurality of client devices. The processor determines a current location of the sensor wearer based on previously received location reports. The processor generates a graphical representation of the space and the current location of the sensor wearer in the space. The processor prompts the user to deliver assistance to the sensor wearer by delivering the graphical representation to the client device.

Additional objects, advantages and novel features will be set forth in part in the description which follows, and in part will become apparent to those skilled in the art upon examination of the following and the accompanying drawings or may be learned by production or operation of the examples.

BRIEF DESCRIPTION OF THE DRAWINGS

The drawing figures depict one or more implementations in accord with the present teachings, by way of example only, not by way of limitation. In the drawing figures, like reference numerals refer to the same or similar elements.

DETAILED DESCRIPTION

The following description refers to numerous specific details which are set forth by way of examples to provide a thorough understanding of the relevant method(s) and system(s). It should be apparent to those skilled in the art that the present disclosure may be practiced without such details. In other instances, well known methods, procedures, components, and circuitry have been described at a relatively high-level, without detail, in order to avoid unnecessarily obscuring aspects of the present disclosure. While the description refers by way of example to methods and systems for determining healthcare interventions, it should be understood that the method(s) and system(s) described herein may be used in any situation where a patient's health is monitored. Exemplary methods and systems may found in U.S. patent application Ser. No. 15/703,507, filed Sep. 13, 2017, and U.S. patent application Ser. No. 13/896,306, filed May 16, 2013, which are hereby incorporated by reference in their entireties.

As discussed in more detail below, the system comprises a wearable sensor, a plurality of infrared beacons, and a communication system in association with a computerized system utilizing a set of software and databases operating on a set of physical hardware in a remote location. The system utilizes passive monitoring of the functional state of a patient, and detection of activity patterns of a patient, and deviations thereof, to determine the health state of a patient. The system utilizes this health state determination to co-opt the various levels of caregivers around a patient to collect additional data and validate the determination for care.

The system is configured for the patient with a set of data. For example, including but not limited to, diseases present, patient address, contact info, availability and types of computing device for use by patient, availability and number of telephone for use by patient, family caregiver contact info and computing device info, family members contact info and computing device info, ACO affiliation, MCO affiliation, Hospital affiliation, Physicians of record, Case manager of record, Geriatric counselor of record, Pharmacies and contact info, Insurance info, type of residence, number of rooms, type of each room, base station type, communication medium and its configuration, number of beacons, type of beacons.

The home the patient lives in maybe equipped with low power infrared beacons ("Beacon") which transmit a unique ID representing the area of a home they are affixed in. For example Stove/Kitchen, Toilet/Bathroom etc. These are self installed devices that are fixed at a range of prescribed heights and operate on self contained power or utility power.

Figure 1:
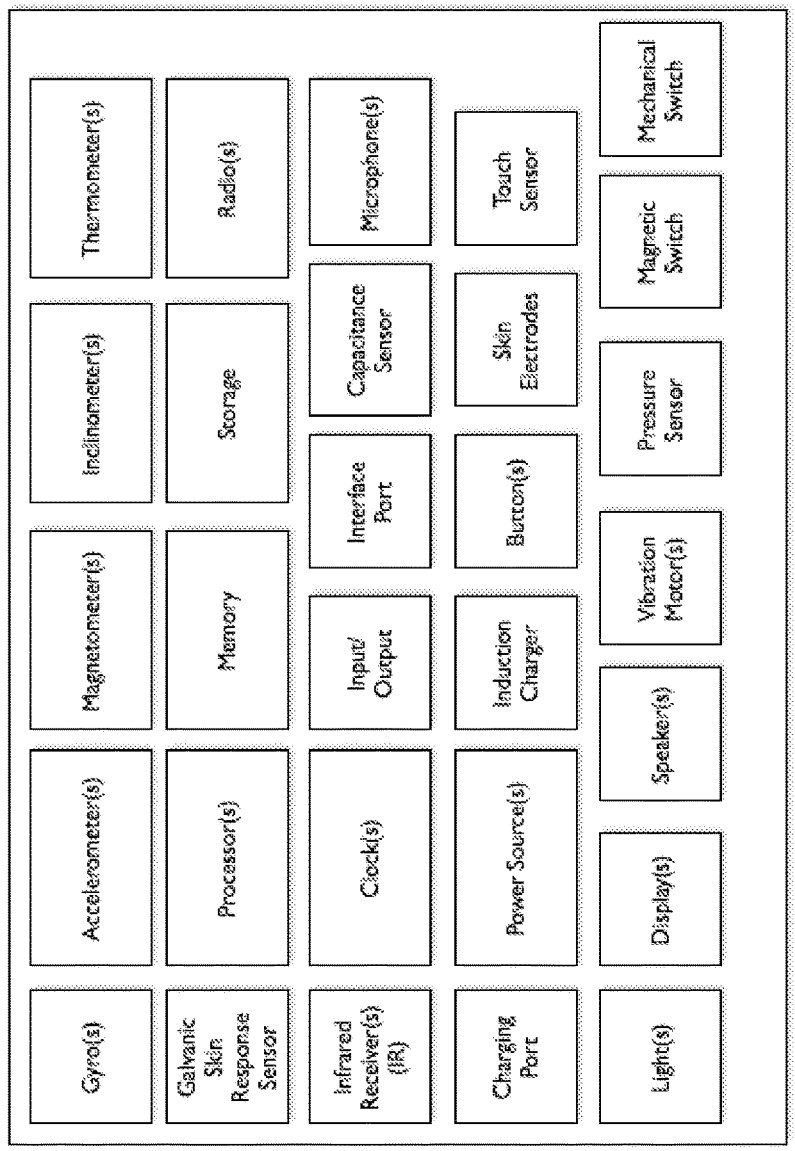
FIG. 1 is a block diagram of the components of the sensor of an exemplary embodiment of the system of the present disclosure.

The patient wears a wearable sensor apparatus, which is worn on the body. The placement of the Sensor may range from head, neck, chest, waist, upper hand, forearm, the wrist, hand, upper or lower thigh or lower extremities and the ideal placement may be recommended based on the disease state and physical ability and condition of the Patient. The Sensor may be worn under certain types of clothing as well that allows infrared beams to pass through. The Sensor may have one or more adjustable band, bracelet, strap, lanyards to allow it to be worn. The Sensor may be constructed to be liquid proof or liquid resistant FIG. 1 is a block diagram of the components of the sensor of an exemplary embodiment of the system of the present disclosure. As can be seen in FIG. 1, the Sensor contains various sensing devices such as, one or more Gyros, Accelerometers, Magnetometers, Inclinometers, Thermometers, and/or Galvanic Skin Response (GSR) sensors to detect the motion and state of the person and direction of travel/orientation of person wearing it. The Sensor also includes one or more Infrared receivers, or other suitable types of receivers, capable of sensing external infrared beams, or other suitable types of transmissions, and decoding the data embedded therein. The infrared receivers contained in the Sensor are capable of discriminating among multiple infrared beams and deducing the strength of the beam and thus the distance to the beam transmitter. One or more of the infrared receivers may be arranged on the Sensor to assist in beam triangulation to increase accuracy in determining direction, strength and distance to the beam transmitters.

Additionally, the Sensor contains a processing unit, memory and storage as required for a computing device. The Sensor runs operating system software and application software that allows the Sensor to be programmed to perform actions based on events. The Sensor may contain one or more radios such as a WiFi radio, a Bluetooth radio, a cellular data modem radio, a Zigbee radio, a XBee radio, a LoRa radio, an ANT radio, a THREAD radio, a software defined radio supporting multiple waveforms including custom waveforms & protocols. The Sensor may contain one or more interface ports for the Sensor to be programmed, tested, charged or for data to be communicated into or out of the Sensor. The Sensor contains one or more fixed or removable power sources to operate independently of external power. The Sensor may contain one or more charging ports to charge the internal power source. The Sensor may contain one or more induction charging circuits for the internal power source to be charged using a charging surface such as a charging mat, charging dongle, and/or charging cradle. The Sensor may contain one or more indicators to inform the user visually or aurally of the state of the charge within the internal power source.

The Sensor may also contain one or more output devices to convey information such as lights, vibration motors, display units, and/or speakers. The Sensor may contain one or more input devices to interact with the user such as microphones, buttons, and touch sensors. The Sensor may also employ its internal sensing devices to interact such as for example single tap on the device to display visually or aurally the battery level or double tap to cause it to synchronize data outside its normal schedule.

Still further, the Sensor may employ various sensing devices such as one or more capacitance sensors, skin electrodes, pressure sensors, magnetic switches and/or mechanical switches, to assist in detecting when it is being worn. The Sensor can record and report when it is not being worn and can report data related to how often it is being worn and how often it is not. The Sensor can make deductions on the activity and posture of the patient (e.g., sleeping, sitting, reclining, prone, supine, walking, running, shuffling, and/or falling). The Sensor can determine which local area (room) of a structure (home) or a specific area (Toilet) within a local area (Bathroom) of a structure (home) the patient is proximal to by means of an infrared receiver receiving the signals from the Beacon and deducing the location by the IDs of the one or more beacons visible to the infrared receiver(s).

The Sensor can determine which activity the patient is engaged in by the combination of the functional activity type (e.g., walking, sitting, reclining, standing, and/or lying down) and the area/room they are in when performing such activity. For instance, when the room detected is a bathroom and posture detected is sitting, this may indicate with a high likelihood that the person is using the toilet.

The Sensor may contain one or more internal clocks to provide time base and time reference. The Sensor aggregates data from its sensing devices and time stamps all data. The Sensor deduces activity of the patient based on the aggregation of the data from its sensing devices. The Sensor is capable of storing onboard, information deduced from the sensing devices readings and worn status.

The Sensor periodically checks to see if a connection is available to the internet either via a Base Station (if one is configured), or through a smart phone (if one is configured), a WiFi network (if one is configured), an onboard or outboard cellular data modem (if one is configured or is present onboard). If a base station is configured, the Sensor may communicate to it using a low power short range radio frequency protocol such as Bluetooth, Zigbee, XBee or WiFi. If a smartphone is configured, the Sensor may communicate to it using a low power short range radio frequency protocol such as Bluetooth, NFC, or WiFi. If an outboard cellular data modem is configured, the Sensor may communicate to it using a low power short range radio frequency protocol such as Bluetooth, NFC, or WiFi. If an onboard cellular data modem is configured, the Sensor may communicate to it using internal bus protocols such as I2C, NXP, SDIO, SPI, UART/USART or other internal intra-component, intra circuit board or inter component and inter circuit board protocols. The Sensor periodically communicates via the Internet and uploads data into one or more databases and software systems ("System") at a remote location.

It is foreseen that the sensor and or system can be integrated with or to various other sensors such as Blood Pressure cuffs, pulse-oximetry, weight scales, sensors for counting steps, sleep state, and other fitness metrics, blood pressure monitors, BMI and/or heart rate monitors. The system can consume the readings from one or more of these devices to add data points to its prediction analysis.

Figure 2:
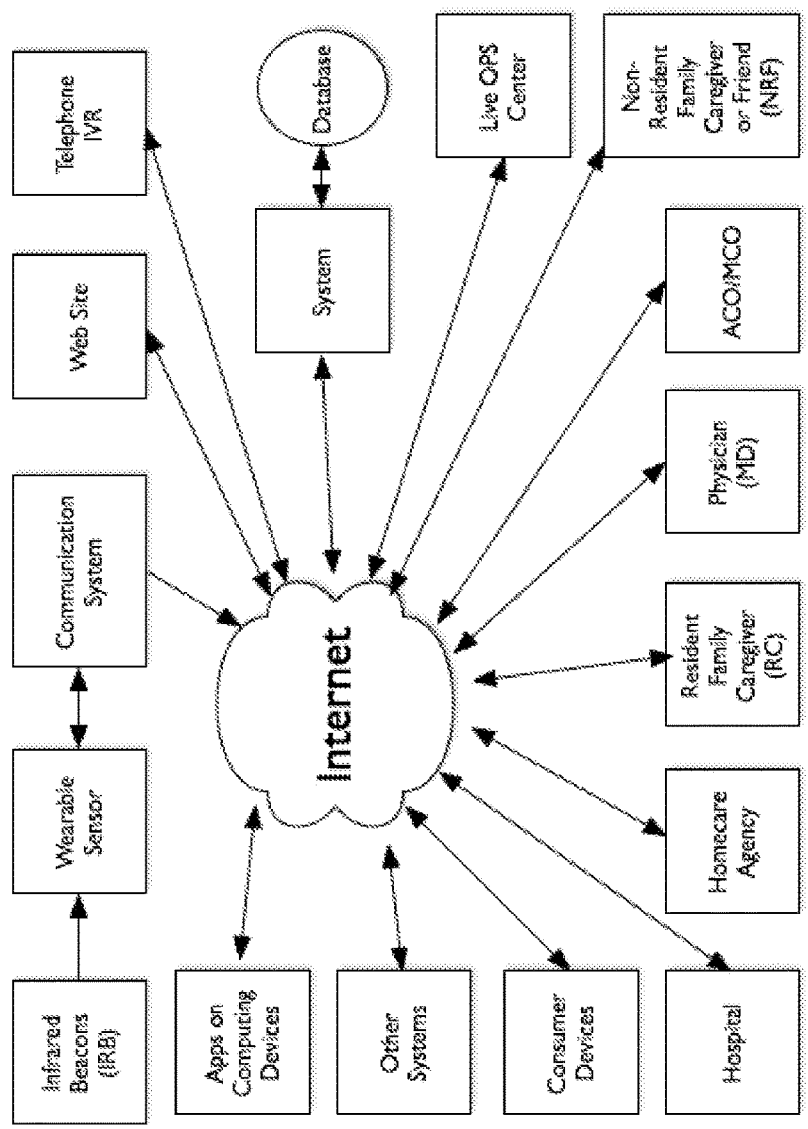
FIG. 2 is a block diagram of an exemplary embodiment of the system of the present disclosure.

FIG. 2 is a block diagram of an exemplary embodiment of the system of the present disclosure. The System is comprised of a set of software and databases operating on a set of physical hardware in a remote location. The System can send and receive data through the Internet to Sensors, Base Stations, other Devices such as but not limited to patient self-monitoring devices, other Systems, Computing devices, web sites, and Smartphones. The System can be accessed by various persons via the Internet using a web browser, and System presents information relevant to the person viewing it. The System can send and receive data to and from one or more Sensors worn by one or more Patients. The System can send and receive data to and from Software Applications running on computing devices such as but not limited to Smart Phones, Tablets and Computers. The System stores the received data into one or more databases. The System can communicate with multiple other Systems, Devices and Communications networks.

The System actively monitors usage data sent by the Sensor (being worn or not), and can initiate notifications in a progressively escalating manner if the device is not being used as intended. The System creates a baseline for activity using the first n days of received data, where n is configurable. The received data may originate from, but is not limited to, the Sensor, Other Systems, Consumer Devices, responses to questions on configured computing devices of resident family caregiver, non-resident family members, patient, Telephone IVR, clinicians, live ops center, physician, hospital and/or diagnostic labs.

The System analyzes the data and applies various algorithms based on but not limited to: a) one or more diseases of the person (e.g., CHF, Diabetes, Hypertension COPD, etc.); b) deduce functional level by how much activity the patient is engaged in; c) analyze for changes in activity pattern from previously learned patterns of activity; d) deduce from the data such as change in gait, number of steps taken, amount of activity, etc., if the person is degrading; e) deduce if the person has fallen by applying an algorithm to the sensor accelerometer data, room/area the person is in, position of the person now (e.g., supine, prone, reclining, etc.), and length of time with limited motion, repeated motions to achieve a standing position, crawling motions, and if body position is appropriate normally for the room/area person is now in.

The System sends a notification to the patient's configured computing device (Tablet/Phone/Computer) if one is configured. The notification will cause the application on the computing device to present specific questions. These questions will be based on the disease state of the patient and are well established in the academia as to their predictive value. The questions may have an interrogatory component where the app poses questions to the patient and accepts their responses. The system gathers the responses from the local application and adds them to its database(s). The software then analyses the additional data to see if escalation to next level, status quo, or de-escalation is appropriate. If the patient does not answer or respond to the application prompts, the System may escalate to the next level of care.

Based upon the sensed information, the System can additionally ask the patient to demonstrate a disease specific activity such as "walk twenty steps," and use the sensor to detect demonstration of the activity, time taken to complete activity, and/or vital signs before, during and after the activity, etc., and at its completion ask follow-up questions based upon the sensed information, such as "are you short of breath," etc. The system stores the responses for analysis and scoring according to established clinical guidelines. Thus, the system, based upon its analysis of sensed information, can automatically initiate patient tasks or tests, physical and/or mental, and evaluate patient performance of these tasks or tests in real-time.

If the patient is not capable of using a computing device, the System is configured to cause a telephone IVR system to call the patient. The Telephone IVR system will ask questions of the Patient such as for example "Press 1 if you are feeling pain", "Press 2 if you took your meds today", "Press 3 if you had a bowel movement", "Press 4 if you are feeling short of breath", and/or "Press 5 if your ankles are swollen". These questions will be based on the disease state of the patient and are well established in the academia as to their predictive value. The System gathers the responses from the IVR system and adds them to the database(s). The System then analyzes the additional data to see if escalation to next level, status quo, or de-escalation is appropriate.

The software, depending on the analysis of sensed information and/or responses to questions, sends a notification to the configured computing device of a resident caregiver who is in the same home as the Patient, (First level of the "Circles of Care"). The notification will cause the application on the computing device to present specific questions. These questions will be based on the disease state of the patient and are well established in the academia as to their predictive value. The questions will have an observational component where the resident caregiver answers questions on the observed state and behavior of the patient. The other questions will have an interrogatory component where the resident caregiver poses questions to the patient and enters their responses. The System gathers the responses and adds them to the database(s). The System then analyzes the additional data to see if escalation to next level, status quo, or de-escalation is appropriate.

The software, depending on the analysis of sensed information and/or responses to questions, sends a notification to the configured computing device of the next level of non-resident family members (siblings, sons/daughters, etc., who may not be residing in the same vicinity as patient) and/or friends, (Second level of the "Circles of Care"). The notification will cause the application on the computing device to present specific questions. These questions will be based on the disease state of the patient and are well established in the academia as to their predictive value. If the family member or friend is physically in the same vicinity as the patient (the application provides the choice on whether they are physically with the patient) then the questions will have an observational component where the family member or friend answers questions on the observed state and behavior of the patient. The other questions will have an interrogatory component where the family member or friend poses questions to the patient, and enters their responses. The System gathers the responses and adds them to the database(s). The System then analyzes the additional data to see if escalation to next level, status quo, or de-escalation is appropriate.

If escalation is required based on all the data gathered thus far, the software sends a notification to the configured computing device(s) at a Live Ops center or other computing device where trained nurses or other clinical contacts review the data, call the Patient and/or resident family caregiver and/or other family members or friends. (Third level of the "Circles of Care"). The notification may cause the Nurse to call the patient with specific clinical questions based on their diseases, functional status, observed and reported state. The notification may cause the Nurse to call the resident caregiver with specific questions based on the patient diseases, functional status, observed and reported state. The notification may cause the Nurse to call the non-resident family member or friend with specific questions based on the patient diseases, functional status, observed and reported state. The system gathers the responses and adds them to the database. The Nurse is then offered a choice to escalate to next level, maintain status quo, or de-escalate to a lower level.

If escalation is chosen, the Nurse can escalate to the next necessary or desired step(s), which may be an in person visit, consult with physician to change medication, schedule a physician appointment for the patient, or arrange for hospitalization. (Fourth level of the "Circles of Care"). All stakeholders in the 1st-3rd levels of the "Circles of Care" are notified of escalation. If Status Quo is chosen, all stakeholders in the 1st-3rd levels of the "Circles of Care" are notified of status quo and optionally additional instructions on what changes in patient state to look for. A follow-up (notification) to 1st-3rd levels is scheduled by the system to ask follow-up questions identified by the nurse. If de-escalation is chosen, all stakeholders in the 1st-3rd levels of the "Circles of Care" are notified of de-escalation and optionally additional instructions on what changes in patient state to look for.

Figure 3:
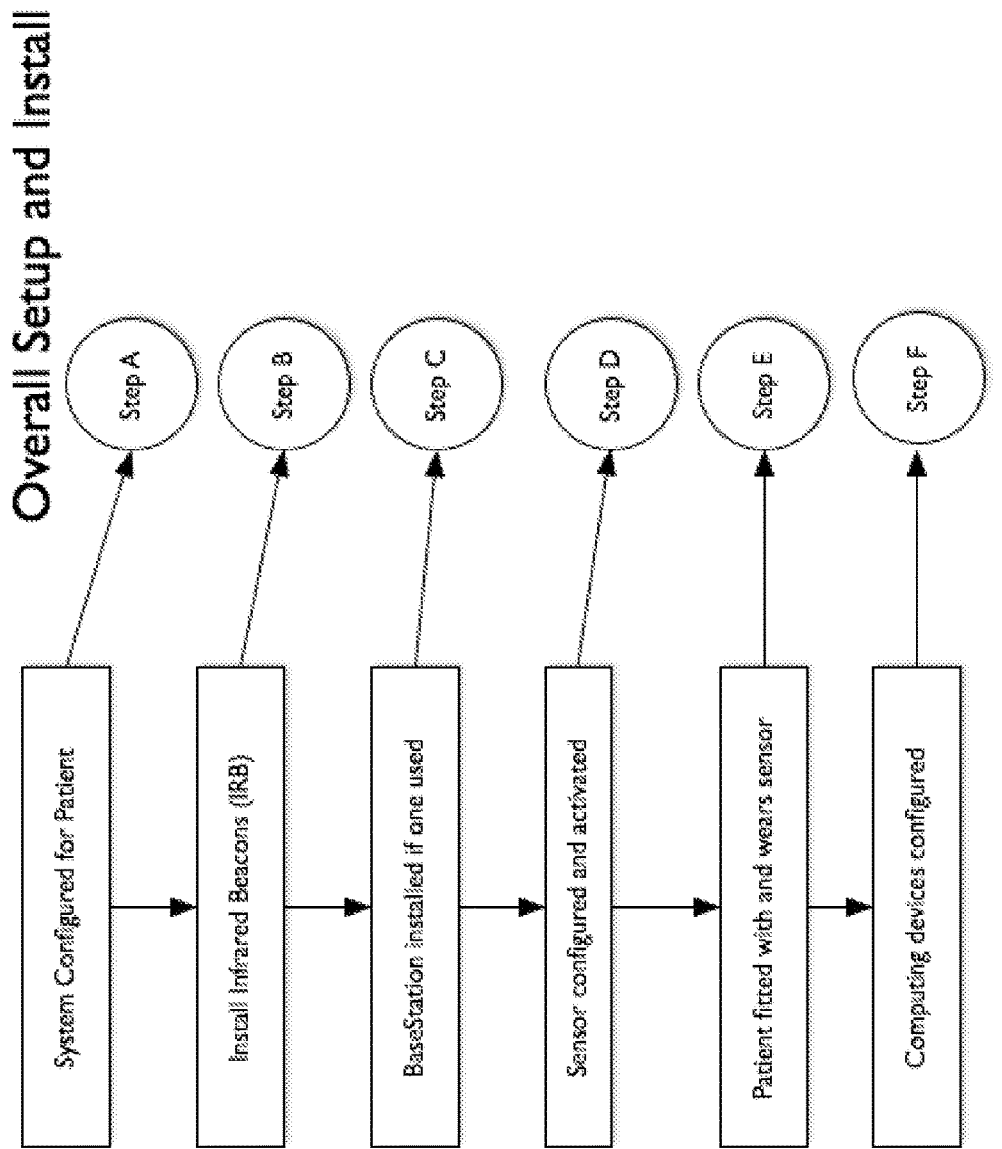
FIG. 3 is a flow chart of the overall setup and installation of an exemplary embodiment of the method and system of the present disclosure.
Figure 4A:
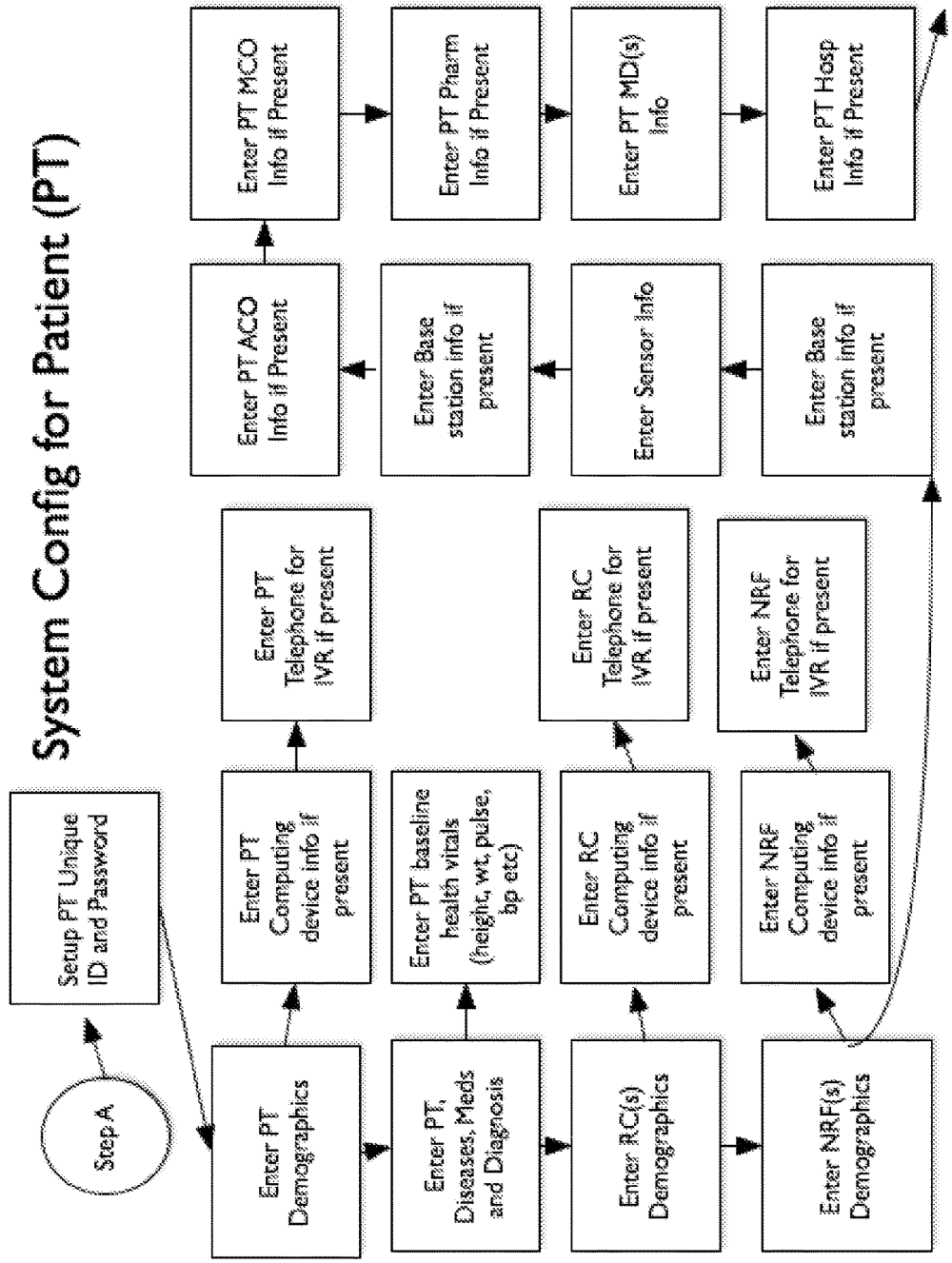
FIG. 4A is a flow chart for the system configuration for a patient of an exemplary embodiment of the method and system of the present disclosure.
Figure 4B:
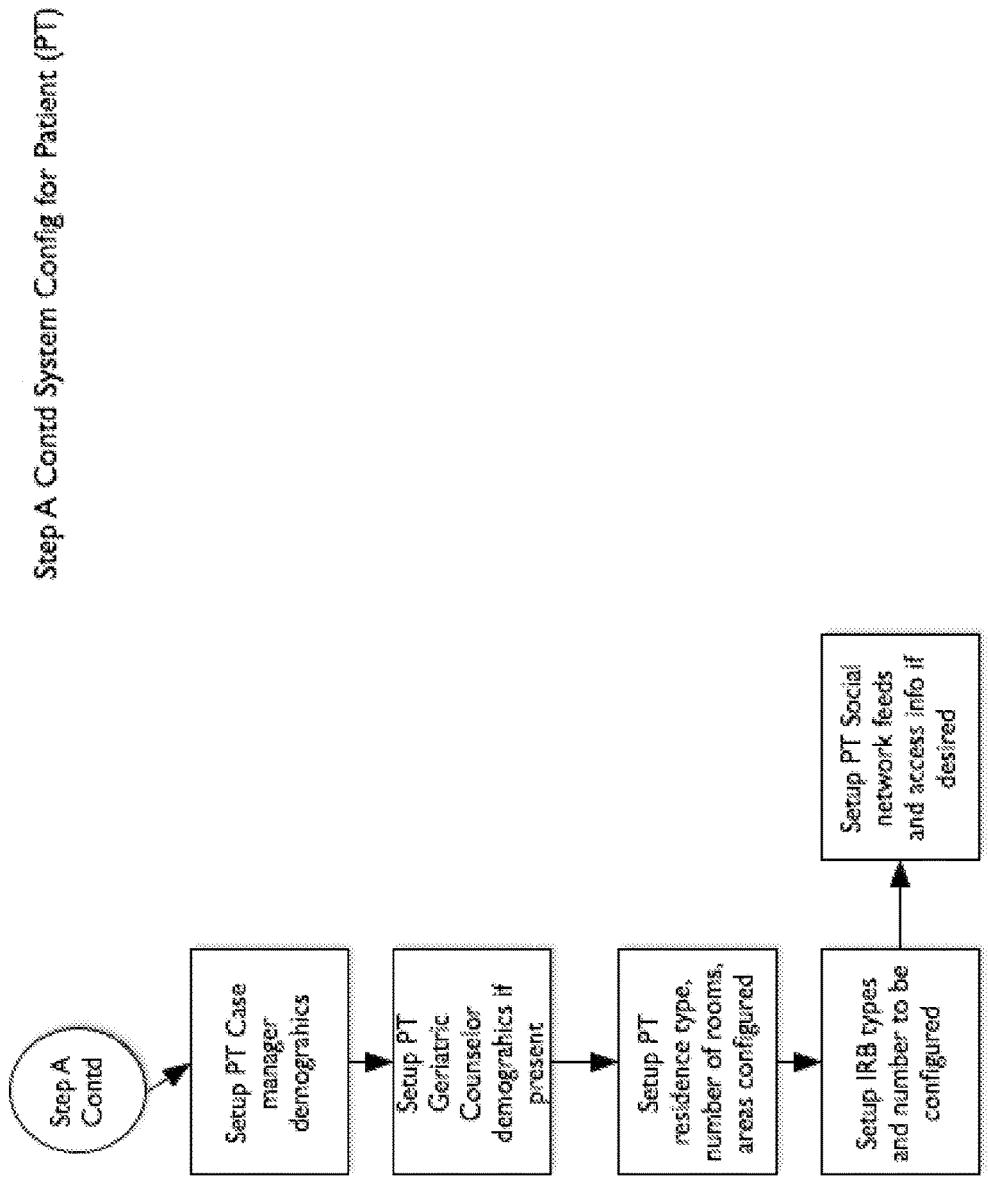
FIG. 4B is a flow chart for the system configuration for a patient, continued from FIG. 4A, of an exemplary embodiment of the method and system of the present disclosure.
Figure 5:
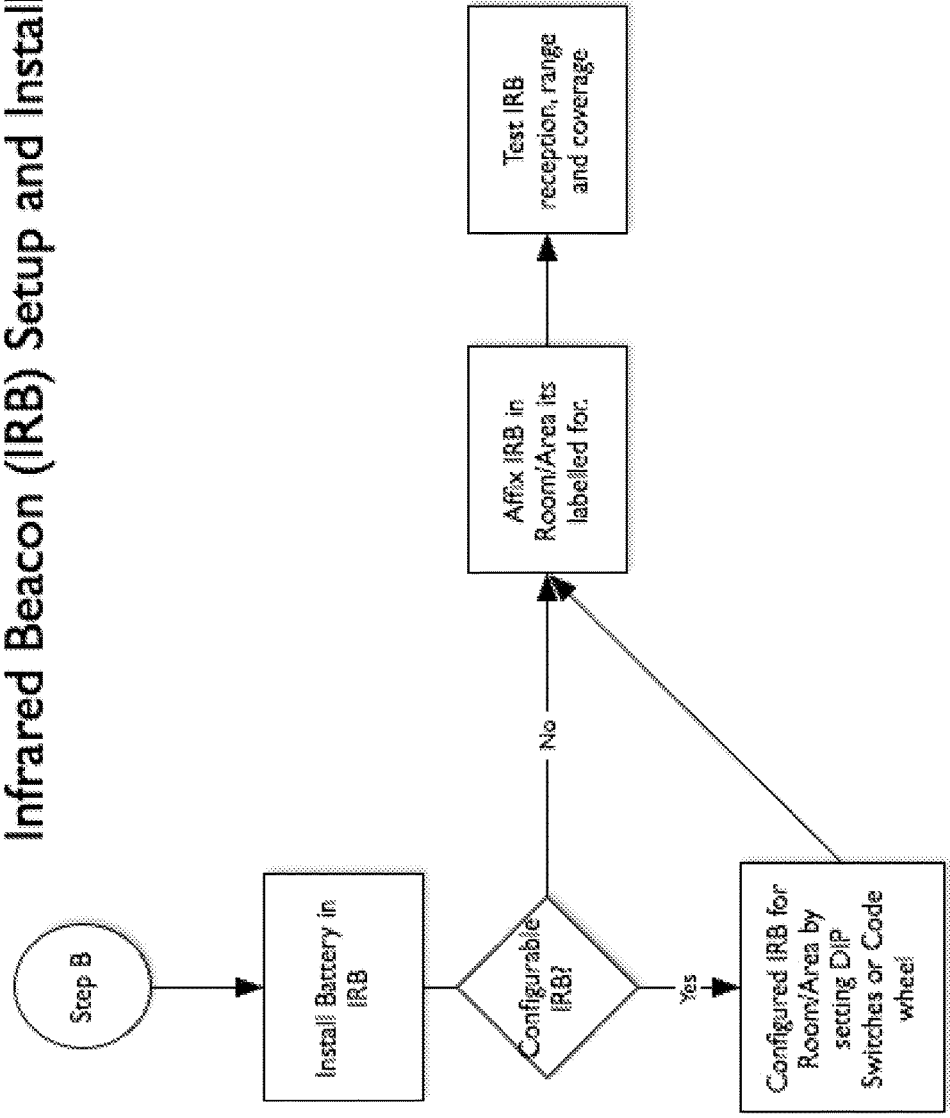
FIG. 5 is a flow chart for the infrared beacon setup and installation of an exemplary embodiment of the method and system of the present disclosure.
Figure 6:
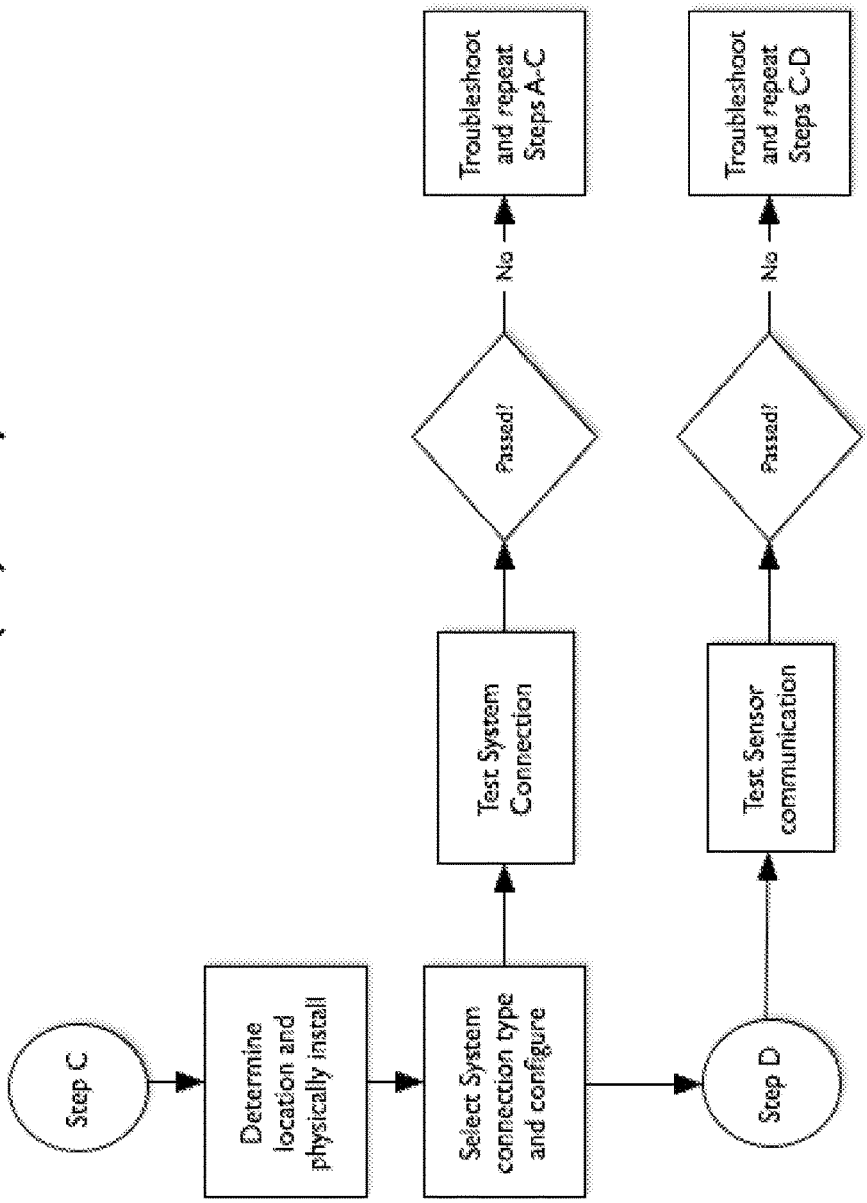
FIG. 6 is a flow chart for the base station setup and installation of an exemplary embodiment of the method and system of the present disclosure.
Figure 7:
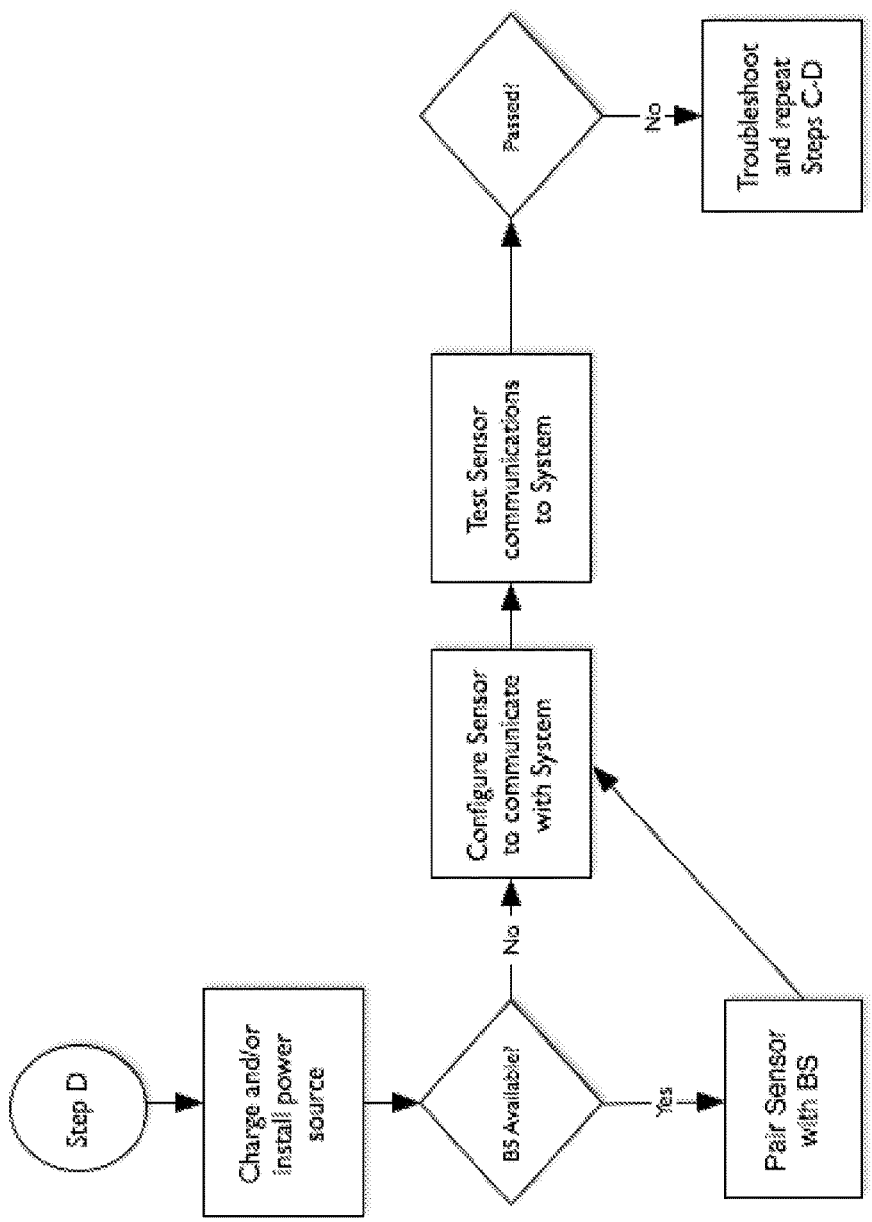
FIG. 7 is a flow chart for the sensor setup and installation of an exemplary embodiment of the method and system of the present disclosure.
Figure 8:
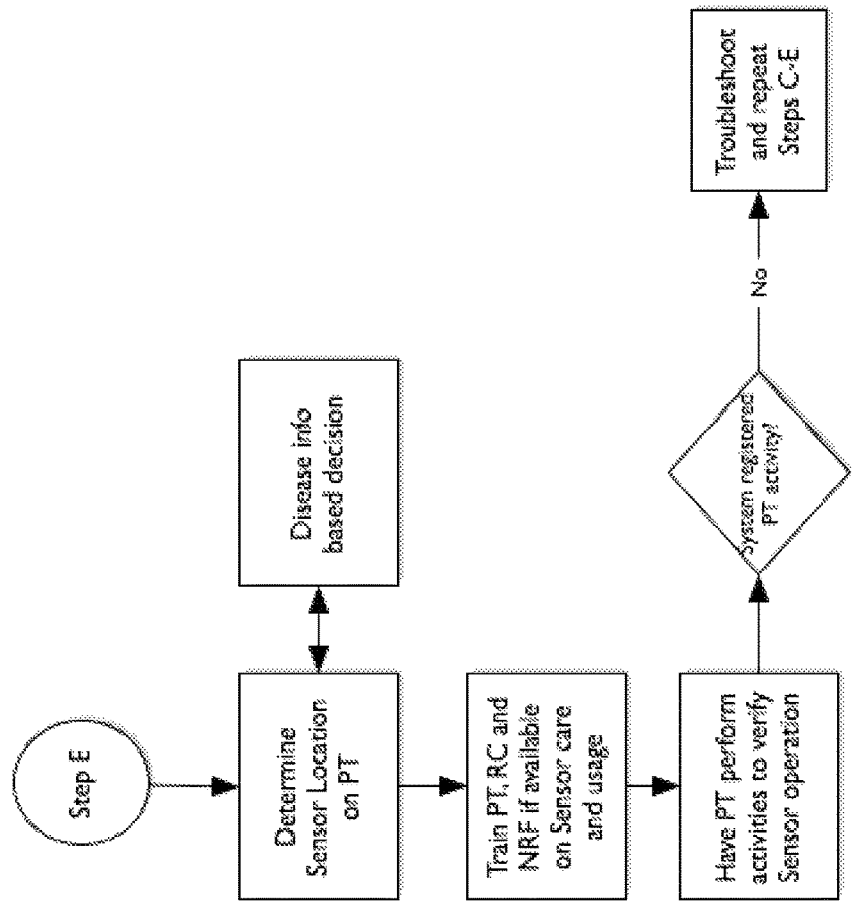
FIG. 8 is a flow chart for the sensor fitting on a patient of an exemplary embodiment of the method and system of the present disclosure.
Figure 9:
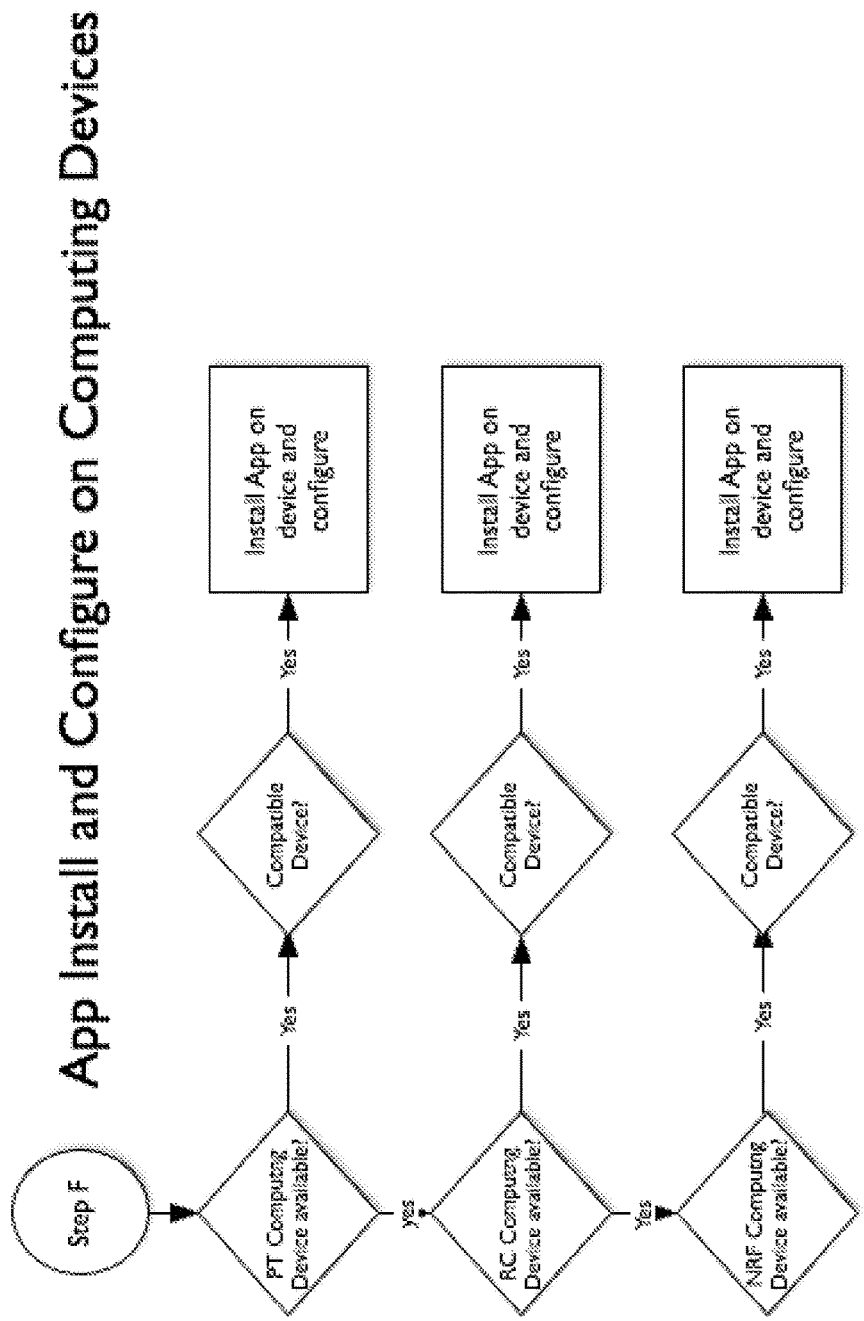
FIG. 9 is a flow chart for the software application installation and configuration on computing devices of an exemplary embodiment of the method and system of the present disclosure.

FIG. 3 is a flow chart of the overall setup and installation of an exemplary embodiment of the method and system of the present disclosure. As can be seen in FIG. 3, the overall system can be set up and installed in six steps, in the exemplary embodiment illustrated. In Step A, the system is configured for a patient, as illustrated in FIGS. 4A and 4B discussed below. In Step B, the Infrared Beacons are set up and installed, as illustrated in FIG. 5 discussed below. In Step C, the Base Station is set up and installed, as illustrated in FIG. 6 discussed below. In Step D, the Sensor is set up and installed, as illustrated in FIG. 7 discussed below. In Step E, the Sensor is fitted on the patient, as illustrated in FIG. 8 discussed below. In Step F, the application software (App) is installed and configured on computing devices used with the system, as illustrated in FIG. 9 discussed below.

Referring to FIGS. 4A and 4B, a flow chart for the system configuration for a patient, is disclosed. The system configuration for a patient preferably comprises the following steps: setup a patient unique ID and password; enter patient demographics, computing device information if present, and telephone for IVR if present; enter patient diseases, medications, and diagnosis, and patient baseline health vitals (height, weight, pulse, blood pressure etc.); enter Resident Caregiver(s) demographics, computing device info if present, and telephone for IVR if present; enter Non-resident Family member(s) and/or friends demographics, computing device info if present, and telephone for IVR if present; enter Sensor information; enter Base station information if present; enter patient ACO information if present; enter patient MCO information if present; enter patient pharmacy information if present; enter patient doctor information; enter patient hospital information if present; setup patient case manager demographics; setup patient geriatric counselor demographics if present; setup patient residence type, number of rooms, areas configured; set up infrared beacon types and number to be configured; and setup patient social network feeds and access information if desired.

Referring to FIG. 5, a flow chart for the infrared beacon setup and installation is disclosed. The infrared beacon setup preferably comprises the following steps: install battery in the infrared beacon(s); if the beacon is configurable, then configure the beacon for room/area by setting DIP switches or code wheel; affix the beacon in the room/area it is labeled for; and test the beacon reception, range and coverage.

Referring to FIG. 6, a flow chart for the base station setup and installation is disclosed. The base station setup and installation preferably comprises the following steps: determine location and physically install; select system connection type and configure; test system connection; if the system connection did not pass the test, then troubleshoot and repeat Steps A-C.

Referring to FIG. 7, a flow chart for the sensor setup and installation is disclosed. In some embodiments, the sensor setup and installation may comprise the following steps: charge and/or install power source; if the base system is available, then pair the sensor with the base system; if the base system is not available, the configure the sensor to communicate with the system; test the sensor communications to the system; and if the sensor communications did not pass the test, then troubleshoot and repeat steps C-D.

Referring to FIG. 8, a flow chart for the sensor fitting on the patient is disclosed. The sensor fitting on the patient preferably comprises the following steps: determine sensor location on the patient based upon the disease information of the patient; train patient, resident caregiver and non-resident family member or friend, if available, on sensor care and usage; have patient perform activities to verify sensor operation; if the system does not properly register patient activity, then troubleshoot and repeat Steps C-E.

Referring to FIG. 9, a flow chart for the software application installation and configuration on computing devices is disclosed. The software application installation and configuration on computing devices preferably comprises the following steps: if a patient computing device is available, then determine if the device is compatible with the system, and if compatible, install the software application on the patient device and configure; if a resident caregiver computing device is available, then determine if the device is compatible with the system, and if compatible, install the software application on the resident caregiver device and configure; and if a non-resident family member or friend computing device is available, then determine if the device is compatible with the system, and if compatible, install the software application on the non-resident family member/friend device and configure.

Figure 10:
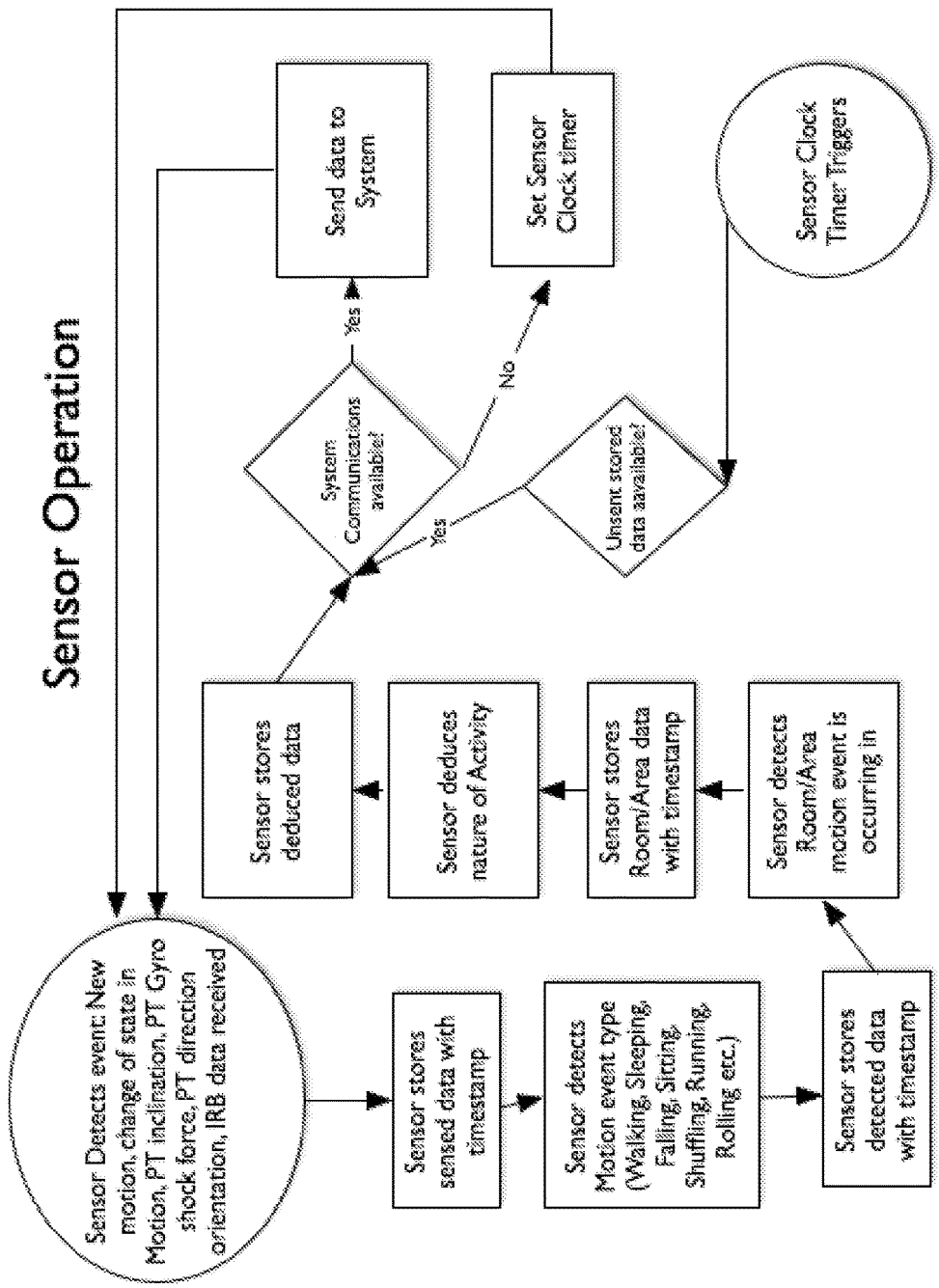
FIG. 10 is a flow chart for the sensor operation of an exemplary embodiment of the method and system of the present disclosure.

FIG. 10 illustrates a flow chart for the operation of the sensor of the method and system of the present disclosure. Specifically, when the sensor detects an event, such as new motion, change of state in motion, patient inclination, G-force, patient direction orientation, infrared beacon data received, etc., the sensor stores the sensed motion data with time-stamp. The sensor then detects the motion event type, such as walking, sleeping, falling, sitting, shuffling, running, rolling, etc., and stores the sensed motion type data with time-stamp. The sensor also detects the room/area where the motion event is occurring in and stores the room/area data with time-stamp. The sensor next deduces the nature of the activity and stores the nature of activity data. If system communications are available, then the sensor sends the stored data, and any previously unsent stored data if available, to the system. If system communications are not available, the sensor clock timer is set, and subsequently triggers the sensor to check if communications are available to send unsent data.

Figure 11:
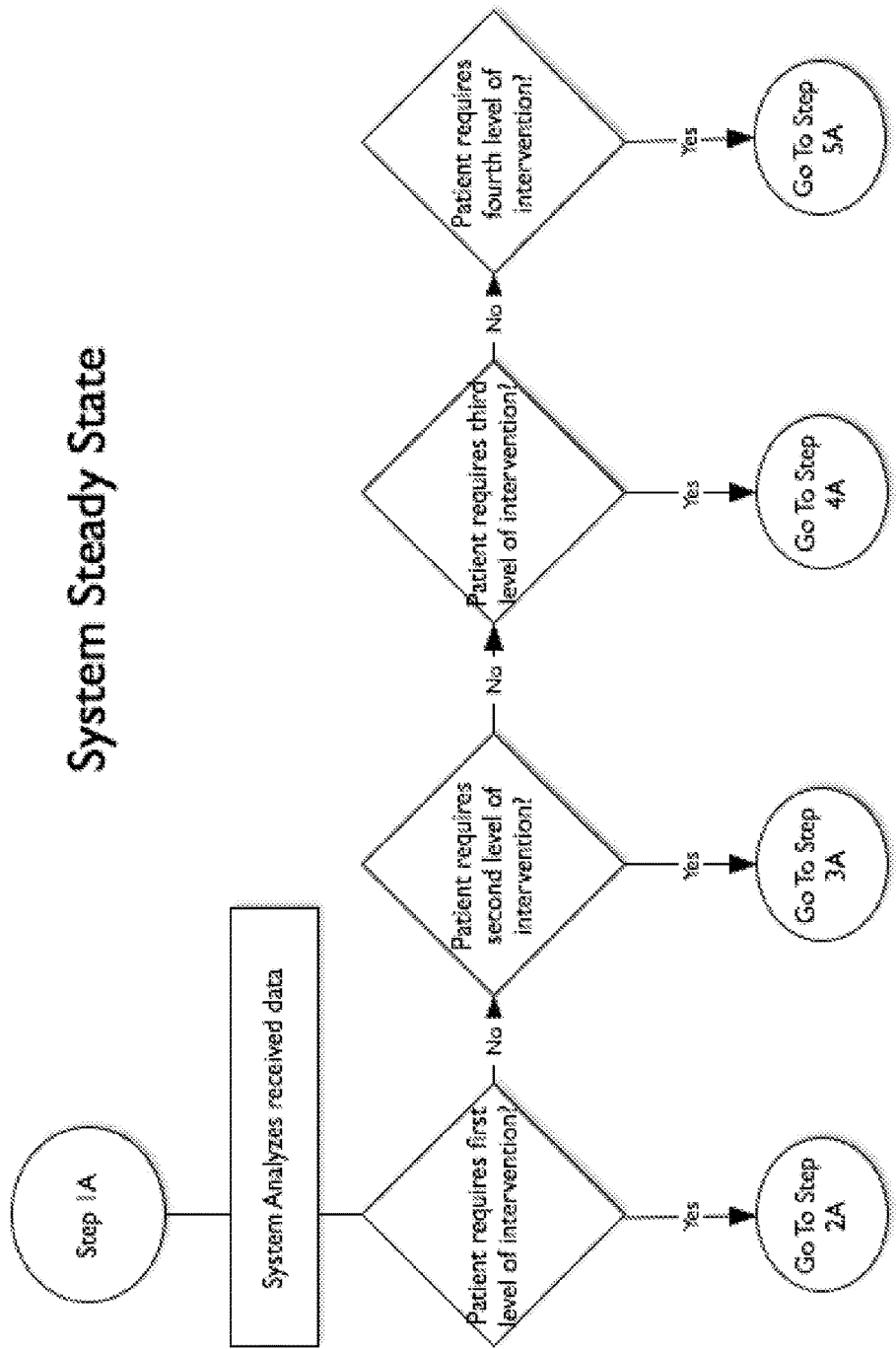
FIG. 11 is a flow chart for the system steady state of an exemplary embodiment of the method and system of the present disclosure.

FIG. 11-15 illustrate flow charts for the operation of the system of the method and system of the present disclosure. Specifically, FIG. 11 is a flow chart for the system steady state. When the system receives data from the sensor (step 1A), the system analyzes the data that is received, and based upon the data received and the analysis thereof, determines what level of healthcare intervention is required. If the system determines that the patient requires a first level of intervention, then the system initiates the patient contact step 2A, illustrated in FIG. 12. If the system determines that the patient requires a second level of intervention, then the system initiates the resident caregiver contact step 3A, illustrated in FIG. 13. If the system determines that the patient requires a third level of intervention, then the system initiates the non-resident family member or friend contact step 4A, illustrated in FIG. 14. If the system determines that the patient requires a fourth level of intervention, then the system initiates the clinical contact step 5A, illustrated in FIG. 15.

Figure 12:
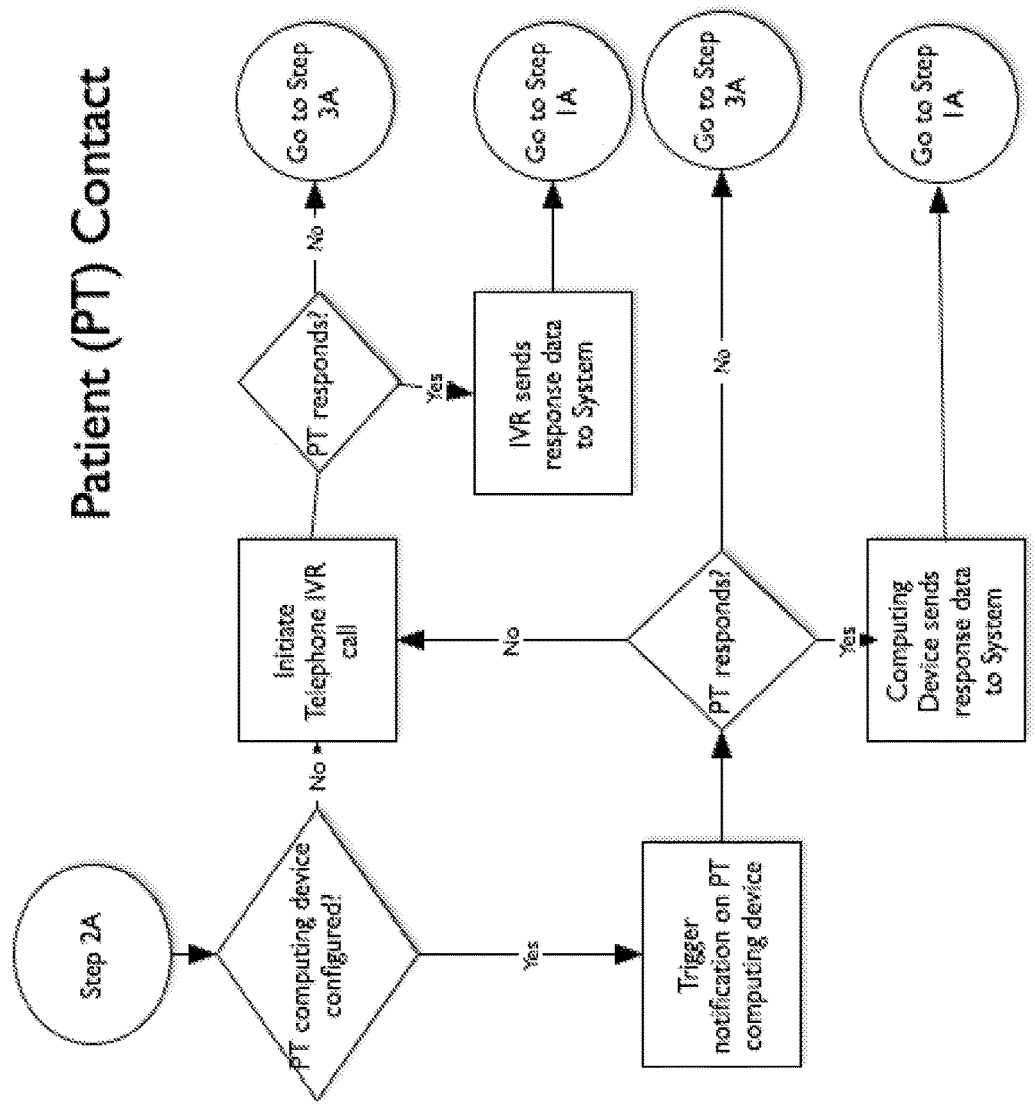
FIG. 12 is a flow chart for the patient contact intervention level of an exemplary embodiment of the method and system of the present disclosure.

FIG. 12 illustrates a flow chart for the patient contact intervention level (step 2A) of the method and system of the present disclosure. If a patient computing device is configured, then the system triggers notification on the patient computing device, discussed above with respect to FIG. 2. If the patient responds, then the patient computing device sends response data to the system, which proceeds back to step 1A. If the patient does not respond, then the system proceeds to step 3A. If a patient computing device is not configured, then the system initiates a telephone IVR call, discussed above with respect to FIG. 2. If the patient responds, then the IVR sends response data to the system, which proceeds back to step 1A. If the patient does not respond, then the system proceeds to step 3A.

Figure 13:
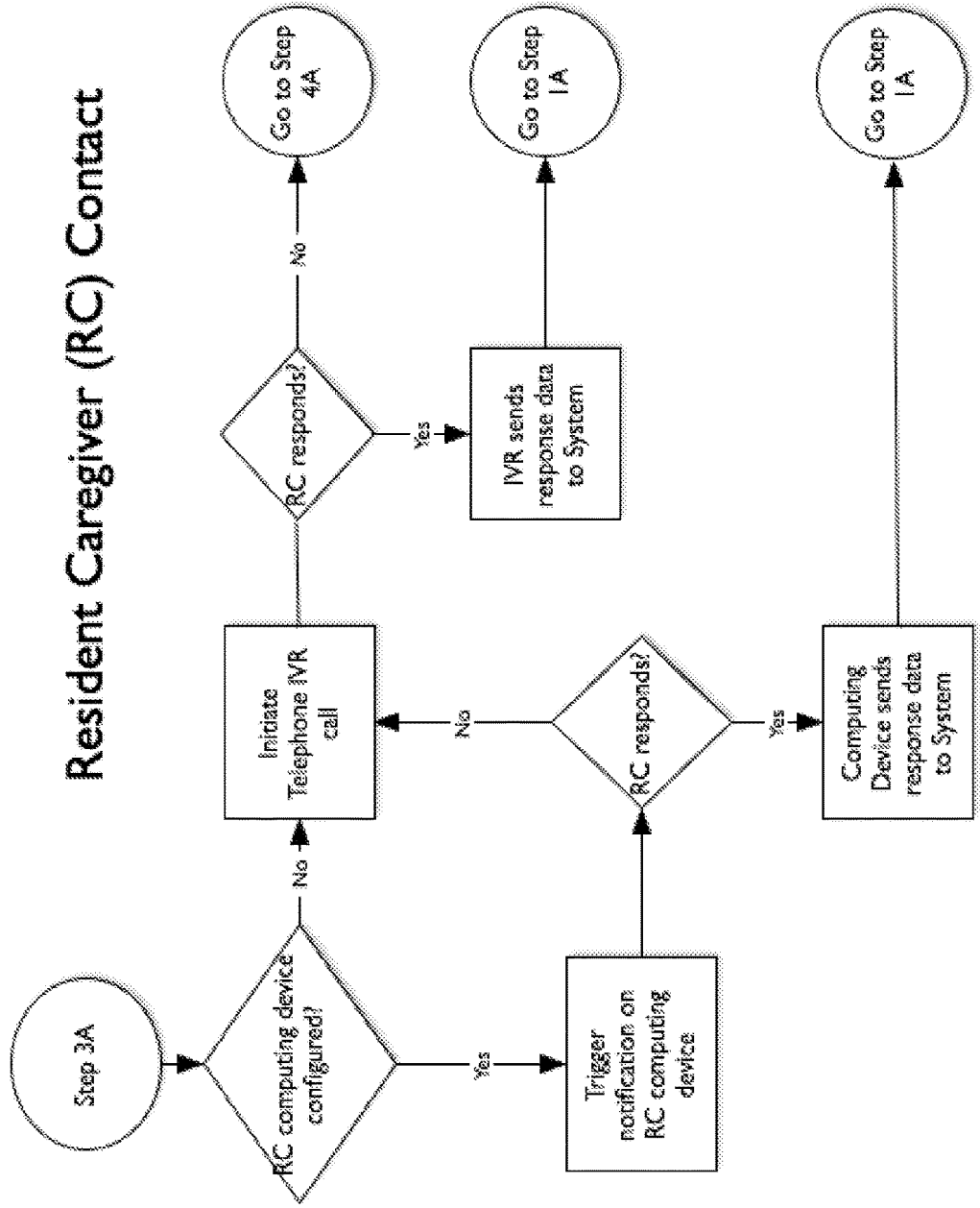
FIG. 13 is a flow chart for the resident caregiver contact intervention level of an exemplary embodiment of the method and system of the present disclosure.

FIG. 13 illustrates a flow chart for the resident caregiver contact intervention level (step 3A) of the method and system of the present disclosure. If a resident caregiver computing device is configured, then the system triggers a notification on the resident caregiver computing device, discussed above with respect to FIG. 2. If the resident caregiver responds, then the resident caregiver computing device sends response data to the system, which proceeds back to step 1A. If the resident caregiver does not respond, then the system, proceeds to step 4A. If a resident caregiver computing device is not configured, then the system initiates a telephone IVR call, discussed above with respect to FIG. 2. If the resident caregiver responds, then the IVR sends response data to the system, which proceeds back to step 1A. If the resident caregiver does not respond, then the system proceeds to step 4A.

Figure 14:
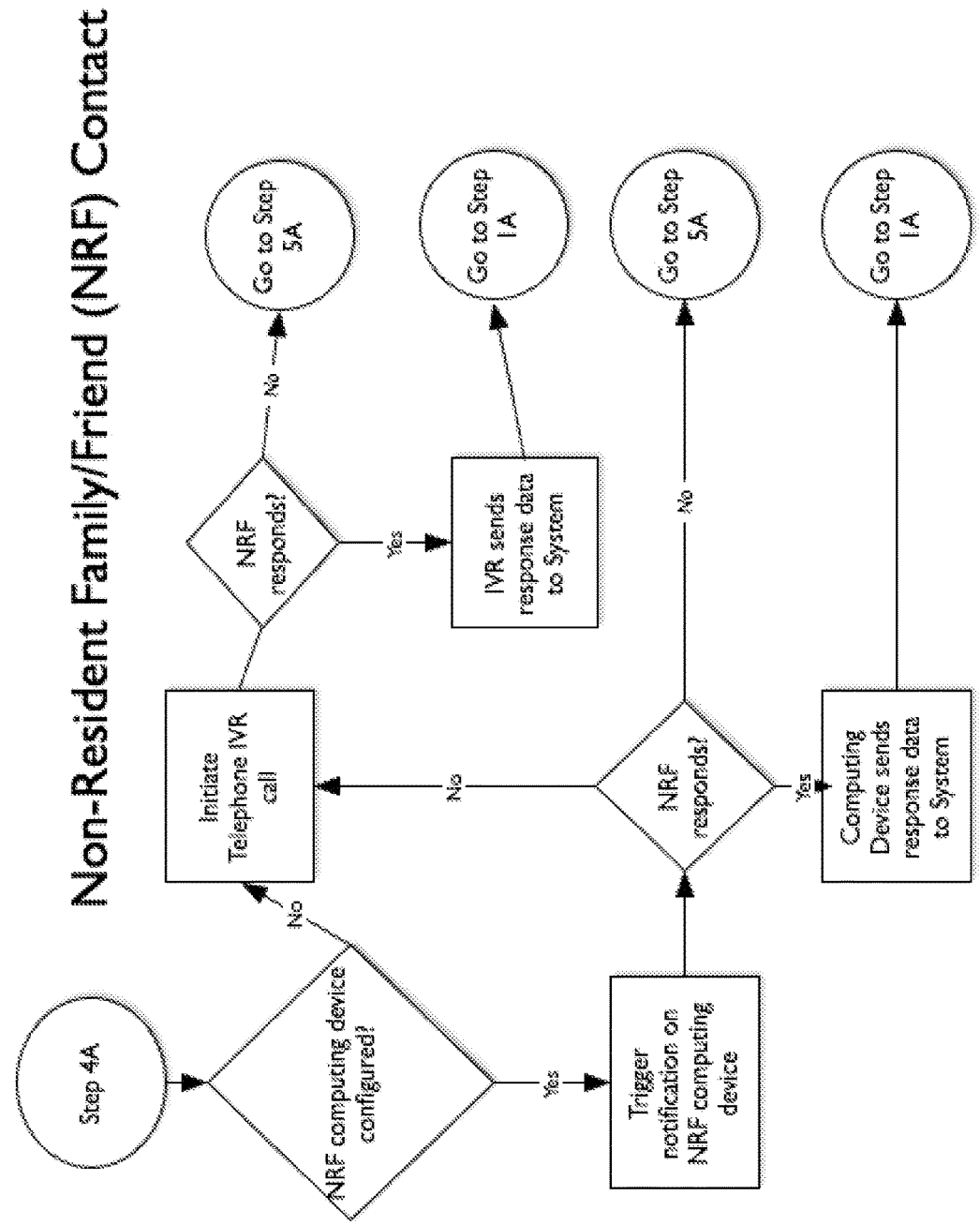
FIG. 14 is a flow chart for the non-resident family/friend contact intervention level of an exemplary embodiment of the method and system of the present disclosure.

FIG. 14 illustrates a flow chart for the non-resident family member or friend contact intervention level (step 4A) of the method and system of the present disclosure. If a non-resident family member or friend computing device is configured, then the system triggers notification on the non-resident family member or friend computing device, discussed above with respect to FIG. 2. If the non-resident family member or friend responds, then the non-resident family member or friend computing device sends response data to the system, which proceeds back to step 1A. If the non-resident family member or friend does not respond, then the system proceeds to step 5A. If a non-resident family member or friend computing device is not configured, then the system initiates a telephone IVR call, discussed above with respect to FIG. 2. If the non-resident family member or friend responds, then the IVR sends response, data to the system, which proceeds back to step 1A. If the non-resident family member or friend does not respond, then the system proceeds to step 5A.

Figure 15:
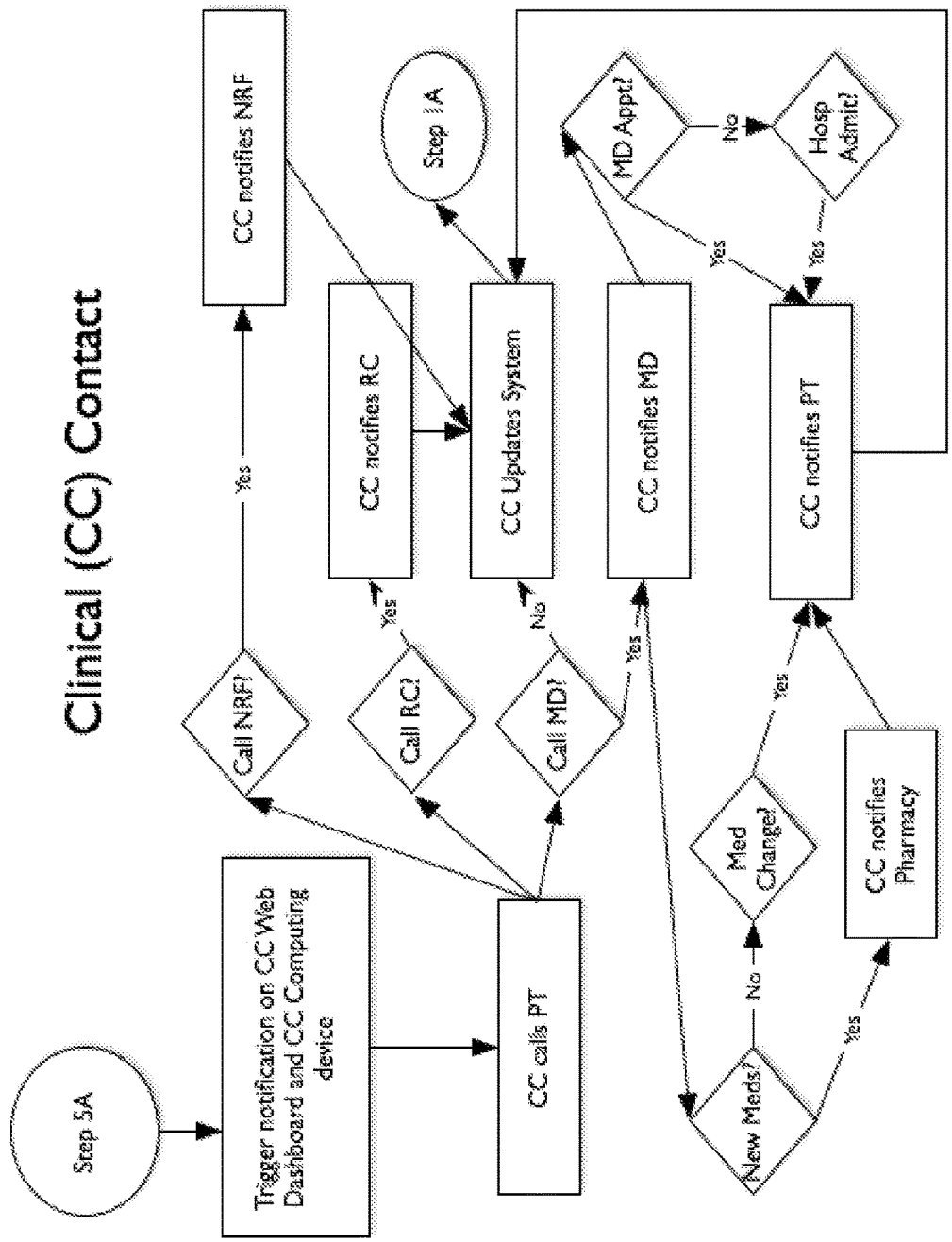
FIG. 15 is a flow chart for the clinical contact intervention level of an exemplary embodiment of the method and system of the present disclosure.

FIG. 15 illustrates a flow chart for the clinical contact intervention level (step 5A) of the method and system of the present disclosure. In this level of intervention, the system triggers notification on the clinical contact web dashboard or computing device. The clinical contact then can initiate calls to and or amongst the patient, the resident caregiver, the non-resident family member or friend, or the patient's doctor to obtain additional information, discussed above with respect to FIG. 2. Based upon the information gathered, the clinical contact can schedule a doctor visit, admit the patient to a hospital, communicate changes in medication or prescription of —new medications and notify the pharmacy and the patient, etc. The clinical contact updates the system with all of the new data and information, and the system then proceeds back to step 1A.

Accordingly, from the above description, it can be seen that the disclosed methods and systems keep the patient in the lowest cost care setting, the home, and use a sentinel system utilizing wearable sensors technology to determine when functional state is declining or patterns of activity change and trigger progressively higher levels of intervention, from "free" hands and eyes to skilled clinicians.

The Sensor and infrared beacon, or other room identifying devices, together allow for the detection of the room/area in which the patient activity is taking place. Thus, the Sensor detects not just the type of activity but where it is taking place so deductions can be made. For example, if the sensor detects a sitting posture and the room/area as Bathroom, the system can infer that the patient is using the toilet. If the sensor senses that the patient is standing and taking small steps, and room/area detected is the Kitchen, the system can infer that the patient is preparing food or drink. The sensor helps the system build a baseline of activity and also a "normal" pattern of daily behaviors for each patient.

The system can determine if the patient's functional state is declining. For example, the system can determine that a patient normally wakes up at 7:30 AM and walks on average 300 steps by 8 AM, but has now started walking far less in the same time. The system can also determine changes in a patient's pattern of activities. For example, the system can determine that a normal pattern of activity for a patient is to go from Bedroom to Bathroom, spend 20 minutes, go to Kitchen spend 10 minutes and then sit in the Living Room for the rest of the morning, but today the patient went from Bedroom to Bathroom and back to Bedroom where the patient stayed the whole morning in a prone position.

The system can determine additional data points on the progression of the disease state by presenting Observatory and Interrogatory questions to the Patient and others. The system can determine additional data points by prompting the patient to perform certain activities that are disease specific (for example: walk 10 steps) and then measuring the actual demonstrated activity and timing in real-time or near real-time via the sensor, as well as ask disease specific follow-up questions at the end of demonstration such as "are you short of breath" to further corroborate analysis.

When a pattern change or decline in functional activity is noticed, the system contacts the patient. The patient is contacted either via an App (if they are capable) or via Telephone IVR. The patient is asked questions that may encompass general, emotional state as well as disease specific. The questions are stored in the systems database(s) and are formed from established clinical guidelines (for example Seattle Obstructive Lung Disease Questionnaire, or SOLDQ in the case of a COPD patient), and responses are scored. The System can prompt the patient to perform a series of activities as part of the questionnaire and the Sensor can monitor and report back to the System in real-time or near real-time.

If a patient cannot be contacted or additional data points are needed, the system triggers the First Circle of Care: The Resident Caregiver (RC) if one is present (e.g., Spouse, Partner, Friend/roommate) is contacted either via an App (if they are capable) or via Telephone IVR. The RC is presented with questions they can answer by observing the patient. The RC is presented with questions that they can ask Patient (interrogatory component) and report answers back to the system. The questions asked are disease specific and based on established questionnaires in academic research.

If additional data points are needed, the system triggers the Second Circle of Care: The Non-Resident Family member or Friend (NRF) if one is present (e.g., Sibling, Adult Children, Friends) are contacted either via an App (if they are capable) or via Telephone IVR. The NRF is presented with questions they can answer by observing the patient. The NRF is presented with questions that they can ask Patient (interrogatory component) and report answers back to the system. The questions asked are disease specific and based on established questionnaires in academic research.

If analysis warrants further escalation, the system triggers the Third Circle of Care: The Clinical Contact (CC) at an ACO, MCO or LiveOps Center is contacted either via an App (if they are mobile) or via a web dashboard. The System displays patient history, its analysis thus far, questions and responses and scoring of answers from the Patient, RC and NRF as well as normal baseline functional scores and patterns of activity versus current observed anomalies for review. The CC reviews data and determines next course of action.

The CC uses human intelligence to determine the next appropriate course of action which maybe one or more of: Call Patient, or RC or NRF to gather additional data; Dispatch a nurse/therapist for an onsite visit to verify clinical condition or perform a clinical intervention; Contact MD to review patient history and current state; Determine if change in medications or new medications are needed, and contact Pharmacy and Patient as needed; Schedule an office visit with MD if appropriate; and/or Schedule a hospital admission if appropriate. The CC then updates the System with all actions taken and any other relevant information.

Example of System in Use

The following narrative represents a hypothetical Use Case scenario illustrating the methods and systems of the present disclosure in use:

Mr. Jones is an 85 year old male patient in Florida. Mr. Jones lives at home with his spouse, 75 year old Mrs. Jones, who is of reasonable health. Mr. Jones is a Medicare beneficiary. The Jones have their son Sam, 48 years old, living 5 miles away and another son, Kyle, living in California. In addition, Mr. Jones close friend Mr. Pablo lives next door.

The Jones lives in a condo that has one bathroom, a living room, a bedroom, a kitchen and a dining room. The home has Internet access and Mrs. Jones is an avid user of a tablet computer. The Jones have a land line phone and a cell phone that Mrs. Jones carries. Sam and Kyle are avid users of smartphones and tablet computers. Mr. Pablo uses his desktop computer primarily to browse the internet and to keep in touch with his family via email and social media.

Mr. Jones was diagnosed with a chronic care condition of Chronic Obstructive Pulmonary Disease (COPD) 5 years ago. Mr. Jones has been hospitalized for his condition several times. Mr. Jones uses a regimen of medication to manage his chronic disease. Mr. Jones was most recently discharged from the hospital a few days ago. At his discharge the Hospital and MD prescribed use of the disclosed system at no cost to Mr. Jones.

The hospital entered all of Mr. Jones information including his demographics, disease, etc., Mrs. Jones contact information, Sam and Kyle's information, as well as Mr. Pablo's information among others, into the system. A wearable sensor was fitted on Mr. Jones leg at his discharge and a self-install kit of five Infrared (IR) beacons labeled "Kitchen", "Bathroom", Living Room", "Dining Room", "Bedroom" were provided to him, as well as a charger and a Base station with instructions on installation. Mr. Jones' son, Sam, came by to affix the small beacons in the respective rooms following the instructions on placement. The charging plate was installed by Mr. Jones' bed side, and Mr. Jones was instructed on removing the sensor and placing it on the charger plate for recharging when the sensor indicated that its battery was running low.

The base station was then plugged in and the Sensor was tapped three times to communicate with the base station and perform a communications system check. The Sensor green LED lit to indicate success, and then Mr. Jones, following the installation instruction, walked into each of the separate rooms in turn. In each room, the sensor detected the distinct room by detecting the infrared beam and decoding the room ID contained in the beam for the specific room Mr. Jones was in, and vibrated and lit its green LED to indicate success.

The System sends Mrs. Jones a link to install Apps on her tablet computer, which she does successfully. The System sends Sam and Kyle a link to install Apps on their tablet computers and smartphones, which they successfully do. The System sends Mr. Pablo a link to install Apps on his desktop computer, which he does successfully.

Day 1-7: The sensor monitors Mr. Jones' activities over an initial period, for example seven days to create a baseline of normal activity and to note patterns of behavior. It determined on average that Mr. Jones woke up each day at 5:30 AM and walked about 250 steps in the 60 minutes. It noted that Mr. Jones went from the bedroom upon waking to the bathroom (taking about 30 seconds), where he spent 15 minutes and then he went to the kitchen where he spent 5 minutes and then went to the living room and sat for 2 hours. At about 8:00 AM, Mr. Jones went out of the condo (lack of IR signals, loss of connectivity to the base station) and walked for 30 minutes and then came back to the condo (detection of IR beams, regaining base station connectivity). Upon coming back in range the sensor transmitted the activity details that occurred when the sensor was out of range of the base station.

Day 7-14: The sensor continues to monitor Mr. Jones and no statistically significant variances in functional level or change in patterns of activity is detected by the system.

Day 15: The sensor detects normal pattern of activity but also that Mr. Jones is taking longer (but not statistically significant) to walk the same distances.

Day 16: The sensor detects variations in normal pattern of activity and that Mr. Jones is taking longer to walk the same distances (but neither is statistically significant). The system sends a push notification to Mrs. Jones and she responds on her app to several questions generated by the system from its databases based upon the sensed information:

a. Is Mr. Jones walking normally?—Yes
   b. Is he shuffling?—No
   c. Does he seem out of breath?—Yes
   d. Is he eating normally?—Yes The system records Mrs. Jones' responses for subsequent analysis.

Day 17: The sensor detects a normal pattern of activity, but also a statistically significant longer time to cover the same distances. The system calls Mr. Jones through its IVR telephone system and has him answer several questions:

a. Are you feeling short of breath?
b. Are you breathing heavily?
c. Have you been practicing the energy conservation techniques taught at discharge?
d. Do you have any pain?
e. Are you feeling tired?

Based on Mr. Jones responses, the System sends a notification to Mrs. Jones and her App prompts her to answer some observational questions about Mr. Jones.

a. Is Mr. Jones breathing laboriously?—Yes
b. Was he snoring last night?—Yes
c. Does he seem tired?—Yes
d. Is his face puffy?—Yes
e. Are his ankles swollen?—No The system records Mr. Jones' responses, and Mrs. Jones' responses for subsequent analysis.

Day 18: The sensor detects Mr. Jones waking up at 6:30 AM, goes to the bathroom for 10 minutes, then to the Kitchen and then Living room but returns to the bedroom where he lies down again for the next one hour. He has only taken 100 steps when normal activity is 250 steps. It also notes that the time taken to go from the bedroom to the bathroom is 60 seconds, statistically longer than the 30 second normal time. Sensor communicates this data to the System. The System determines an anomaly is occurring.

Since Mr. Jones does not use a computer, the System initiates an IVR Telephone call to the land line of the Jones residence. Mr. Jones picks up the phone and System identifies itself. The System prompts Mr. Jones to "Press 1 if Mr. Jones is available to speak" or Press 2 for No. Mr. Jones presses 1. The System explains the reason for call: "we note that you did not follow your normal routines this morning." The System asks "Are you feeling unwell?" Press 1 for Yes, 2 for No. Mr. Jones responds with 1. The System then asks "Do you feel up to answering a few questions?" Press 1 for Yes, 2 for No. Mr. Jones responds with 2. The System then says, "Ok, please let Mrs. Jones know that we will contact her for some follow-up questions" and hangs up.

System next sends a push notification to Mrs. Jones tablet app. Mrs. Jones opens the App and the System notifies Mrs. Jones that: "We are contacting you as Mr. Jones seems unwell and we'd like to ask for your assistance in determining how he is feeling." The App requests Mrs. Jones to observe Mr. Jones and answer several observational questions:

a. Is Mr. Jones ankles swollen?
b. Is his skin color pale or normal?
c. Does he have a fever?
d. Is he coughing?
e. Does he seem short of breath?
f. Is he breathing heavily?
g. Did he eat normally last night?
h. Did he eat anything unusual last night?

After receiving responses to these questions, the App then asks Mrs. Jones to pose several interrogatory questions to Mr. Jones and enter his responses in the app. Specifically, in this scenario, the interrogatory questions are twenty questions from the Chronic Respiratory Disease Questionnaire (CRDQ) questionnaire to determine Dyspnea, Fatigue, Emotional burden and mastery of the disease. CRDQ is designed to be administered by an interviewer. All are multiple choice format and written for easy comprehension. Based on the entered responses, the system finds Mr. Jones' responses to the questions related to the emotional function to be outside the normal range.

The System then sends a push notification to Sam, Kyle and Mr. Pablo's computing devices, informing them of Mr. Jones' status, and optionally requesting that they take a desired action or respond to further questions. Sam decides that he will stop by on his way to work the next day to see how his dad is doing. Kyle is travelling and decides that when he gets home two days hence he will call Dad to see how he is doing. Mr. Pablo responds to the notification and walks over next door to Mr. Jones home to see how he is doing and "boost his spirits". He brings with him the newspaper to read stories to his friend and engage him. The Sensor detects in the meantime that Mr. Jones has visited the bathroom several more times during the day but is still going back to lie down. Mr. Jones has his dinner and goes to sleep.

Day 19: Mr. Jones wakes up the next day at 6:30 AM and walks to the bathroom, kitchen and then back to the bedroom. The System notes further decline in activity and larger change in pattern of normal behavior. The System triggers another notification to Mrs. Jones, Sam and Kyle. Sam stops by in the morning and the app on his smartphone prompts him to respond to a few observational questions:

a. Is Mr. Jones ankles swollen?
b. Is his skin color pale or normal?
c. Does he have a fever?
d. Is he coughing?
e. Does he seem short of breath?
f. Is he breathing heavily?
g. How is his mood?

The App asks Sam to see if he can encourage his Dad to take a 6 minute walk test. Mr.

Jones says Ok. Mr. Jones commences walking and the App on Sam's smartphone times him, while the sensor measures how many steps he has taken in the 6 minutes. However, Mr. Jones is unable to complete the test and stops after 1 minute. Sam is then prompted to ask Mr. Jones a follow-up question on if he is feeling short of breath and his response is entered. System determines that based on responses thus far, a nurse call is needed.

System initiates notification to the LiveOps center where a nurse gets a notification on her dashboard. The nurse reviews the information presented by System, for example, pattern change seen, and responses from Sam, Mrs. Jones and Mr. Pablo. The Nurse calls Mr. Jones to talk to him and to determine how he is feeling. The Nurse determines Mr. Jones is feeling short of breath and has trouble talking. The Nurse then calls the MD and discusses Mr. Jones' situation, and they decide a medication dose change is needed. The Nurse communicates the change in medication regimen to Mrs. Jones and Mr. Jones. As a result, Mr. Jones alters his medication.

The System continues to monitor his activity and patterns and sees improvements gradually. The System periodically pushes notifications to Mrs. Jones, Sam and Mr. Pablo to ask observational and interrogatory questions of Mr. Jones. System tracks that responses are trending positive. Over a period of a few days, Mr. Jones regains his normal pattern of activity.

The above scenario demonstrates the use of the system in a simple case where a slow functional decline is detected over a period of a few days. The use of spouse, family members and friends to conduct observational functions as well as interrogatory functions effectively removed the need for a nurse home visit in this case.

The use of the system as a sentinel effectively provided an early warning system that efficiently utilized higher levels of resources only when needed (Nurse/MD) to ultimately effect a medication change that made Mr. Jones feel better and prevented a continued decline in state of health that could have resulted in an ER visit, or a hospital admission.

Without this system in place, it is conceivable that on Day 20 or Day 21 when decline is much greater, the Jones would have called their MD for advice, who then may simply schedule a nurse visit on Day 22 or perhaps an office appointment on Day 22 or simply, with an abundance of caution, direct Mr. Jones to the nearest ER. Alternately, by Day 22, by the time the nurse visits or the office visit is due, Mr. Jones health is significantly worse and he may end up going to ER in an ambulance anyway.

Since re-hospitalization was prevented, the hospital, which discharged Mr. Jones less than 30 days ago, does not have the financial burden of caring for Mr. Jones for free due to re-admission for the same diagnosis within 30 days after discharge. In addition, the ACO that the Hospital is part of now can show statistics that they have improved patient outcomes even when the patient is outside their care setting, by employing this remote monitoring sentinel system and thus be eligible for performance bonus from Medicare. Further, because the ACO and Hospital outcomes statistics are made public and ranked by Medicare, both entities stand to benefit by the better reputation for outcomes and quality and can attract more patients. In both cases the few hundred dollars the hospital or ACO spends on this sentinel system per month per patient saves them many thousands of dollars in potential revenue loss, gains of several thousands in performance dollars due to better outcomes and potentially a better reputation, which virtuously delivers more business.

The components of the system can take any suitable form, including any suitable hardware, software or other computerized components including but not limited to servers, processors, databases, memory devices, mobile applications, etc., capable of adequately performing their respective intended functions, as may be known in the art. Further, while the embodiment(s) are illustrative of the structure, function and operation of the exemplary method(s) and system(s), it should be understood that various modifications may be made thereto with departing from the teachings herein.

Location Tracking Platform

Figure 16:
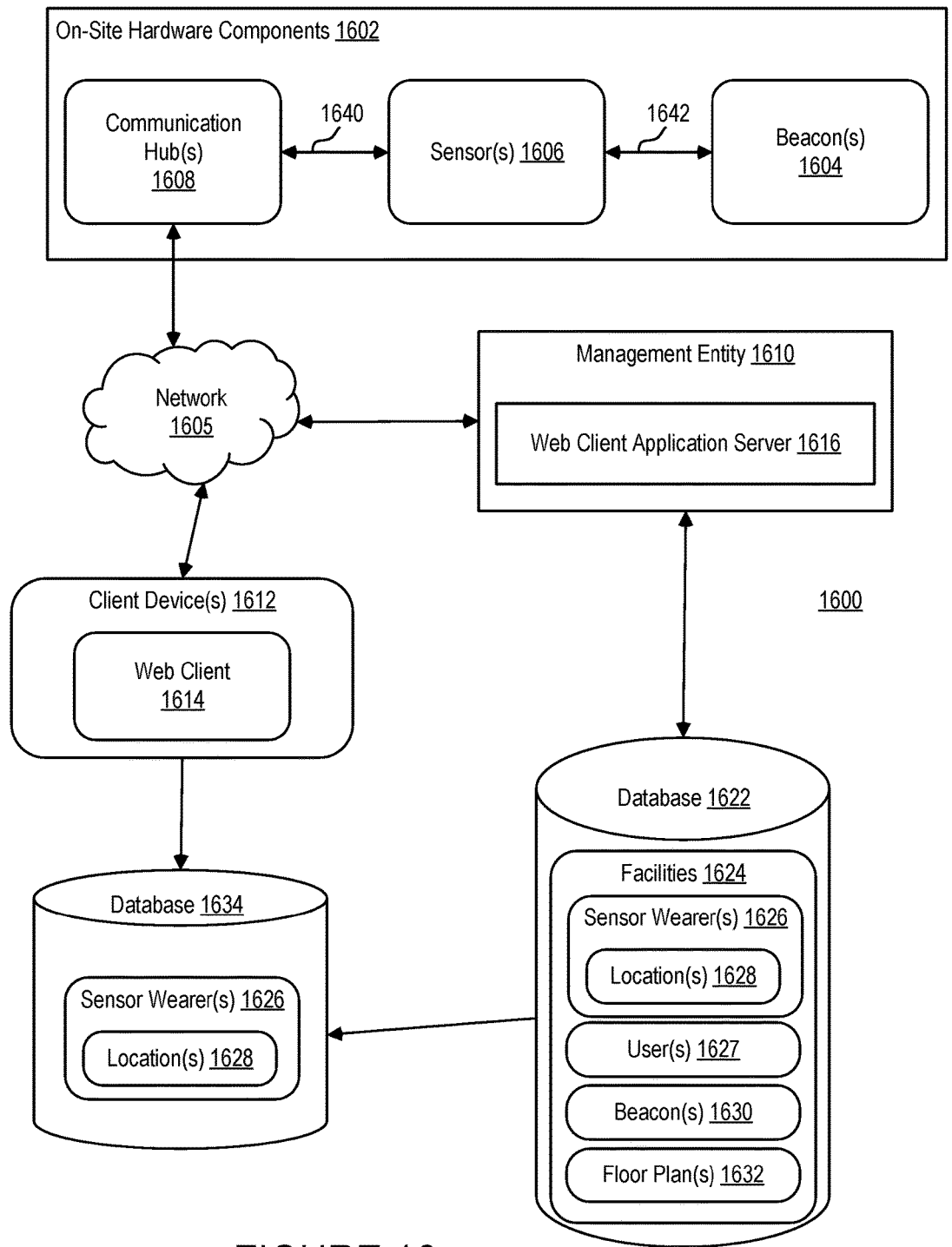
FIG. 16 is a block diagram of an example computing environment according to one embodiment of the present disclosure.

FIG. 16 illustrates a computing environment 1600, according to one embodiment.

Computing environment 1600 may be used to practice one or more the techniques disclosed herein. In one particular application, computing environment 1600 may be used to track a location of a patient throughout an assisted living facility or a hospital. Computing environment 1600 provides real-time, or near real-time, location information of staff and residents. Further, computing environment 1600 is able to alert supervisors when specified residents enter sensitive, or restricted, areas. Still further, computing environment 1600 allows residents and staff to press a button to seek assistance. When assistance is requested, location tracking allows the staff to quickly determine whom is in need and where they are located. Those skilled in the art could readily understand that the facility could be a variety of facilities, and should not be limited to health care services.

Computing environment 1600 may include on-site hardware components 1602 in communication with one or more remote components. On-site hardware components 1602 may include one or more beacons 1604, one or more sensors 1606, and one or more communication hubs 1608. For illustrative purposes, FIG. 16 illustrates a communication link 1642 between the sensors 1606 and the beacons 1604, and a communication link 1640 between the sensors 1606 and the communication hubs 1608.

Figure 17:
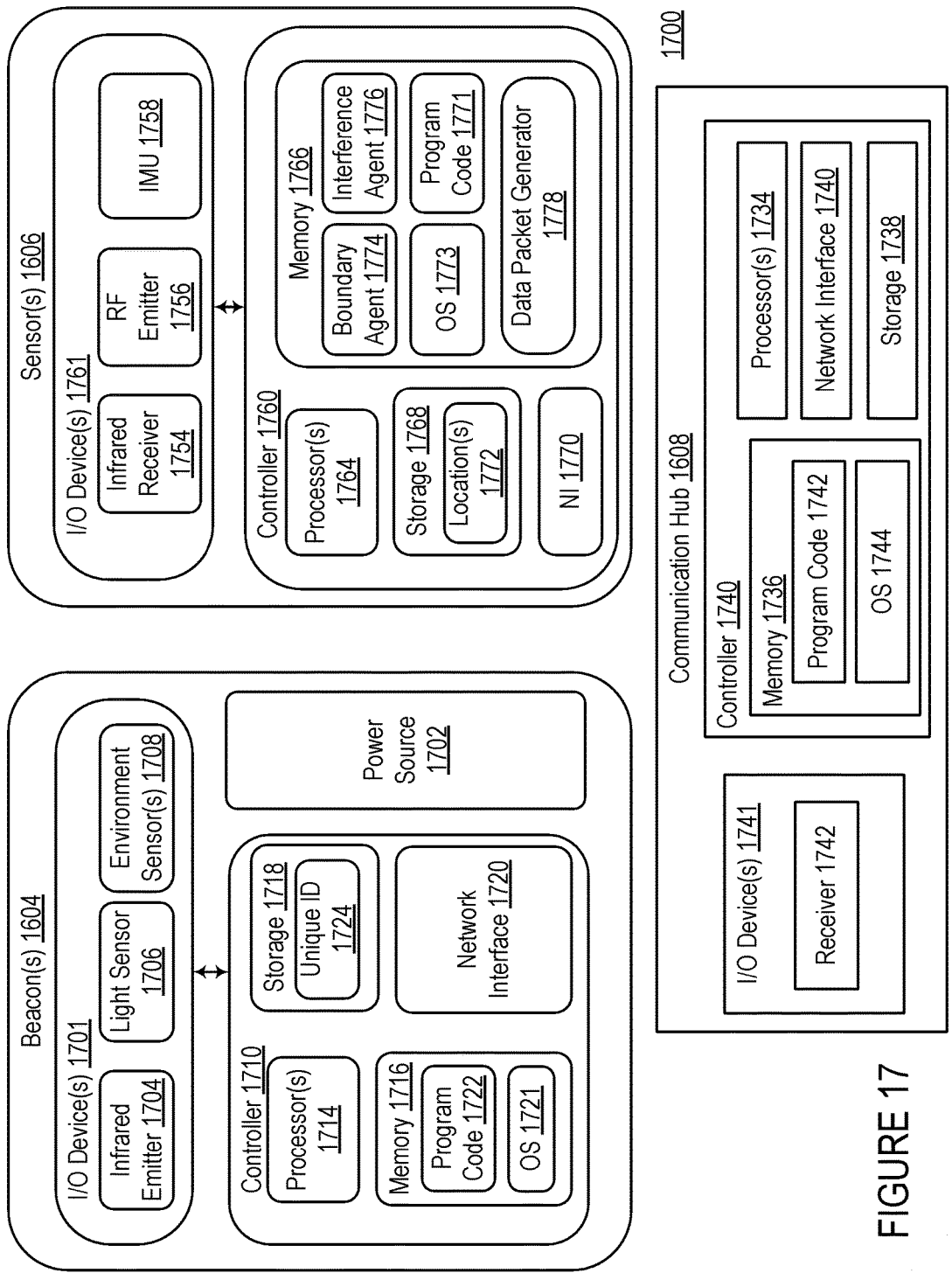
FIG. 17 is a block diagram illustrating a more detailed disclosure of example components in the computing environment of FIG. 16 according to one embodiment of the present disclosure.

Beacons 1604 may be installed throughout a facility. Generally, each beacon 1604 is placed in an area where monitoring is desired. For example, each room of a facility may include one or more beacons 1604 installed therein. FIG. 17 illustrates a single beacon 1604, according to one embodiment. Each beacon 1604 may include a controller 1710, a power source 1702, and one or more I/O devices 1701. Power source 1702 may include any suitable type of power sources, including, without being limited to, any form of alternating current (AC) or direct current (DC) power sources.

Controller 1710 may include a processor 1714, a memory 1716, a storage 1718, and a network interface 1720. Controller 1710 may be coupled to one or more I/O devices 1701.

Processor 1714 retrieves and executes programming code 1722 (i.e., programming instructions) stored in memory 1716, as well as stores and retrieves application data. Processor 1714 is included to be representative of a single processor, multiple processors, a single processor having multiple processing cores and the like. Network interface 1720 may be any type of network communications allowing controller 1714 to communicate externally via a computing network.

Memory 1716 may store operating system 1721 and program code 1722. Program code 1722 is accessed by processor 1714 for processing. Program code 1722 may include, for example, steps discussed below in conjunction with FIGS. 18-24. Although memory 1716 is shown as a single entity, memory 1716 may include one or more non-transitory memory devices having blocks of memory associated with physical addresses, such as random access memory (RAM), read only memory (ROM), flash memory, or other types of volatile and/or non-volatile memory.

Storage 1718 may be, for example, a disk drive storage device. Although shown as a single unit, storage 1718 may be a combination of fixed and/or removable storage devices, such as fixed disk drives, removable memory cards, optical storage, network attached storage (NAS), or storage area network (SAN). As illustrated, storage 1718 may include unique identifier (ID) 1724. Each beacon 1604 may be programmed with its unique ID 1724 based on, for example, its internal unique controller serial number. Unique ID 1724 may be correlated with a location identifier. For example, unique ID 1724 may correspond to Bedroom A or Laundry Room.

I/O device(s) 1701 may be configured to be in communication with controller 1710. I/O device(s) 1701 may include an infrared (IR) emitter 1704, a light sensor 1706, and one or more environmental sensors 1708. In some examples, I/O device(s) 201 may include IR emitter 1704.

In some examples, I/O device(s) 201 may include IR emitter 1704 and one or more of light sensor 1706 and environmental sensor(s) 1708.

Light sensor 1706 may be configured to detect a level of ambient light in a location of beacon 1604. Environment sensor(s) 1708 may be configured to detect one or more conditions at a location of beacon 1604, such as, but not limited to, temperature, humidity, air quality, gas levels, smoke levels, particulate levels, motion levels, and the like. IR emitter 1704 may be configured to emit a burst of infrared light as a carrier wave. For example, IR emitter 1704 may be configured to emit a burst of infrared light having a wavelength of about 850 nm. In another example, IR emitter 1704 may be configured to emit a burst of infrared light that has a range between about 1.8 m to about 7.6 m. Generally, the range of IR emitter 1704 may be adjusted during operation.

Processor 1714 may modulate the carrier wave emitted by IR emitter 1704 with at least unique ID 1724. In some embodiments, processor 1714 may further modulate the carrier wave of IR emitter 1704 with one or more of a value corresponding to an area in which beacon 1604 is located, a level of power source 1702, values of one or more environmental sensors 1708, a level of ambient light detected by light sensor 1706, value of its pulse frequency, and the like. Further, processor 1714 may control an intensity of the light emitted by IR emitter 1704. For example, processor 1714 may set an intensity of its respective IR emitter 1704 to one of low, medium, or high intensity.

The use of IR-based beacon(s) 1604 provides advantages with respect to accurate location tracking. This is because beacon(s) 1604 are able to accurately segment areas (e.g., rooms, hallways, etc.) through exact boundaries. Beacon(s) 1604 are able to do this through the intrinsic nature of IR emissions not being able to pass through walls. Further, the use of IR emitter 1704 (in communication with IR receiver 1754 of sensor 1606) allows for hardware components 1602 to implement line-of-sight technology, without the need for external GPS systems. As such, the present disclosure offers a more precise and effective tracking system compared to conventional tracking systems implementing RF triangulation, all without requiring prior mapping of indoor spaces or computing triangulation vectors.

In some embodiments, one or more I/O devices 1701 may aid in self-regulation of beacon 1604. For example, processor 1714 may regulate how often beacon 1604 emits IR light (e.g., periodically, at particular times, under particular conditions, etc.). In one embodiment, processor 1714 may regulate how often beacon 1604 emits IR light based on a level of ambient light measured by light sensor 1706. For example, processor 1714 may instruct IR emitter 1704 to emit light at a lower rate, responsive to a low level of ambient light, which may correspond to night-time or an uninhabited area. In another example, processor 1714 may slow a frequency at which IR emitter 1704 is instructed to emit light, based on a level of motion detected by one or more environmental sensors 1708. In yet another example, processor 1714 may slow a frequency at which IR emitter 1704 is instructed to emit light, based on a power level of power source 1702. in order to conserve power and extend the life of beacon 1604.

Referring back to FIG. 16, beacon(s) 1604 may be configured to be in communication with one or more sensors 1606. For example, beacon(s) 1604 may communicates with sensor(s) 1606 through the IR emissions emitted by beacon(s) 1604.

As discussed above, each sensor 1606 may be a wearable sensor apparatus. In one particular application, patients in an assisted living facility or a hospital may be equipped with sensor 1606 to track a location of the patient throughout the facility. Sensor 1606 may generally be positioned anywhere on a person's body, such that IR emissions can pass therethrough.

FIG. 17 illustrates a single sensor 1606, according to one embodiment. Each sensor 1606 may include a controller 1760 and one or more I/O devices 1761.

Controller 1760 may include a processor 1764, a memory 1766, a storage 1768, and a network interface 1770. Controller 1760 is coupled to one or more I/O devices 1761.

Processor 1764 retrieves and executes programming code 1771 (i.e., programming instructions) stored in memory 1766, as well as stores and retrieves application data. Processor 1764 is included to be representative of a single processor, multiple processors, a single processor having multiple processing cores and the like. Network interface 1770 may be any type of network communications allowing controller 1760 to communicate externally via a computing network.

Storage 1768 may be, for example, a disk drive storage device. Although shown as a single unit, storage 1768 may be a combination of fixed and/or removable storage devices, such as fixed disk drives, removable memory cards, optical storage, NAS, or SAN. As illustrated, storage 1768 may include a location history 1772 (also referred to herein as list of locations 1772). Location history 1772 may include a list of one or more previous (e.g., the last several) locations of sensor 1606.

I/O devices 1761 may be in communication with controller 1760. I/O devices 1761 may include an infrared (IR) receiver 1754, a radio-frequency (RF) emitter 1756, and an inertial measurement unit (IMU) 1758.

IR receiver 1754 may be configured to receive IR emissions. For example, IR receiver 1754 may be configured to receive IR emissions from IR emitter 1704 of beacon 1604. RF emitter 1756 may be configured to transmit an RF signal to a remote system. For example, RF emitter 1756 may be configured to transmit a packet of information via an RF signal to one or more communication hubs 1608 (FIG. 16). IMU 1758 may be configured to measure motion of a wearer of sensor 1606 (also referred to herein as a sensor wearer).

Memory 1766 may include programming code 1771, operating system (OS) 1773, boundary agent 1774, interference agent 1776, and data packet generator 1778. Program code 1771 may accessed by processor 1764 for processing (i.e., executing program instructions). Program code 1771 may include, for example, steps discussed below in conjunction with FIGS. 18-24. In a specific example, processor 1764 accesses program code 1771 to demodulate and parse an IR emission received by IR receiver 1754.

Boundary agent 1774 may be configured to determine whether a wearer of sensor 1606 has entered, or is about to enter, a restricted area. Boundary agent 1774 is discussed further below in conjunction with FIG. 24.

Interference agent 1776 may be configured to differentiate between a change in user location and interference, or intersection, between multiple IR emissions from multiple beacons 1604. Interference agent 1776 is discussed further below in conjunction with FIG. 19.

Data packet generator 1778 may be configured to generate a data packet for transmission to communication hub 1608, based on the modulated signal received from beacon 1604. For example, data packet generator 1778 may generate a data packet that includes unique ID 1724 of beacon 1604, location type, power level of beacon 1604, value(s) of one or more environmental sensors 1708, and pulse frequency. Sensor 1606 may transmit the data packet to communication hub 1608 via RF emitter 1756.

Although memory 1766 is shown as a single entity, memory 1766 may include one or more non-transitory memory devices having blocks of memory associated with physical addresses, such as RAM, ROM, flash memory, or other types of volatile and/or non-volatile memory.

Referring back to FIG. 16, sensor(s) 1606 may be in communication with communication hub(s) 1608 via one or more communication links 1640. In one embodiment, communication link 1640 represents RF communication between each sensor 1606 and each communication hub 1608. Communication hub 1608 may provide a gateway between on-site hardware components 1602 and an external system via network 1605. For example, computing environment 1600 may include management entity 1610, which may be in communication with on-site hardware components 1602 over network 1605 via communication hub(s) 1608.

As illustrated in FIG. 17, communication hub 1608 includes a controller 1740 and one or more I/O devices 1741.

Controller 1740 may include a processor 1734, a memory 1736, a storage 1738, and a network interface 1740. Controller 1740 is coupled to one or more I/O devices 1741.

Processor 1734 retrieves and executes programming code 1742 (i.e., programming instructions) stored in memory 1736, as well as stores and retrieves application data. Processor 1734 is included to be representative of a single processor, multiple processors, a single processor having multiple processing cores and the like. Network interface 1740 may be any type of network communications allowing controller 1740 to communicate externally via a computing network. For example, network interface 1740 allows controller 1740 to communicate externally with management entity 1610.

Storage 1738 may be, for example, a disk drive storage device. Although shown as a single unit, storage 1738 may be a combination of fixed and/or removable storage devices, such as fixed disk drives, removable memory cards, optical storage, NAS, or SAN.

I/O devices 1741 may be in communication with controller 1740. I/O devices 1741 may include a receiver 1742. Receiver 1742 is configured to receive RF signals emitted by RF emitter 1756 of sensor 1606.

Memory 1736 may include programming code 1742 and operating system (OS) 1744. Program code 1742 may accessed by processor 1734 for processing (i.e., executing program instructions). Program code 1742 may include, for example, steps discussed below in conjunction with FIGS. 18-24.

Although memory 1736 is shown as a single entity, memory 1736 may include one or more non-transitory memory devices having blocks of memory associated with physical addresses, such as RAM, ROM, flash memory, or other types of volatile and/or non-volatile memory.

Referring back to FIG. 16, computing environment 1600 may further include one or more client devices 1612, a database 1612, and a database 1634. In one embodiment, client device 1612 may be accessed by staff of the facility (i.e., users), such that staff members may be able to track wearers of sensors 1606 throughout the facility. Client device 1612 may be any computing device accessible by a user, such as, but not limited to, a computer, a mobile device, a tablet, and the like. Generally, client device 1612 may include components of a computing device, e.g., a processor, memory, a hard disk drive, one or more input and/or output devices, and the like. As illustrated, client device 1612 includes a web client (or mobile application) 1614.

Web client 1614 allows a user of client device 1612 to access a functionality of management entity 1610. For example, web client 1614 may access content managed by web client application server 1616 on management entity 1610. For example, web client 1614 allows access to content managed by, for example, CarePredict proprietary software. The content that is displayed to a user may be transmitted from web client application server 1616 to client device 1612, and subsequently processed by web client 1614 for display through a graphical user interface (GUI) (not shown) of the user's client device 1612.

In one example, the software accessed through web client 1614 allows users to set up their "enterprise" by, for example, adding facilities, floor plans of each facility, beacon 1604 placements, communication hub 1608 placements, staff listing, resident listing, restricted area definitions, restricted boundaries, and the like. In some embodiments, CarePredict software includes portals for both staff of the facility as well as residents of the facility (e.g., provide access to individual health plans).

Figure 29:
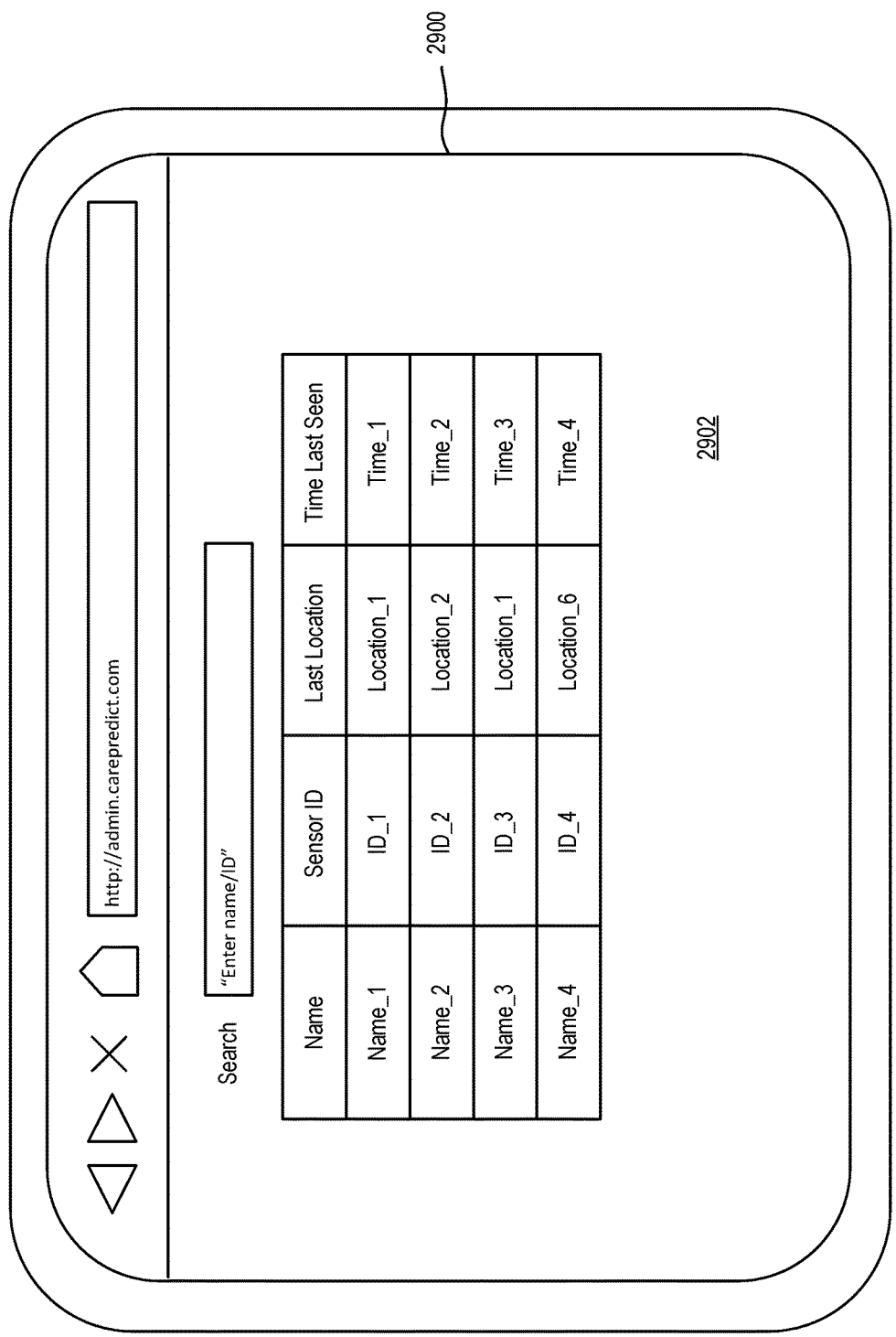
FIG. 29 is a block diagram of a screenshot of a software platform, according to one embodiment of the present disclosure.

FIG. 29 is an example screenshot 2900 of a webpage 2902 of software, according to one embodiment. As illustrated, webpage 2902 may include a matrix of information, such as, but not limited to name of a sensor wearer, unique ID of a sensor of the sensor wearer, last seen location of the sensor wearer, time of last seen location of the sensor wearer, and the like. Further, webpage 2902 may include a search bar that allows a user to search for a specific sensor wearer either by name or unique ID of their sensor.

Management entity 1610 is in communication with database 1622. For example, management entity 1610 may communicate with database 1622 via a local connection (e.g., SAN, NAS) or over the Internet (e.g., a cloud based storage service). Management entity 1610 may be configured to directly access data included in database 1622 and/or interface with a database manager (not shown) that is configured to manage data included within database 1622. In some embodiments, direct access to database 1622 via a client device 1612 may restricted. Thus, any requests for information from client device 1612 must pass through management entity 1610.

Database 1622 may include information associated with one or more facilities accessing the software platform. As illustrated, for each facility 1624, database 1622 may store sensor wearer information 1626, user (i.e., non-sensor wearer users such as staff) information 1627, beacon information 1630, and floor plan information 1632.

Sensor wearer information 1626 may include data directed to daily activity of the sensor wearer, one or more location restrictions for the sensor wearer (i.e., locations within facility 1624 that are off-limits to the sensor wearer), health information associated with the sensor wearer, and the like. As illustrated, sensor wearer information 1626 may include location history 1628. Location history 1628 maintains a list, which may be sorted periodically, of sensor wearer locations (over time) that are registered by sensor 1606.

User information 1627 may include login information for each user, privilege information (associated with the user) for each sensor wearer (e.g., patient information each user is able to view, personal information of each user, and the like).

Beacon information 1630 may include information associated with each beacon 1604 installed within facility 1624. For example, beacon information 1630 may include a list of locations of each beacon 1604, along with the unique ID 1724 and/or a serial number of each beacon 1604. In one example, a location of the beacon 1604 may be entered into database 1622 by placing a pin on a floor plan map contained in floor plan information 1632. Floor plan information 1632 may include one or more floor plans of facility 1624. For example, floor plan information 1632 may include the location of each sensor wearer's designated room, location(s) of beacon(s) 1604, location(s) of communication hub(s) 1608, any designated restricted areas, boundary and pre-boundary information (discussed below), and the like.

Because all client devices 1612 may not have direct access to database 1622, management entity 1610 may generate a relational database 1634 that may limit an amount of information accessible to certain users of client device(s) 1612. For example, a staff member of facility 1624 may access relational database 1634 via client device 1612, to find a current location, or previous location, of a sensor wearer. In this manner, pursuant to sensor 1606 and management entity 1610 detecting an emergency issue with a sensor wearer, a staff member can be alerted through their client device 1612, and subsequently, is able to access location information 1628 in relational database 1628 to locate the sensor wearer within the facility.

Figure 18:
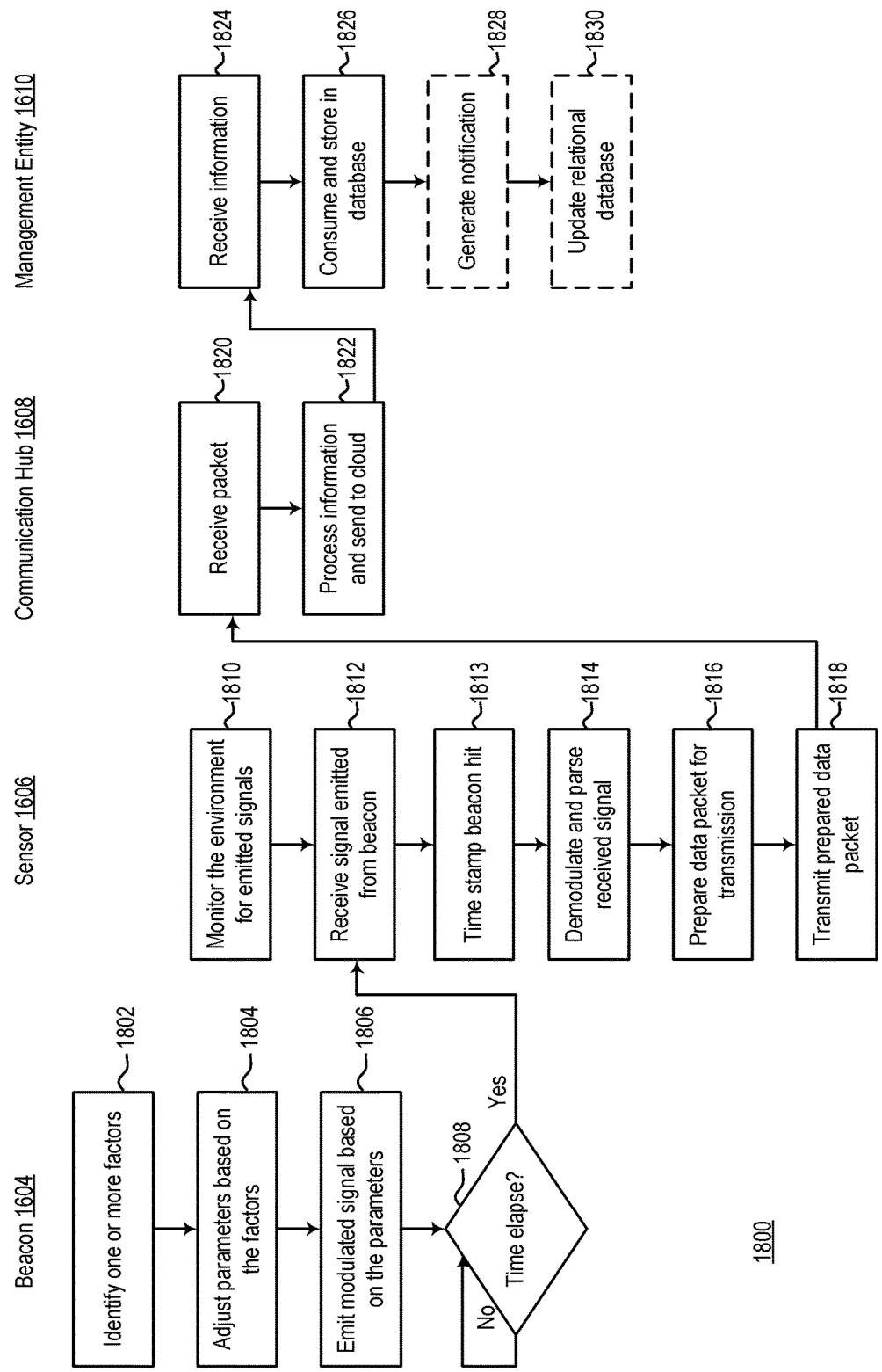
FIG. 18 is a flow chart illustrating an example simplified method of detecting a location of a sensor wearer, according to one embodiment of the present disclosure.

FIG. 18 is a flow diagram illustrating a simplified method 1800 of detecting a location of a sensor wearer, according to one embodiment. FIG. 18 illustrates the roles played by each of beacon 1604, sensor 1606, and communication hub 1608 in locating a sensor wearer.

At step 1802, beacon 1604 identifies one or more factors. For example, beacon 1604 may identify a level of ambient light via light sensor 1706 and one or more environmental values via one or more environmental sensors 1708. Processor 1714 of beacon 1604 adjusts parameters of the next IR emission (step 1804). For example, processor 1714 may modulate the emission based on one or more of the ambient light level, humidity level, temperature level, and the like. At step 1806, IR emitter 1704 of beacon 1604 emits a modulated IR emission based on the adjusted parameters. Additionally, the IR emission is further modulated to include unique ID 1724 of beacon 1604. At decision block 1808, processor 1714 determines whether a predetermined amount of time has elapsed. The predetermined amount of time is the amount of time between successive IR emissions. The frequency of IR emissions may be dynamically adjusted throughout the day based on, for example, a level of ambient light. If processor 1714 determines that the predetermined amount of time has not elapsed, method 1800 reverts to decision block 1808. If, however, processor 1714 determines that the predetermined amount of time has elapsed, method 1800 reverts to step 1802 (not shown in FIG. 18). Because IR signals do not pass through walls, beacons 1604 are able to segment rooms and hallways to exact boundaries.

While beacon 1604 periodically emits IR emissions, at step 1810, sensor 1606 continually monitors the environment for IR emissions from nearby beacons (i.e., beacons having IR emissions of sufficient signal strength that are detectable by sensor 1606). At step 1812, sensor 1606 is within range of beacon 1604 and receives the IR emission from beacon 1604. For example, sensor 1606 receives the IR emission from beacon 1604 via IR receiver 1754. At step 1813, sensor 1606 time-stamps the received IR emission. At step 1814, sensor 1606 demodulates and parses the received IR emission. For example, data packet generator 1778 demodulates the signal to parse the signal for information included therein, such as, for example, unique ID 1724 of beacon 1604, a power source level of beacon 1604, a level of ambient light, which may be indicative of a time of day, one or more environmental factors, and the like. Based on the information extracted from the demodulated IR emission, at step 1816, data packet generator 1778 generates a data packet to be transmitted to communication hub 1608. Generally, sensor 1606 can communicate with any communication hub 1608 that is within range. If there is greater than one communication hub 1608 within range, sensor 1606 determines and selects the communication hub 1608 with the strongest signal. Sensor 1606 then communicates with communication hub 1608 that has the strongest signal. At step 1818, sensor 1606 transmits the generated data packet to communication hub 1608. For example, sensor 1606 transmits the generated data packet to communication hub 1608 via RF emitter 1756.

At step 1820, communication hub 1608 receives the data packet from sensor 1606. In a particular embodiment, communication hub 1608 takes the received data packet and converts the data packet into a format that is easily understandable by management entity 1610. For example, communication hub 1608 may translate the received data packet into a JSON format (or any other suitable format). In general, communication hub 1608 may act as a gateway between sensor 1606 and management entity 1610. Communication hub 1608 processes the information in the data packet, and sends the information to management entity 1610 (step 1822).

At step 1824, management entity 1610 receives the information from communication hub 1608. At step 1826, management entity 1610 consumes the information and stores the information in database 1622. The information is then processed and filtered inside database 1622. In some (optional) embodiments, at step 1828, management entity 1610 generates a notification to push to client device(s) 1612, if management entity 1610 determines that the incoming information presents a critical alert. Additionally, in some (optional) embodiments, at step 1830, management entity 1610 may update database 1634, which includes selective information that may be accessed directly by users of client device(s) 1612.

Interference Techniques

Method 1800 illustrates a simplified version of a location detection process, in which a single sensor 1606 is in communication with a single beacon 1604 and a single communication hub 1608. In practice, however, a given sensor 1606 may interact with a plurality of signals emitted by a plurality of beacons 1604 within a facility, when sensor 1606 comes into proximity with beacons 1604. In some situations, multiple signals emitted by multiple beacons 1604 may intersect or interfere, such that a sensor 1606 receives two or more signals at a given moment. In this scenario, it may be difficult for sensor 1606 to accurately determine a location of a sensor wearer. More specifically, it may be difficult for sensor 1606 to determine a change in location of a sensor wearer.

Interference agent 1776 (FIG. 17) aids in more accurately determining a location, or a change in location, of a sensor wearer. Interference agent 1776 filters out beacon interference, such that sensor 1606 can report a proper location of the sensor wearer to communication hub 1608. As a result of sensor 1606 time-stamping each incoming IR emission, interference agent 1776 is able to maintain a history of the last several beacons (e.g., last four beacons 1604) that sensor 1606 has received an IR emission from. The running history aids in helping interference agent 1776 determine whether the sensor wearer has moved to a new location or whether there is interference between signals of two or more beacons 1604.

In one embodiment, to validate a change in sensor wearer location, sensor 1606 maintains a running tally of an amount of consecutive IR emissions received from a given beacon 1604. For example, to validate a change in sensor wearer location, sensor 1606 may receive at least ten consecutive IR emissions in succession from a "new" beacon 1604, while not receiving an IR emission from beacon 1604 that is the "current" beacon 1604. In other words, sensor 1606 validates a change of location by determining a current location of sensor wearer; by referencing a most recently recorded location in the history, and counting an amount of successive IR emissions received from a "new" beacon 1604 that is in a location that is different than the current location. Sensor 1606 may confirm that the sensor wearer is in a new location when the successive IR emissions count exceeds a threshold.

In another embodiment, to validate a change in sensor wearer location, sensor 1606 maintains a timer beginning from a last received IR emission from a given beacon 1604. For example, to validate a change in sensor wearer location, sensor 1606 starts a timer from the last IR emission from a given beacon 1604 until another emission from that same beacon 1604 is received. If the timer exceeds a threshold amount of time (e.g., five minutes), sensor 1606 disregards IR emission from the given beacon 1604, and does not update the history with a change in location.

In yet another embodiment, to validate change in sensor wearer location, sensor 1606 maintains a zonal history. Sensor 1606 has not received an IR signal from the last beacon 1604 that was reported to communication hub 1608, but sensor 1606 continues to filter beacons 1604 that already exist in the zonal history. This zonal history is used to keep track of when the filtering occurs for more than a predetermined amount of time (e.g., two minutes). All the rooms that are sensed for more than a predetermined amount of time are cleared from the zonal history list. This allows the system to report only new location changes.

Figure 19A:
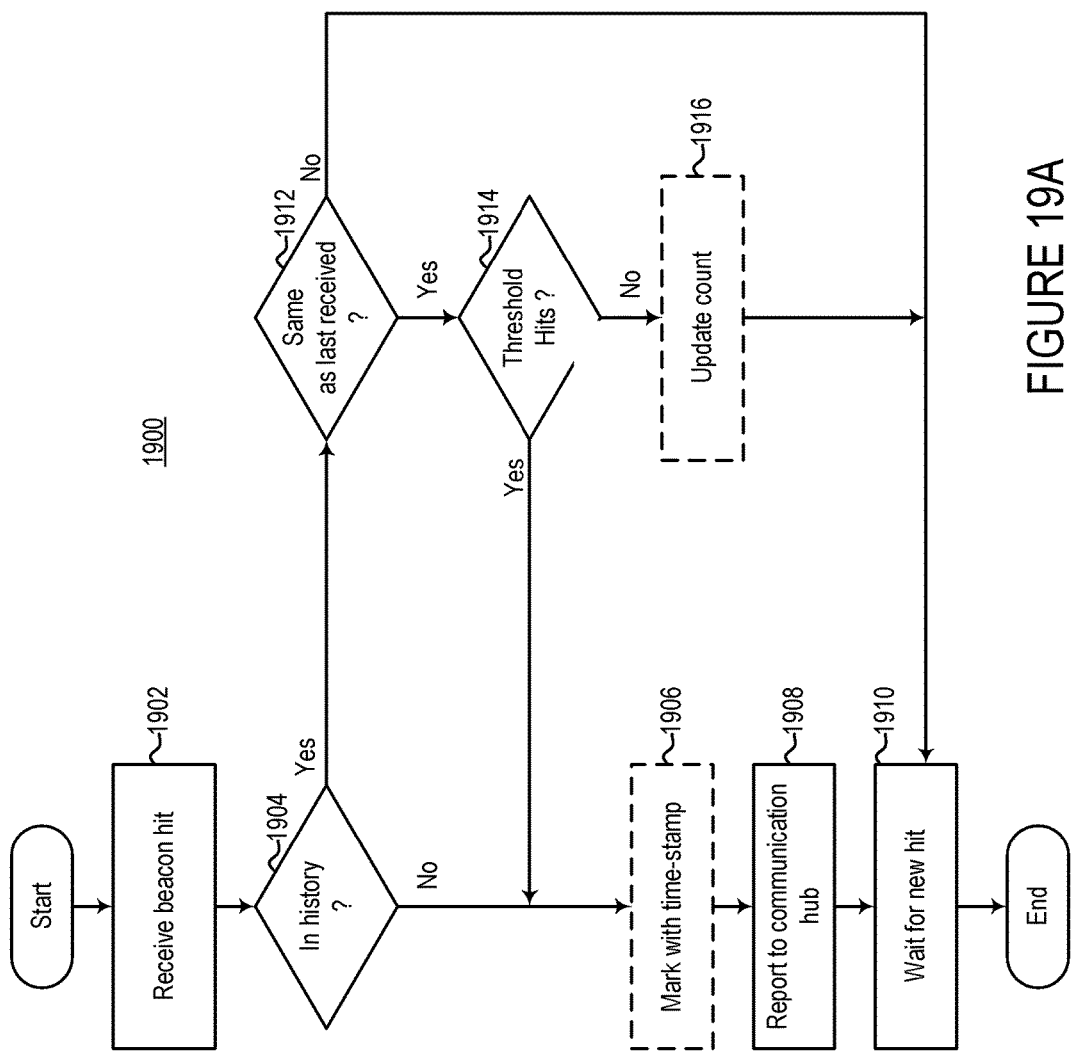
FIG. 19A is a flow chart illustrating an example method of validating a change of location of a sensor wearer, according to one embodiment of the present disclosure.

FIG. 19A is a flow diagram illustrating a method 1900 of validating a change of location of a sensor wearer, according to one embodiment. Method 1900 begins at step 1902 when sensor 1606 receives an IR emission from one beacon 1604, beacon A. At step 1904, interference agent 1776 determines whether beacon A is present in the running history of beacons hit. For example, as stated above, sensor 1606 maintains a list of locations 1772 in storage 1768. In some embodiments, the list of locations 1772 includes the last several (e.g., four) beacons 1604 for which sensor 1606 recorded a beacon hit. If beacon A is not present in the running history of beacon hits, interference agent 1776 records beacon A in list of locations 1772 (step 1906). In some embodiments, interference agent 1776 marks beacon A with a time-stamp.

For example, Table 1, provided below, illustrates an example list of locations 1772 that may be generated over time.

TABLE 1

| Time (secs) | Beacon ID | $LH_{01}$ | $LH_{02}$ | $LH_{03}$ | Backend | Room Change | Reason |
|---|---|---|---|---|---|---|---|
| 00 | A | A | X | X | A | True | New Room |
| 02 | B | B | A | X | B | True | New Room |
| 04 | C | C | B | A | C | True | New Room |
| 06 | B | C | B | A | C | False | Filtered, room present in history |
| 08 | B | C | B | A | C | False | Filtered |
| 10 | B | C | B | A | C | False | Filtered |
| 12 | B | C | B | A | C | False | Filtered |
| 14 | B | C | B | A | C | False | Filtered |
| 16 | B | C | B | A | C | False | Filtered |
| 18 | B | C | B | A | C | False | Filtered |
| 20 | B | C | B | A | C | False | Filtered |
| 22 | B | C | B | A | C | False | Filtered |
| 24 | B | C | B | A | C | False | Filtered |
| 26 | B | B | C | A | B | True | Counter check succeeded |

As shown in Table 1, there are several columns: Time (sec), Beacon ID, Latched History ($LH_{01}$), $LH_{02}$, $LH_{03}$, Backend, Room Change, and Reason. The Time column denotes that time that the sensor 1606 received the IR emission from beacon 1604. The Beacon ID column denotes the ID of beacon 1604 that emitted the IR emission received by sensor 1606. The $LH_{01}$ column denotes the ID of the last beacon 1604 that was seen. The $LH_{02}$ column denotes the ID of the second to last beacon 1604 that was seen. The $LH_{03}$ column denotes the ID of the third to last beacon 1604 that was seen. Collectively, $LH_{01}$, $LH_{02}$, and $LH_{03}$ may define the "running history" of the last several beacon hits, recited above in conjunction with step 1904. One of ordinary skill in the art could imagine that the running history, or latched history, could span several more recordings. Three most recent beacon IDs are not meant to be limiting. The Backend column denotes the last beacon hit that was reported by sensor 1606 to communication hub 1608. The Room Change column denotes whether the received beacon hit denotes a Room Change. The entries in the Room Change column, is Boolean (i.e., two values, typically true or false). The Reason column is illustrated in Table I for illustrative purposes only. The Reason column provides a brief explanation for the reader as to why a beacon hit was not transmitted to communication hub 1608 by sensor 1606.

Continuing with the above example, sensor 1606 receives a beacon hit from Beacon A at time $t_{00}$. Interference agent 1776 determines whether Beacon A is present in the latched history. Because Interference agent 1776 determines that Beacon A is not present in the history, interference agent 1776 reports the beacon hit to communication hub (step 1908). At time $t_{02}$, interference agent 1776 receives a beacon hit from Beacon B. Interference agent 1776 determines that Beacon B is not present in latched history. Accordingly, interference agent 1776 does not filter the beacon hit from Beacon B, and sensor 1606 reports the beacon hit to communication hub 1608. At time $t_{04}$, sensor receives a beacon hit from Beacon C. Interference agent 1776 determines that Beacon C is not present in latched history. Accordingly, interference agent 1776 does not filter the beacon hit from Beacon C, and sensor 1606 reports the beacon hit to communication hub 1608.

If, however, interference agent 1776 determines that the received beacon hit is present within latched history, interference agent 1776 determines whether received beacon hit is the same beacon as the last previously recorded beacon. For example, continuing with the discussion of Table I, at time $t_{06}$, sensor 1606 receives a beacon hit from Beacon B. Interference agent 1776 references latched history, and determines that Beacon B is present in latched history (i.e., $LH_{02}$). Because Beacon B is present in latched history, interference agent 1776 determines whether Beacon B is the same beacon that emitted the previous beacon hit. As illustrated, the prior beacon hit was emitted from Beacon C. Thus, Beacon B is not the same as the previously received beacon hit.

If interference agent 1776 determines that the received beacon hit is not from the same beacon 1604 as the previously received beacon hit (i.e., Beacon B instead of Beacon C), method 1900 proceeds to step 1910, and sensor 1606 waits for a new beacon hit.

If, however, at step 1910, interference agent 1776 determines that received beacon hit is from the same beacon as the previously received beacon hit, then, at step 1914, interference agent 1776 determines whether sensor 1606 recorded a (predefined) threshold number of consecutive beacon hits from that same beacon. In some embodiments, the threshold number of consecutive beacon hits can range from 2 to 15 consecutive hits. In other embodiments, the threshold number of consecutive beacon hits exceeds 15 consecutive hits. If the threshold number of consecutive beacon hits is not met, then at step 1916, interference agent 1776 updates a count of a number of consecutive beacon hits, and method 1900 proceeds to step 1920, as the sensor 1606 waits for a new beacon hit.

In some embodiments, interference agent 1776 may maintain a counter of consecutive hits for a given beacon, after recording a first beacon hit. The counter for the given beacon is cleared once a hit for a different beacon is recorded. If, at step 1912, interference agent 1776 determines that sensor 1606 has not recorded a threshold amount of consecutive beacon A hits, at step 1914, interference agent 1776 updates beacon A's counter, and sensor 1606 waits for a new beacon hit (step 1916).

For example, at time $t_{08}$, sensor 1606 receives a beacon hit from Beacon B. Interference agent 1776 determines that the current beacon hit is from the same beacon as the previously received beacon hit (at time $t_{06}$). For purposes of this example, the threshold number of consecutive beacon hits is 10. Because this is only the first consecutive beacon hit received from Beacon B, the threshold is not met. Interference agent 1776 filters the beacon hit, and sensory 1606 does not report the beacon hit to communication hub 1608.

If, however, at step 1914, interference agent 1776 determines that the threshold amount of consecutive beacon hits has been met, then method 1900 proceeds to step 1908, and the beacon hit is reported to communication hub 1608.

For example, at times, $t_{10}$, $t_{12}$, $t_{14}$, $t_{16}$, $t_{18}$, $t_{20}$, $t_{22}$, and $t_{24}$, interference agent 1776 determine that the threshold amount of consecutive beacon hits has not been met, and therefore filtered the beacon hit. At time, $t_{26}$, however, interference agent 1776 determines that sensor 1606 has received ten consecutive beacon hits from Beacon B. Therefore, interference agent 1776 does not filter the beacon hit, and sensor 1606 reports the beacon hit to communication hub 1608.

Waiting until a threshold number of consecutive beacon hits from a given beacon 1604 before reporting to the communication hub 1608 provides for a more accurate determination of whether a sensor wearer has moved locations to a new room. Those skilled in the art could imagine a scenario in which a sensor wearer moves between Room A (with Beacon A) and Room B (with Beacon B) in constant succession. Further, those skilled in the art could imagine a scenario where a sensor wearer temporarily moves back to Room A for an item, and returns to Room B.

Figure 19B:
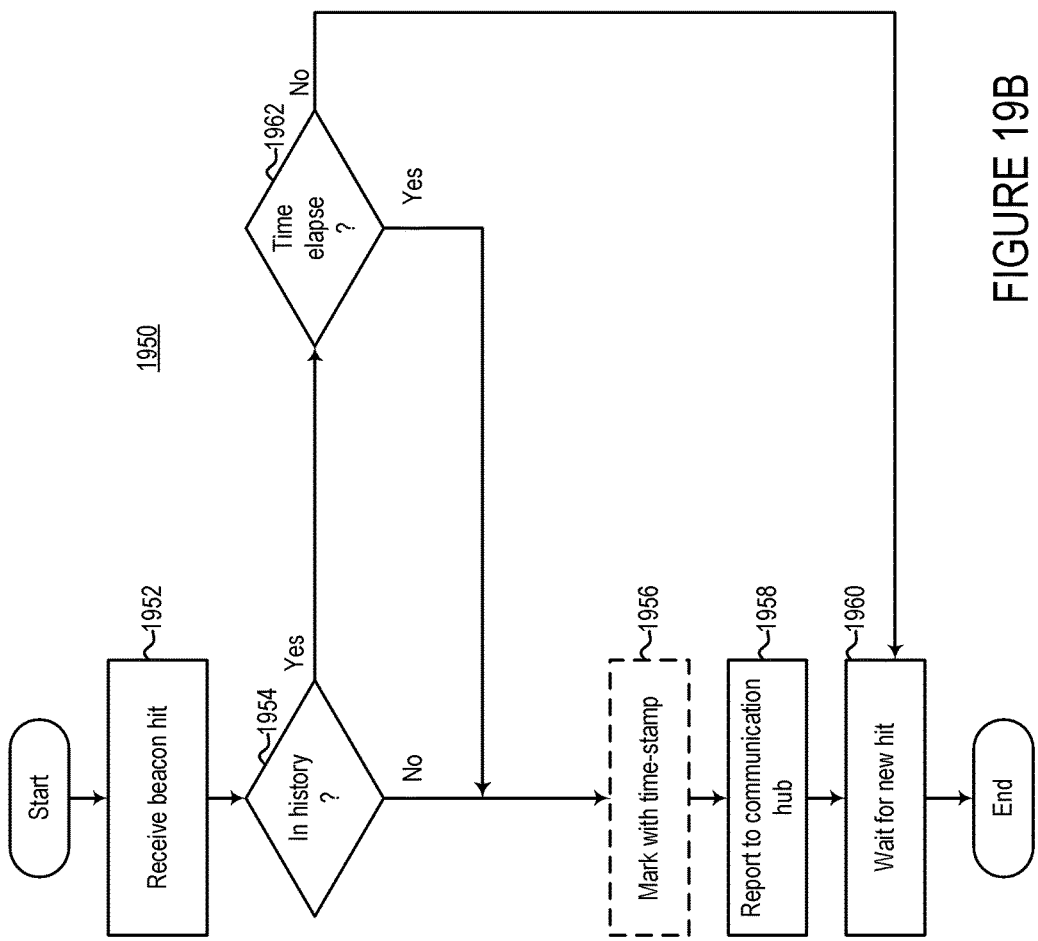
FIG. 19B is a flow chart illustrating an example method of validating a change of location of a sensor wearer, according to one embodiment of the present disclosure.

FIG. 19B is a flow diagram illustrating a method 1950 of validating a change of location of a sensor wearer, according to one embodiment. Method 1950 begins at step 1952 when sensor 1606 receives an IR emission from one beacon 1604, beacon A. At step 1954, interference agent 1776 determines whether beacon A is present in the running history of beacons hit. For example, as stated above, sensor 1606 maintains a list of locations 1772 in storage 1768. In some embodiments, the list of locations 1772 includes the last several (e.g., four) beacons 1604 for which sensor 1606 recorded a beacon hit. This subset of locations may be referred to as a "latched history." If beacon A is not present in the running history of beacon hits, interference agent 1776 records beacon A to communication hub 1608 (step 1958). In some embodiments, interference agent 1776 marks beacon A with a time-stamp (step 1956).

For example, Table 1, provided below, illustrates an example list of locations 1772 that may be generated over time. Table 2 has the same column types as Table 1.

TABLE 2

| Time (secs) | Beacon ID | $LH_{01}$ | $LH_{02}$ | $LH_{03}$ | Room Backend | Change | Reason |
|---|---|---|---|---|---|---|---|
| 00 | A | A | X | X | A | True | New Room |
| 02 | B | B | A | X | B | True | New Room |
| 04 | C | C | B | A | C | True | New Room |
| 06 | C | C | B | A | C | False | — |
| 08 | C | C | B | A | C | False | — |
| 10 | C | C | B | A | C | False | — |
| ... | | | | | | | |
| 294 | C | C | B | A | C | False | — |
| 296 | C | C | B | A | C | False | — |
| 298 | C | C | B | A | C | False | — |
| 300 | C | C | B | A | C | False | — |
| 302 | C | C | B | A | C | False | — |
| 304 | C | C | B | A | C | False | — |
| 306 | B | B | C | A | B | True | Timer expiry |

Using the information in Table 2, sensor 1606 receives a beacon hit from Beacon A at time $t_{00}$. Interference agent 1776 determines whether Beacon A is present in the latched history. Because Interference agent 1776 determines that Beacon A is not present in the history, interference agent 1776 reports the beacon hit to communication hub (step 1958). At time $t_{02}$, interference agent 1776 receives a beacon hit from Beacon B. Interference agent 1776 determines that Beacon B is not present in latched history. Accordingly, interference agent 1776 does not filter the beacon hit from Beacon B, and sensor 1606 reports the beacon hit to communication hub 1608. At time $t_{04}$, sensor receives a beacon hit from Beacon C. Interference agent 1776 determines that Beacon C is not present in latched history. Accordingly, interference agent 1776 does not filter the beacon hit from Beacon C, and sensor 1606 reports the beacon hit to communication hub 1608.

If, however, interference agent 1776 determines that the received beacon hit is present within latched history, interference agent 1776 determines whether the received beacon hit is from the same beacon as the previously received beacon hit (step 1962). If the received beacon hit is from the same beacon 1604 as the previously received beacon hit, then method 1950 proceeds to step 1960. If, however, interference agent 1776 determines that the received beacon hit is different from the previously received beacon hit, at step 1964, interference agent 1776 determines whether a threshold (pre-determined) amount of time has elapsed from the previously reported beacon hit from Beacon B. If the threshold amount of time has not elapsed, interference agent 1776 filters the beacon hit, and the method 1950 proceeds to step 1960. If the threshold amount of time has elapsed, interference agent 1776 does not filter the beacon hit, and sensor 1606 reports the beacon hit to communication hub 1608 (step 1958).

For example, at time $t_{06}$, sensor 1606 receives a beacon hit from Beacon C. Interference agent 1776 determines that Beacon C is in the latched history ($LH_{01}$). Further, interference agent 1776 determines that Beacon C is also the last beacon from which sensor 1606 received a beacon hit. Therefore, interference agent 1776 filters the beacon hit received at time, $t_{06}$. Still further, for times $t_{08}$-$t_{304}$, sensor 1606 only receives beacon hits from Beacon C.

At time $t_{306}$, sensor 1606 receives a beacon hit from Beacon B. Interference agent 1776 determines that Beacon B is in the latched history ($LH_{02}$). Further, interference agent 1776 determines that greater than five minutes (threshold amount) has passed since last receiving a beacon hit from Beacon B. Accordingly, interference agent 1776 does not filter the beacon hit, and sensor 1606 reports the beacon hit to communication hub 1608.

Both methods 1900 and 1950 repeat for each new beacon hit. Although FIG. 19A and FIG. 19B illustrate two separate validation techniques (e.g., tally-based, time-based), those skilled in the art could readily understand that each validation technique may be performed in conjunction.

Figure 20:
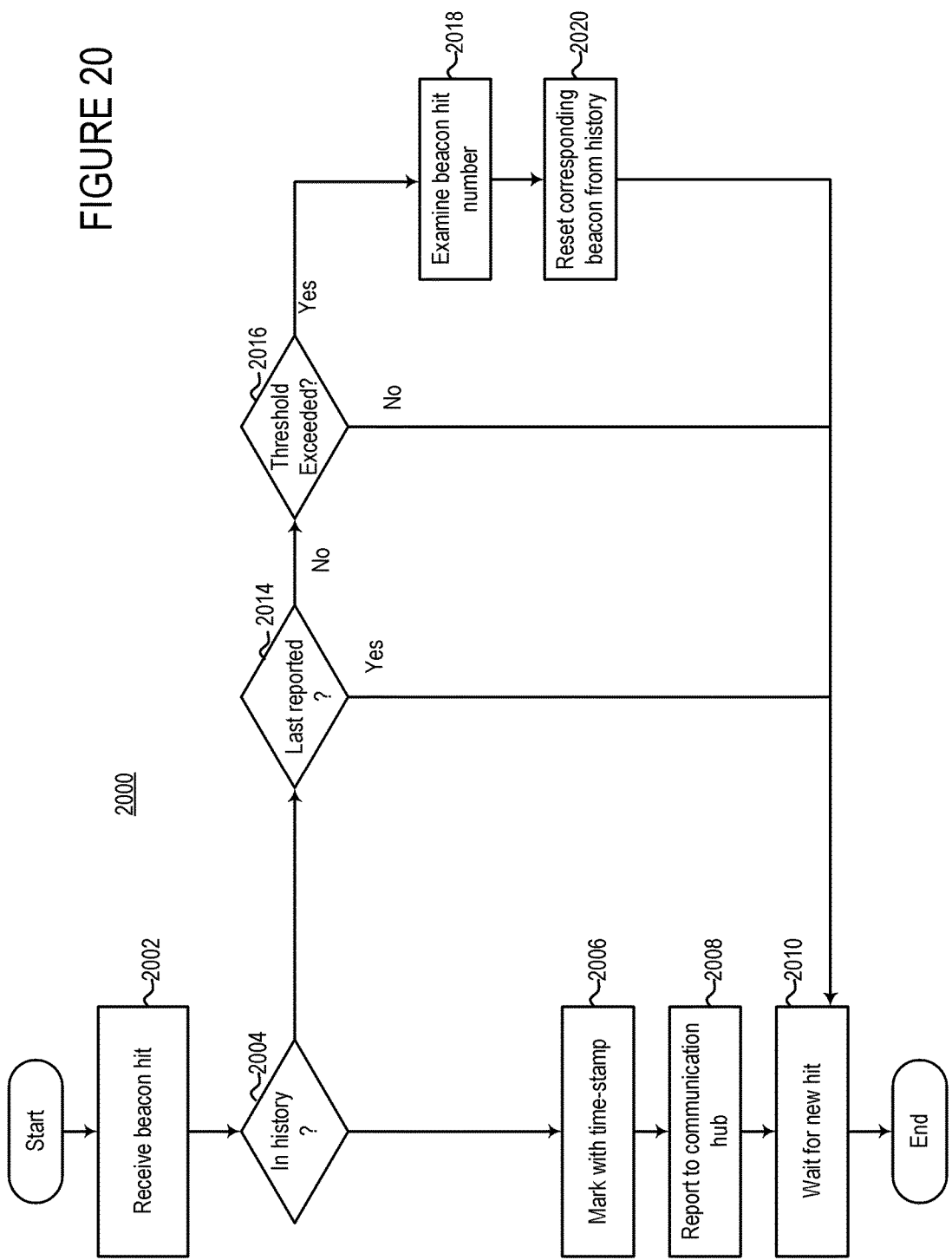
FIG. 20 is a flow chart illustrating an example method of validating a change of location of a sensor wearer, according to one embodiment of the present disclosure.

In some embodiments, interference agent 1776 may perform a zonal validation technique to determine a change in location. For example, FIG. 20 is a flow diagram illustrating a method 2000 of validating a change of location of a sensor wearer, according to one embodiment. Method 2000 begins at step 2002 when sensor 1606 receives an IR emission from one beacon 1604 (e.g., Beacon A). At step 2004, interference agent 1776 determines whether Beacon A is present in the running history of beacons hit. For example, as stated above, sensor 1606 maintains a list of locations 1772 in storage 1768. In some embodiments, the list of locations 1772 includes the last several (e.g., four) beacons 1604 for which sensor 1606 recorded a beacon hit. This subset of locations may be referred to as a "latched history." If Beacon A is not present in the running history of beacon hits, interference agent 1776 records beacon A to communication hub 1608 (step 2008). In some embodiments, interference agent 1776 marks beacon A with a time-stamp (step 2006).

For example, Table 3, provided below, illustrates an example list of locations 1772 that may be generated over time. Table 3 has the same column types as Table 1 and Table 2.

Table 3

| Time (secs) | Beacon ID | $LH_{01}$ | $LH_{02}$ | $LH_{03}$ | Backend | Change | Reason |
|---|---|---|---|---|---|---|---|
| 00 | A | A | X | X | A | True | New Room |
| 02 | B | B | A | X | B | True | New Room |
| 04 | C | C | B | A | C | True | New Room |
| 06 | B | C | B | A | C | False | Filtered |
| 08 | A | C | B | A | C | False | Filtered |
| 10 | B | C | B | A | C | False | Filtered |
| 12 | A | C | B | A | C | False | Filtered |
| ... | | | | | | | |
| 220 | B | C | B | A | C | False | Filtered |
| 222 | A | C | B | A | C | False | Filtered |
| 224 | B | C | B | A | C | False | Filtered |
| 226 | A | C | B | A | C | False | Filtered |
| 228 | B | C | X | X | C | False | (Zonal change cleared History) |
| 230 | A | A | C | X | A | True | New room |
| 232 | B | B | A | C | B | True | New room |
| 234 | A | B | A | C | B | False | Filtered |

Using the information in Table 3, sensor 1606 receives a beacon hit from Beacon A at time $t_{00}$. Interference agent 1776 determines whether Beacon A is present in the latched history. Because Interference agent 1776 determines that Beacon A is not present in the history, interference agent 1776 reports the beacon hit to communication hub (step 2008). At time $t_{02}$, interference agent 1776 receives a beacon hit from Beacon B. Interference agent 1776 determines that Beacon B is not present in latched history. Accordingly, interference agent 1776 does not filter the beacon hit from Beacon B, and sensor 1606 reports the beacon hit to communication hub 1608. At time $t_{04}$, sensor receives a beacon hit from Beacon C. Interference agent 1776 determines that Beacon C is not present in latched history. Accordingly, interference agent 1776 does not filter the beacon hit from Beacon C, and sensor 1606 reports the beacon hit to communication hub 1608.

If, however, interference agent 1776 determines that the received beacon hit is present within latched history, interference agent 1776 determines whether the received beacon hit is from the same beacon as the previously received beacon hit (step 2014). If the received beacon hit is from the same beacon 1604 as the previously received beacon hit, then method 1950 proceeds to step 1960. If, however, interference agent 1776 determines that the received beacon hit is different from the previously received beacon hit, at step 2016, interference agent 1776 determines whether a threshold (pre-determined) amount of time has elapsed from the previously reported beacon hit from Beacon C.

Using the above example, from times $t_{06}$ to time $t_{228}$, sensor has moved between Beacon A and Beacon B, and did not record a beacon hit from the last previously reported beacon (Beacon C). Interference agent 1776 determines whether a threshold amount of time has elapsed from the previously reported beacon hit at time $t_{04}$.

If the pre-determined amount of time has not elapsed from the previously reported beacon hit, method 2000 proceeds to step 2010, and sensor 1606 waits for a new beacon hit. If, however, the pre-determined amount of time has elapsed from the previously reported beacon hit, at step 2018 interference agent 1776 examines the beacon hits. For example, interference agent 1776 examines each beacon hit to identify those beacons that were seen above a threshold amount of time (e.g., 90 seconds). Referring to the above example, interference agent 1776 would identify that Beacon A and Beacon B were seen above the threshold amount of time.

At step 2020, interference agent 1776 resets the latched history. For example, interference agent 1776 resets the latched history to no longer include Beacon A and Beacon B. Method 2000 then proceeds to step 2010.

Continuing with the above example, at time $t_{228}$, interference agent resets the latched history. Thus, at time $t_{230}$, when sensor 1606 receives a hit from Beacon A, Beacon A is no longer in the latched history. Accordingly, sensor 1606 reports the hit from Beacon A to communication hub 1608. Similarly, at time $t_{232}$, when sensor 1606 receives a hit from Beacon B, Beacon B is no longer in latched history. Accordingly, sensor 1606 reports the hit from Beacon B to communication hub 1608.

In some embodiments, prior to validation techniques, interference agent 1776 performs a motion based filtering technique. The motion based filtering technique limits an amount of times that interference agent 1776 needs to perform the validation techniques. For example, interference agent 1776 may only perform the above validation techniques if interference agent 1776 determines that sensor 1776 has actually moved. Interference agent 1776 may leverage IMU 1758 to detect a physical movement of sensor 1606, which corresponds to a movement of a sensor wearer.

In some embodiments, responsive to interference agent 1776 determining that IMU 1758 records an movement reading below a threshold amount, interference agent 1776 communicates with processor 1764 to set sensor 1606 into a "low-power mode." In the low-power mode, IR scanning may cease for a given period of time (e.g., 30 seconds). IMU 1758 may further classify motion of the sensor wearer. For example, IMU 1758 may classify motion of the sensor wearer into one of the following categories: standing, walking, left turn, right turn. Thus, interference agent 1776 may determine that sensor wearer is in motion responsive to IMU 1758 classifying the motion into any of the above categories.

Figure 21:
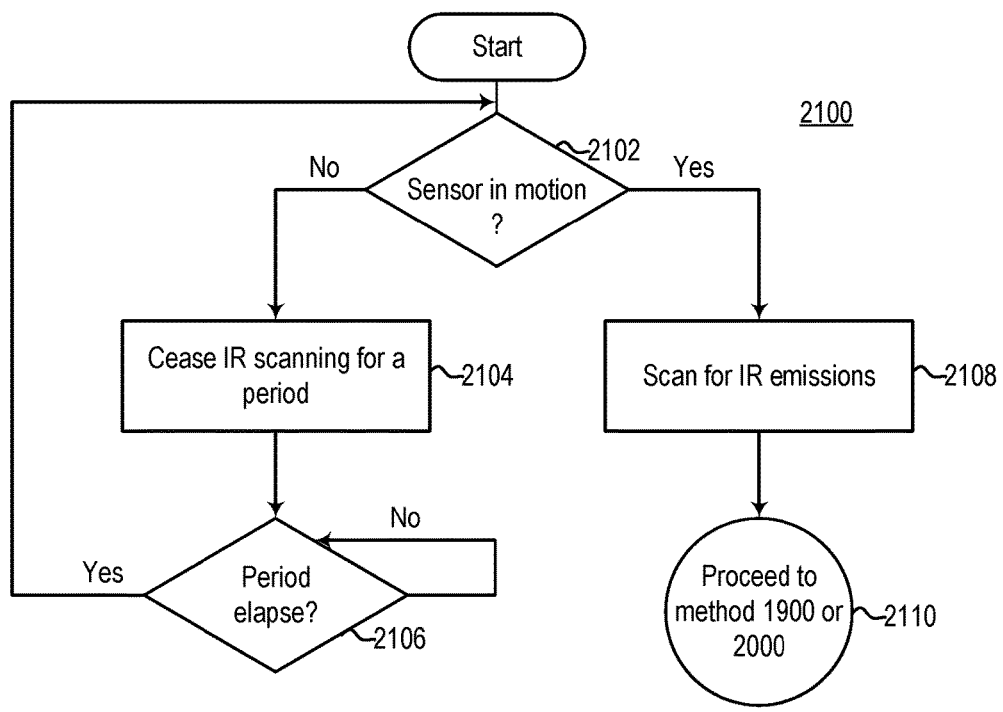
FIG. 21 is a flow chart illustrating an example method of performing a motion based filtering technique prior to validating a change of location of a sensor wearer, according to one embodiment of the present disclosure.

FIG. 21 is a flow diagram illustrating a method 2100 of performing a motion based filtering technique prior to validating a change of location of a sensor wearer, according to one embodiment. Method 2100 begins at step 2102 when interference agent 1776 determines whether sensor 1606 is in motion. For example, interference agent 1776 determines whether sensor 1606 is in motion by leveraging IMU 1758, to determine whether sensor 1606 undergoes a movement exceeds a threshold amount.

If interference agent 1776 determines that sensor 1606 is not in motion, step 2102 proceeds to step 2104. At step 2104, processor 1764 ceases IR scanning for a given period of time (e.g., 30 seconds). For example, if interference agent 1776 determines that IMU 1758 recorded a movement reading below a threshold amount (e.g., 85 mG-forces), then interference agent 1776 communicates with processor 1764 to cease IR scanning for a given period of time. At step 2106, processor 1764 determines whether the period of time has elapsed. Once the period of time has elapsed, step 2106 reverts to step 2102.

If, however, interference agent 17760 determines that the sensor 1606 is in motion, step 2102 proceeds to step 2108. At step 2107, sensor 1606 continues scanning for IR emissions. Step 2108 proceeds to step 2110, and sensor 1606 proceeds to any of methods 1900 (FIG. 19) or 2000 (FIG. 20) for validation techniques.

Boundary Monitoring Techniques

Accurately determining a location of a sensor wearer through filtering techniques discussed above, aids in accurately tracking a sensor wearer throughout the facility. Thus, it can be accurately determined when a sensor wearer approaches or enters a restricted location within the facility.

Boundary agent 1774 (FIG. 17) aids in notifying staff of a facility when a sensor wearer is approaching or entering a restricted location. As previously discussed, beacons 1604 are placed throughout a facility. Through web client 1614, staff and/or administrators of the facility may set restrictions on certain sensor wearers and/or generally define certain beacons 1604 as boundary beacons or pre-boundary beacons. Boundary beacons may generally be defined as beacons 1604 that are located on a boundary of a restricted area. Pre-boundary beacons may generally be defined as those beacons 1604 that are in close proximity to boundary beacons. In other words, pre-boundary beacons notify staff of a sensor wearer approaching a boundary beacon, such that measures can be taken to locate the sensor wearer before the sensor wearer reaches the boundary beacon.

Figure 22:
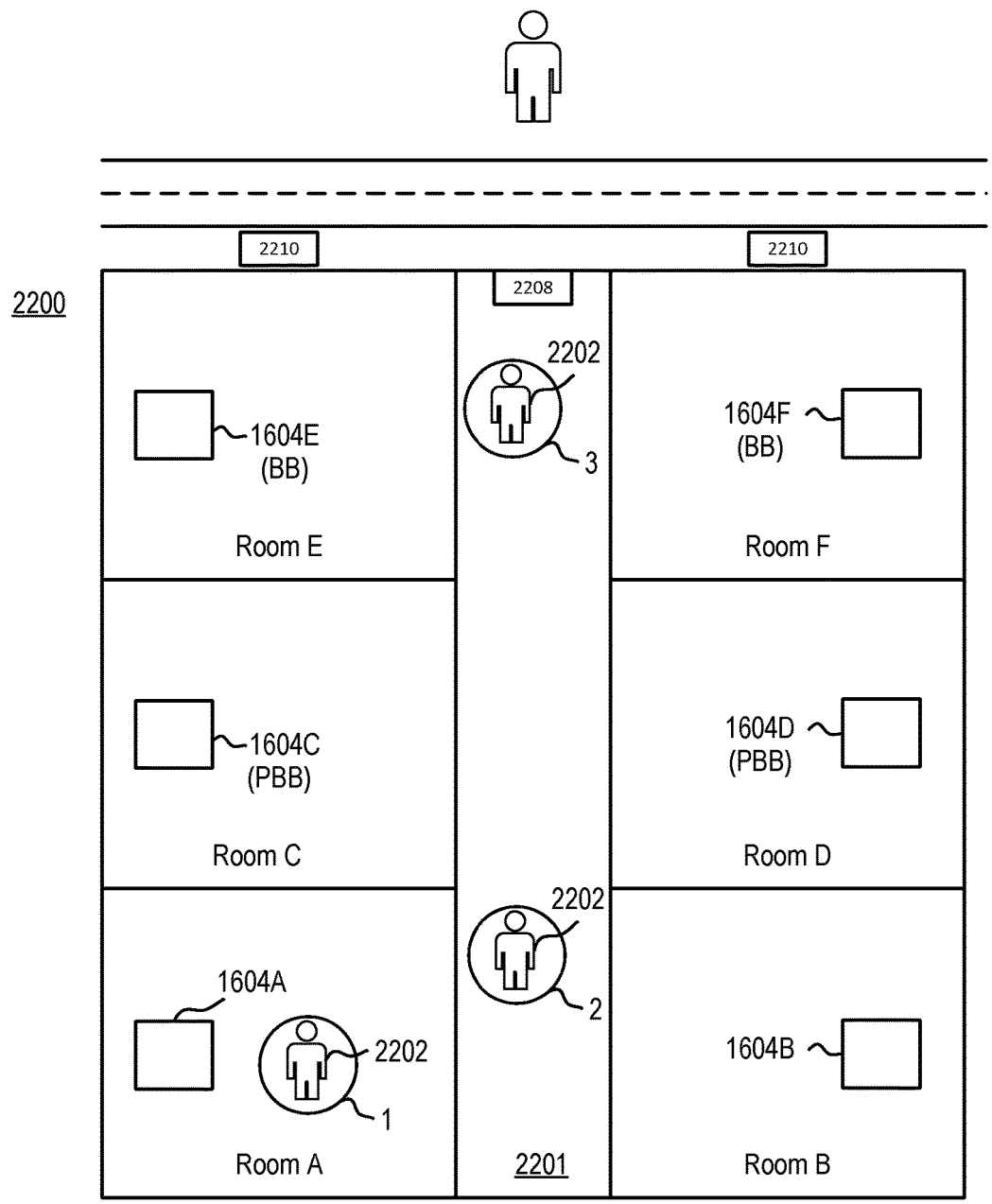
FIG. 22 is an example floor plan of a space, according to one embodiment disclosed herein.

FIG. 22 illustrates an example floorplan 2200 of a facility, according to one example. Floorplan 2200 includes a plurality of rooms: Room A, Room B, Room C, Room D, Room E, and Room F. In each room is a respective beacon 1604. For example, Room A includes beacon 1604A, Room B includes beacon 1604B, Room C includes beacon 1604C, Room D includes beacon 1604D, Room E includes beacon 1604E, and Room F includes beacon 1604F. Beacon 1604C and Beacon 1604D are designated as pre-boundary beacons (PBBs). Beacon 1604E and beacon 1604F are designated as boundary beacons (BBs).

Sensor wearer 2202 is illustrated in Location 1 in Room A. In Room A, sensor 1606 of sensor wearer 2202 receives IR emissions from beacon 1604A. When sensor wearer 2202 moves from Location 1 to Location 2 between Room E and Room F, sensor wearer 2202 would have passed Room C and Room D. Sensor 1606 of sensor wearer 2202 received IR emissions from both beacon 1606C and beacon 1606D when passing by those rooms. Both beacon 1606C and beacon 1606D are pre-boundary beacons. At Location 3 outside of facility 2201, sensor 1606 of sensor wearer is no longer in range of any beacons 1604. Sensor 1606 of the sensor wearer passed, however, beacon 1604E and beacon 1604F, which are both boundary beacons. As sensor wearer 2202 passes the pre-boundary beacons (PBBs) and the boundary beacons (BBs), an alarm may be triggered. In some embodiments, a boundary beacon (BB) may be placed on exterior door 2208.

Further, in some embodiments, floorplan 2200 includes one or more exterior beacons 2210. One or more exterior beacons 2210 periodically emit IR emissions. Beacons 2210 are used as a back-up device to correctly determine if sensor wearer has left the facility.

Figure 23:
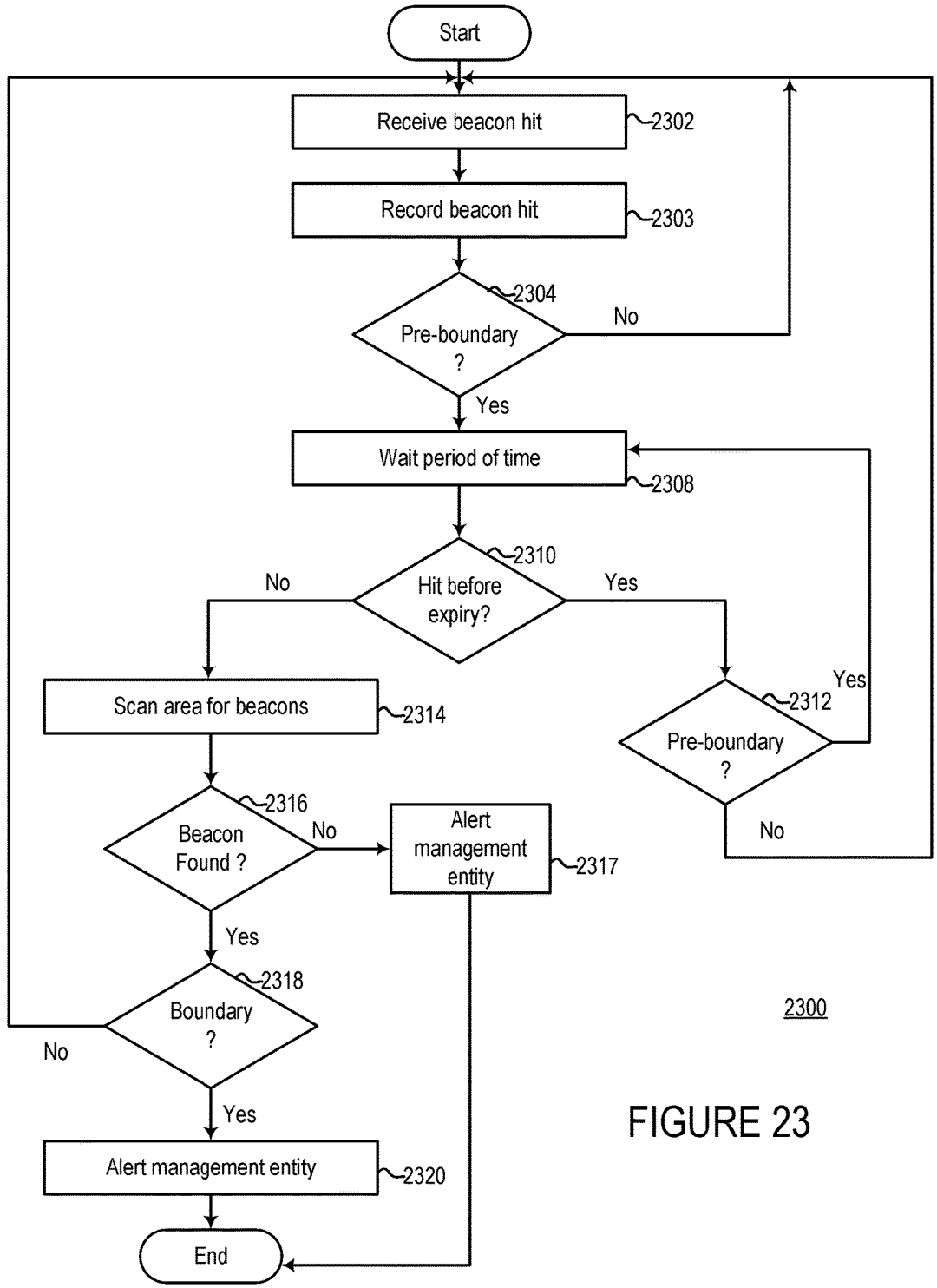
FIG. 23 is a flow chart illustrating an example method of detecting a location of a sensor wearer, according to one embodiment of the present disclosure.

FIG. 23 is a flow diagram of a method 2300 of locating a sensor wearer in a facility, according to one embodiment. Method 2300 begins at step 2302. At step 2302, sensor 1606 receives a first beacon hit from a first beacon. At step 2304, sensor 1606 determines whether the first beacon hit is received from a pre-boundary beacon or a non-pre-boundary beacon. For example, boundary agent 1774 demodulates the incoming IR signal from the first beacon to identify unique ID 1724 of the first beacon. Boundary agent 1774 uses unique ID 1724 to determine whether the first beacon is a pre-boundary beacon or a non-pre-boundary beacon. If, at step 2304, sensor 1606 determines that the first beacon hit is received from a non-pre-boundary beacon, step 2304 reverts to step 2302, while sensor 1606 waits for another beacon hit. Referring back to FIG. 2200, in this scenario, sensor wearer 2202 would be within range of at least one of beacon 1604A and beacon 1604B.

If, however, sensor 1606 determines that the first beacon is a pre-boundary beacon (e.g., beacons 1604C and/or 1604D), step 2304 proceeds to step 2308. At step 2308, sensor 1606 counts to a predetermined amount of time (e.g., four seconds). During this predetermined amount of time, sensor 1606 continues to scan for and receive beacon emissions. At step 2310, boundary agent 1774 determines whether sensor 1606 recorded a beacon hit within the predetermined amount of time.

If, at step 2310, boundary agent 1774 determines that sensor 1606 recorded a beacon hit within the predetermined amount of time, step 2310 proceeds to step 2312. At step 2312, boundary agent 1774 determines whether the beacon 1604 that registered the beacon hit is a pre-boundary beacon. For example, boundary agent 1774 demodulates the incoming IR signal from the first beacon to identify unique ID 1724 of the first beacon. Boundary agent 1774 uses unique ID 1724 to determine whether the first beacon is a pre-boundary beacon or a non-pre-boundary beacon.

If, at step 2312, boundary agent 1774 determines that the received beacon hit is from a non-pre-boundary beacon, then step 2312 reverts to step 2302. For example, sensor wearer 2202 moves from a location within range of at least one of beacon 1604C and beacon 1604D, to a new location that is only within range of at least one of beacon 1604A and beacon 1604B.

If, however, at step 2312, boundary agent 1774 determines that the received beacon hit is from a pre-boundary beacon, then step 2312 reverts to step 2308, and sensor 1606 counts to a predetermined amount of time (e.g., four seconds). For example, sensor wearer 2202 has remained in a location within range of at least one of beacon 1604C and beacon 1604D.

Referring back to step 2310, if sensor 1606 does not receive a beacon hit within the predetermined amount of time, step 2310 proceeds to step 2314. At step 2314, sensor 1606 actively scans the area for nearby beacons 1604. At step 2316, sensor 1606 determines whether any beacons 1604 are nearby. If at step 2316, sensor 1606 determines that there are not any beacons 1604 nearby, then method 2300 proceeds to step 2317 and sensor 1606 alerts management entity 1610.

If, however, sensor 1604 determines that there is a beacon 1604 nearby, then at step 2318 boundary agent 1774 determines whether the nearby beacon 1604 is a boundary beacon (e.g., 1604E and/or beacon 1604F). For example, boundary agent 1774 demodulates the incoming IR signal from the nearby beacon to identify unique ID 1724 of the nearby beacon. Boundary agent 1774 uses unique ID 1724 to determine whether the nearby beacon is a boundary beacon. If, at step 2318, boundary agent 1774 determines that the nearby beacon is not a boundary beacon, then step 2318 reverts to step 2302, and sensor 1606 waits for additional beacon emissions.

If, however, boundary agent 1774 determines that the nearby beacon is a boundary beacon (e.g., 1604E and/or beacon 1604F), then boundary agent 1774 initiates, at step 2320, an alert request to be transmitted to management entity 1610. For example, boundary agent 1774 communicates with processor 1764 for data packet generator 1778 to generate a data packet containing a boundary alert. Processor 1764 communicates with RF emitter 1756 to transmit the data packet containing the boundary alert to communication hub 1608. Communication hub 1608 acts as a gateway between sensor 1606 and management entity 1610. Thus, communication hub 1608 sends the information received from sensor 1606 to management entity 1610. In some embodiments, management entity 1610 may push notifications to client device(s) 1612 of staff in the facility to alert the staff that sensor wearer has entered a restricted area.

Figure 24:
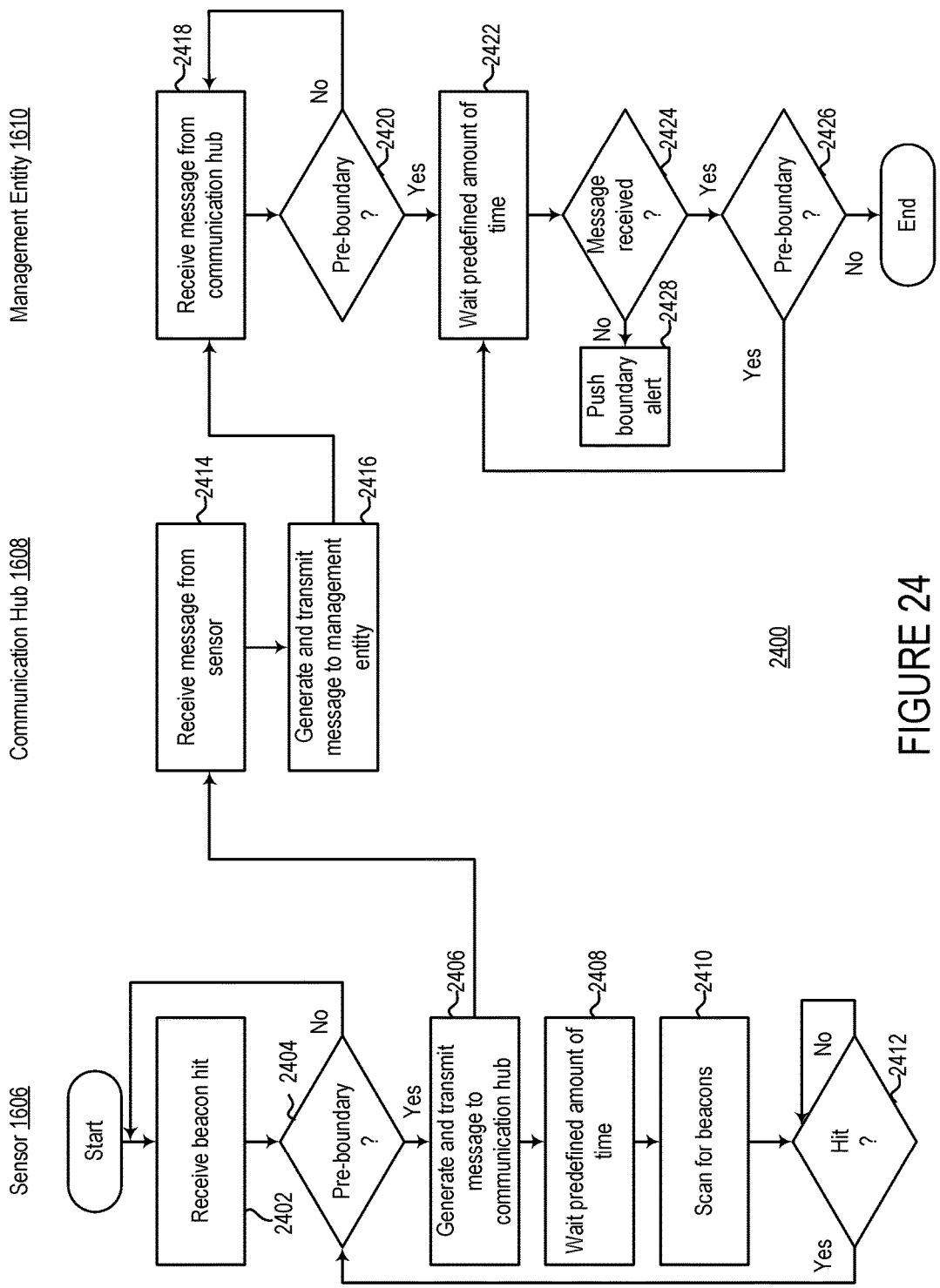
FIG. 24 is a flow chart illustrating an example method of detecting a location of a sensor wearer, according to one embodiment of the present disclosure.

FIG. 24 is a flow diagram of a method 2400 of locating a sensor wearer in a facility, according to one embodiment. Method 2400 begins at step 2402. At step 2402, sensor 1606 of the sensor wearer receives a hit from a first beacon. At step 2404, sensor 1606 determines whether the first beacon is a pre-boundary beacon. Sensor 1606 demodulates and parses the IR emission from the first beacon to classify the first beacon. For example, boundary agent 1774 demodulates the incoming IR signal from the first beacon to identify unique ID 1724 of the first beacon. Boundary agent 1774 uses unique ID 1724 to determine whether the first beacon is a pre-boundary beacon or a non-pre-boundary beacon. If at step 2404, boundary agent 1774 determines that the first beacon is not a pre-boundary beacon, step 2404 reverts to step 2402, and sensor 1606 waits for a subsequent beacon hit.

If, however, at step 2404, boundary agent 1774 determines that the first beacon is a pre-boundary beacon, then, at step 2406, sensor 1606 transmits the beacon hit to communication hub 1608. For example, responsive to boundary agent 1774 classifying the first beacon as a pre-boundary beacon, data packet generator 1778 generates a data packet that includes a pre-boundary alert to be transmitted to communication hub 1608. RF emitter 1756 transmits the generated data packet (i.e., a message) to communication hub 1608.

At step 2414, communication hub 1608 receives the generated data packet (i.e., the message) from sensor 1606. Communication hub 1608 sends the information received from sensor 1606 to management entity 1610 (step 2416).

At step 2418, management entity 1610 receives the information from communication hub 1608. At step 2420, management entity 1610 determines whether the beacon information received from communication hub 1608 is directed to a pre-boundary beacon. For example, management entity 1610 may include a local boundary agent 1780 (FIG. 17) that parses the information received from communication hub 1608 to determine a classification of the beacon. If, at step 2420, boundary agent 1780 determines that sensor 1606 received an emission from a non-pre-boundary beacon, then step 2420 reverts to step 2418, and management entity 1610 waits for additional information from communication hub 1608.

If, however, at step 2420, boundary agent 1780 determines that sensor 1606 received an emission from a pre-boundary beacon, then boundary agent 1780 begin a timer for a predetermined amount of time (e.g., 30 seconds) (step 2422). During this predetermined amount of time, management entity 1610 waits for additional information from communication hub 1608. Management entity 1610 determines whether a message is received within the predetermined amount of time (step 2424). If an additional message is not received from communication hub 1608 during the predetermined amount of time, then, at step 2428, boundary agent 1780 pushes a boundary alert to client device(s) 1612 of staff of the facility. In other words, if it has been about 30 seconds since management entity 1610 has received a location reading from sensor 1606, then management entity 1610 has deemed the sensor wearer to be out of the range of any beacon 1604, which corresponds to an area exterior of the boundary (e.g., Location 3 in FIG. 22).

If, however, at step 2424, management entity 1610 receives an additional message within the predetermined amount of time from communication hub 1608, management entity 1610 determines, at step 2426, whether the beacon information received from communication hub 1608 is directed to a pre-boundary beacon. For example, boundary agent 1780 parses the information received from communication hub 1608 to determine a classification of beacon 1604.

If at step 2426, boundary agent 1780 determines that the additional information is directed to an emission from a non-pre-boundary beacon, then method 2400 ends.

If, however, boundary agent 1780 determines that the additional information is directed to an emission from a pre-boundary beacon, then step 2426 reverts to step 2422, and boundary agent 1780 waits another predetermined amount of time for additional messages from communication hub 1608.

Referring back to step 2406, after sensor 1606 transmits the data packet to communication hub 1608, at step 2408, sensor 1606 waits a predetermined amount of time (e.g., about one second), and then, at step 2410, sensor 1606 actively scans the area for nearby beacons. At step 2412, sensor 1606 determines whether any beacons 1604 are nearby. If at step 2412, sensor 1606 finds a nearby beacon, step 2412 reverts to step 2404 for a classification of the beacon type (e.g., pre-boundary or non-pre-boundary). If, however, at step 2412, there is not a beacon nearby, step 2412 reverts to step 2410 for continued scanning of nearby beacons.

By continually scanning an area of the sensor wearer for nearby beacons 1604, in response to receiving a beacon hit from a pre-boundary beacon, sensor 1606 transmits periodic messages (e.g., every few seconds) to management entity 1610 with pre-boundary information. These periodic messages may be defined as "keep alive" messages. As the sensor wearer exits the facility, the link between sensor 1606 and communication hub 1608 will no longer be maintained. Thus, when management entity 1610 does not receive a message from sensor 1606 for an elongated period of time, management entity 1610 assumes that sensor wearer has left the facility, or at the very least, has entered an area exterior to the boundary. In some scenarios, a sensor wearer may approach the pre-boundary beacons, only to return back to a non-pre-boundary area. Thus, the additional check by management entity 1610 to classify a location of the sensor wearer breaks the countdown performed by the management entity 1610.

Figure 25:
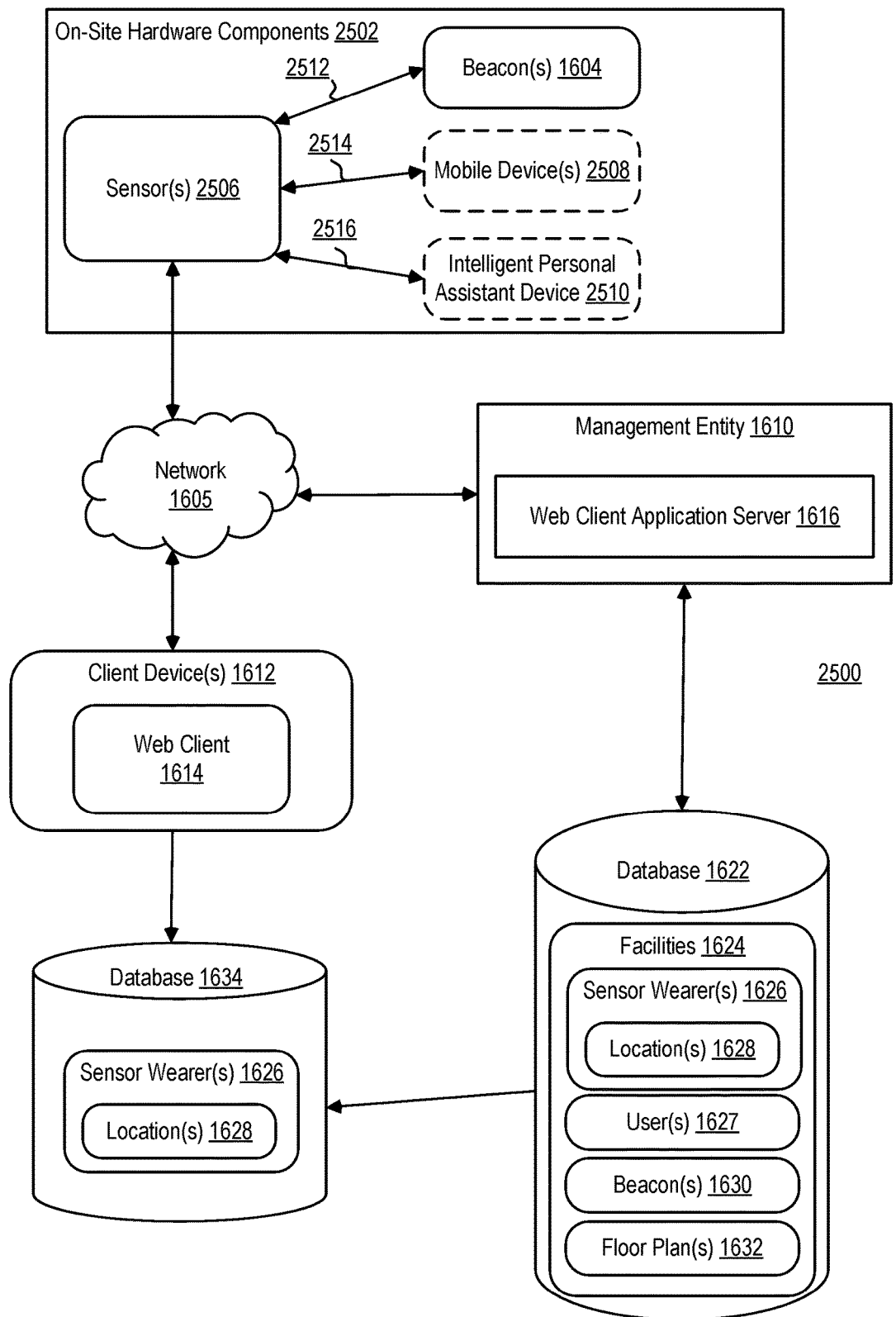
FIG. 25 is a block diagram of an example computing environment according to one embodiment of the present disclosure.

FIG. 25 illustrates a computing environment 2500, according to one embodiment. Computing environment 2500 may be used to practice one or more techniques disclosed herein. Computing environment 2500 is substantially similar to computing environment 1600. As illustrated, FIG. 25 includes similarly numbered elements where appropriate. Generally, computing environment 2500 operates similarly to that of computing environment 1600.

Computing environment 2500 differs from that of computing environment 1600 in that sensor 2506 obviates the need for any communication hubs 1608. As illustrated, computing environment 2500 includes on-site hardware components 2502 in place of on-site hardware components 1602. On-site hardware components 2502 may include at least one or more sensor(s) 2506 and the one or more beacon(s) 1604.

In some embodiments, on-site hardware components 2502 may further include one or more mobile device(s) 2508 of each sensor wearer and one or more intelligent personal assistant device(s) 2510.

For illustrative purposes, FIG. 25 illustrates a communication link 2512 between sensors 2506 and beacons 1604, a communication link 2514 between sensors 2506 and mobile devices 2508, and a communication link 1640 between sensors 2506 and intelligent personal assistant devices 2510.

Beacon(s) 1604 may be configured to be in communication with one or more sensors 2506. For example, beacon(s) 1604 may communicates with sensor(s) 2506 through the IR emissions emitted by beacon(s) 1604.

As discussed above, each sensor 2506 may be a wearable sensor apparatus. In one particular application, patients in an assisted living facility or a hospital may be equipped with sensor 2506 to track a location of the patient throughout the facility. Sensor 2506 may generally be positioned anywhere on a person's body, such that IR emissions can pass therethrough.

Figure 26:
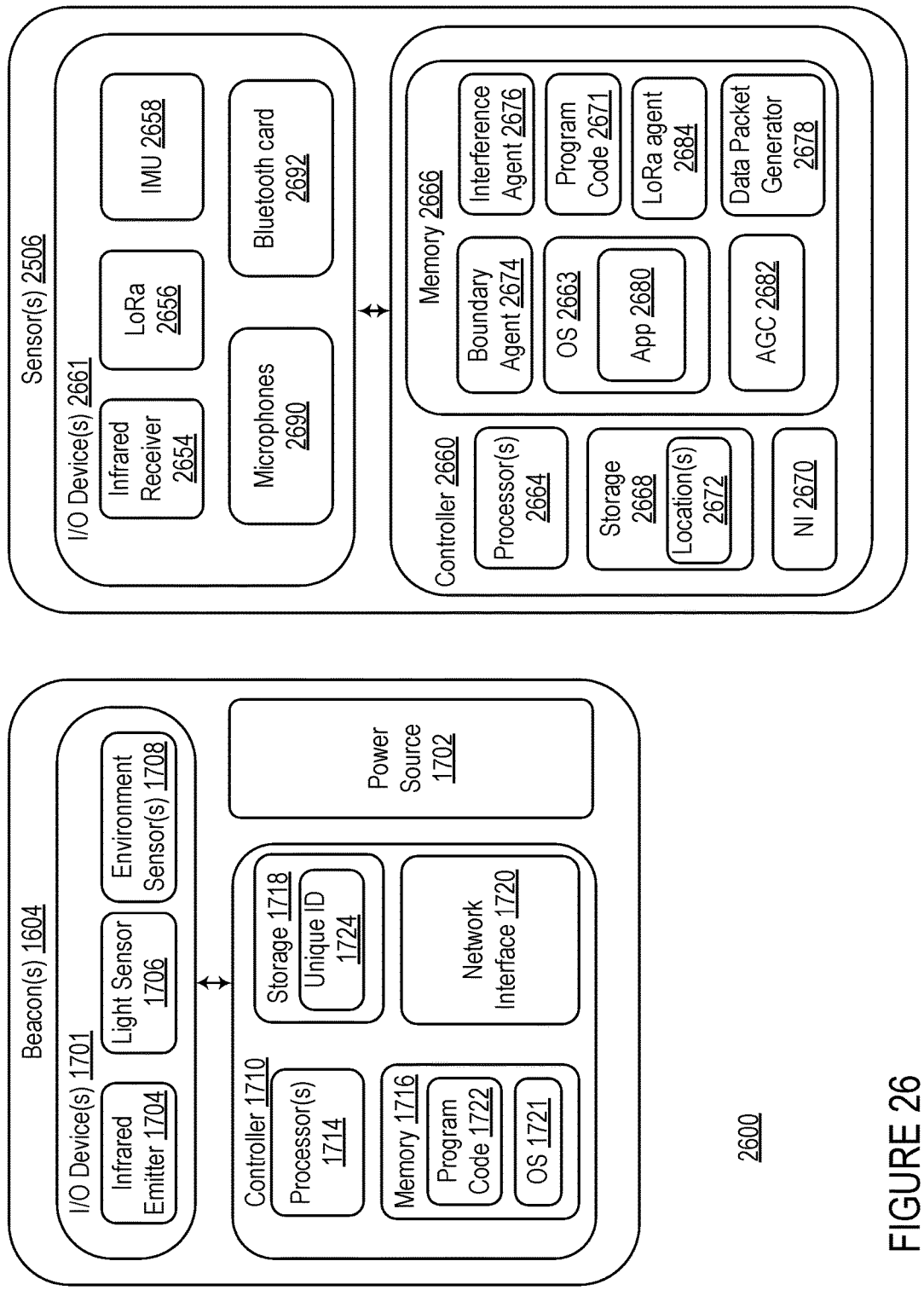
FIG. 26 is a block diagram illustrating a more detailed disclosure of example components in the computing environment of FIG. 25 according to one embodiment of the present disclosure.

FIG. 26 illustrates a single sensor 2506, according to one embodiment. Each sensor 2506 may include a controller 2660 and one or more I/O devices 2661.

Controller 2660 may include a processor 2664, a memory 2666, a storage 2668, and a network interface 2670. Controller 2660 is coupled to one or more I/O devices 2661.

Processor 2664 retrieves and executes programming code 2671 (i.e., programming instructions) stored in memory 2666, as well as stores and retrieves application data. Processor 2664 is included to be representative of a single processor, multiple processors, a single processor having multiple processing cores and the like. Network interface 2670 may be any type of network communications allowing controller 2660 to communicate externally via a computing network. For example, network interface 2670 enables wireless communication between sensor 2506 and management entity 1610 (discussed in more detail below). Further network interface 2670 enables sensor 2506 to perform two-way calling over network 1605. For example, network interface 2670 allows sensor 2506 to place and receive calls.

Storage 2668 may be, for example, a disk drive storage device. Although shown as a single unit, storage 2668 may be a combination of fixed and/or removable storage devices, such as fixed disk drives, removable memory cards, optical storage, NAS, or SAN. As illustrated, storage 2668 may include a location history 2672 (also referred to herein as list of locations 2672). Location history 2672 may include a list of all previous locations of sensor 2606, as well as a "latched history" of the last several locations of sensor 2606.

I/O devices 2661 may be in communication with controller 2660. I/O devices 2660 may include an infrared (IR) receiver 2654, a long-range radio transmitter (LoRa) 2656, an inertial measurement unit (IMU) 2658, one or more microphone(s) 2690, and a Bluetooth card 2692.

IR receiver 2654 is configured to receive IR emissions. For example, IR receiver 2654 may be configured to receive IR emissions from IR emitter 1704 of beacon 1604. Long-range radio transmitter 2656 is configured to transmit long-range radio signals.

Each microphone 2690 is configured to convert sound produced by the sensor wearer into a signal. For example, sensor 2506 may include dual microphones 2690 for use with voice applications. Two microphones 260 may allow for noise cancellation and beam forming. Noise cancellation may reduce ambient white noise and allow voice to be extracted more easily. Similarly, beam forming allows application 2680 to focus on extracting sound from the direction in-line with the source of the voice.

Sensor 2506 may provide the user with a natural voice interface leveraging the power of intelligent personal assistant devices 2510 (e.g., Amazon Alexa Voice Services, Microsoft Cortana, Google Assistant, Apple Siri). This allows sensor 2506 to have automatic speech recognition and natural language understanding. These features may be particularly useful to sensor wearers, as this is a more intuitive and natural way for sensor wearers to interact and ask questions.

Bluetooth card 2692 enables sensor 2506 to communicate with other devices (e.g., sensor wearer smartphones 2508 and intelligent personal assistant devices 2510) via Bluetooth. In other embodiments, Bluetooth connectivity may be useful when sensor 2506 leaves the facility, such that sensor 2506 is out of range of all beacons 1604, or any other communication hubs. In these scenarios, sensor 2506 may attempt to connect to a sensor wearer's mobile device 2508 via Bluetooth. In a particular example, Bluetooth card 2692 provides sensor 2506 with Bluetooth Low Energy (BLE) 4.0 and above connectivity. The advantage of BLE 4.0 and above protocols is that they do not require pairing of sensor 2506 with mobile device 2508. Therefore, sensor 2506 is able to connect onto a BLE universally unique identifier (UUID) of management entity 1610.

Once sensor 2506 is connected to mobile device 2508, sensor 2506 can authenticate and encrypt communication, thereby allowing sensor 2506 to tunnel all communication over BLE and communicate with management entity using a cellular network of mobile device 2508.

Memory 2666 may include programming code 2671, operating system (OS) 2673, boundary agent 2674, interference agent 2676, data packet generator 2678, long-range radio agent 2684, and automatic gain control (AGC) agent 2682. Program code 2671 may accessed by processor 2664 for processing (i.e., executing program instructions). Program code 2671 may include, for example, steps discussed in conjunction with FIGS. 18-24. In a specific example, processor 2664 accesses program code 2671 to demodulate and parse an IR emission received by IR receiver 2654.

Boundary agent 2674 may be configured to determine whether a wearer of sensor 2506 has entered, or is about to enter, a restricted area. Boundary agent 2674 is discussed further in conjunction with FIG. 24.

Interference agent 2676 may be configured to differentiate between a change in user location and interference, or intersection, between multiple IR emissions from multiple beacons 1604. Interference agent 2676 is discussed further in conjunction with FIGS. 19A, 19B, and 20.

Data packet generator 2678 may be configured to generate a data packet for transmission to management entity 1610, based on the modulated signal received from beacon 1604. For example, data packet generator 2678 may generate a data packet that includes unique ID 1724 of beacon 1604, location type, power level of beacon 1604, value(s) of one or more environmental sensors 1708, and pulse frequency. Sensor 2506 may transmit the data packet to management entity 1610, wirelessly, over network 1605 via network interface 2670.

Operating system 2663 includes application 2680, which allows a sensor wearer to access a functionality of management entity 1610. For example, application 2680 allows for interaction between sensor 2506 and management entity 1610. Thus, application 2680 is able to track a sensor wearer throughout a facility. For example, application 2680 allows access to functionality provided by, for example, CarePredict proprietary software.

Long-range agent 2684 works with long-range radio emitter 2656. In some examples, sensor 2506 may be unable to communicate with management entity 1610 due to a power loss in the building or other issues resulting a loss to the wireless communication between sensor 2506 and management entity 1610. Long-range agent 2684 works with long-range radio emitter 2656 to provide a back-up communication means in these situations. Long-range agent 2684 communicates with long-range radio emitter 2656 to transmit alerts to a locally installed battery backup, which is connected via a cellular network. This allows sensor 2506 to relay alerts in those situations where there is a network 1605 breakdown, by routing data over a cellular network.

The advantages of a back-up long-range protocol is that it can cover a large distance, as well as work in adverse indoor RF environments where the building structure is less transparent to RF frequencies. In one embodiment, long-range radio emitter 2656 uses a 900 Mhz band (although those skilled in the art could readily understand that different frequencies may be used). Long-range radio agent 2684 may use chirp modulation, which provides sensor 2506 with an increased ability to receive sensitivity, allowing it to communicate over larger distances.

In those situations where long-range radio agent 2684 is leveraged, hardware components 2502 further include a long-range radio base station 2509. Long-range radio base station 2509 may be a battery backed-up relay, which takes in alerts transmitted by long-range radio emitter 2656. A cellular modem may reside in long-range base station 2509. In one embodiment, cellular modem uses Narrowband— Internet of Things (NB-IoT) or Long Term Evolution— Category M1 (LTE-M) protocols. Additionally, long-range radio base station 2509 may further include a loudspeaker, allowing the base station 2509 to announce alerts.

AGC agent 2682 aids in controlling an output of sound for sensor 2506. For example, AGC agent allows a speaker of sensor 2506 to output a same level of sound, even if a person (remote from sensor) is talking very closely to sensor 2506 (or far away).

Although memory 2666 is shown as a single entity, memory 2666 may include one or more non-transitory memory devices having blocks of memory associated with physical addresses, such as RAM, ROM, flash memory, or other types of volatile and/or non-volatile memory.

Referring back to FIG. 25, sensor(s) 2506 may provide a gateway between on-site hardware components 2502 and an external system via network 1605. For example, computing environment 2500 may include management entity 1610, which may be in communication with on-site hardware components 1602 over network 1605 via sensor 2506.

Sensor 2506 may be used similarly as 1606 in the methods discussed above in conjunction with FIGS. 18-21 and 23-24. However, rather than sensor 2506 communicating with communication hub 1608 and then communication hub 1608 relaying the communication to management entity 1610, sensor 2506 communicates directly to management entity 1610. One having ordinary skill in the art could readily understand sensor 2506 executing the methods discussed in FIGS. 18-21 and 23-24.

Figure 27:
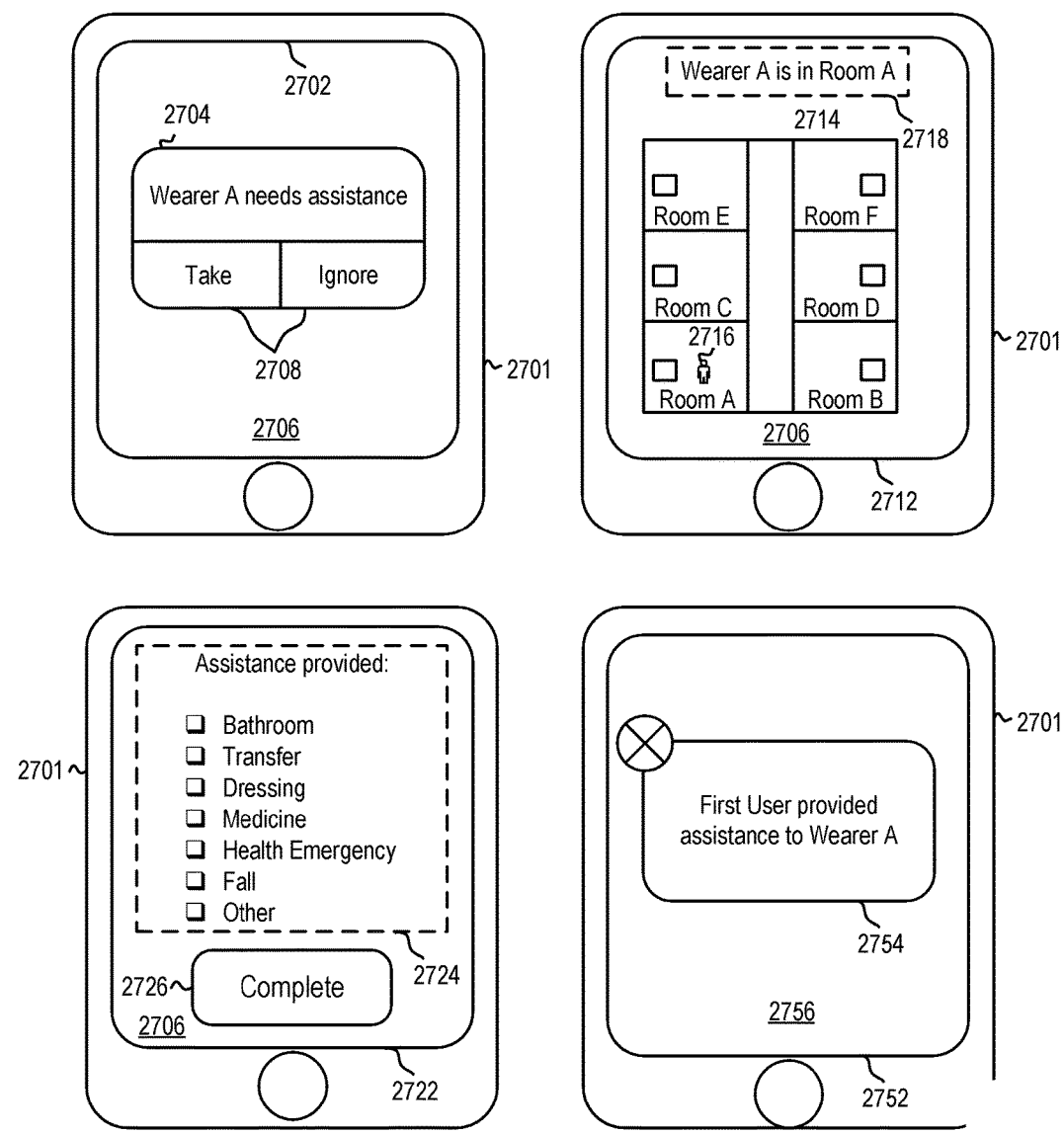
FIG. 27 is a block diagram of a series of screenshots of a client device, according to one embodiment of the present disclosure.

FIG. 27 illustrates a series of screenshots 2702, 2712, and 2722 of a first user's client device 2701 and second user's client device 2751, according to one embodiment. Client device 2701 and client device 2751 are examples of client device 1612 from FIGS. 16 and 25.

In operation, a sensor wearer (Wearer A) may provide an indication to management entity that sensor wearer needs assistance. In this scenario, management entity may generate a message to be pushed to client devices of staff in the facility of Wearer A. Client device 2701 and client device 2751 are example client devices of respective users, first user and second user. Screenshot 2702 illustrates a first screenshot of client device 2701. Screenshot 2702 illustrates a push notification 2704 on a screen 2706 of client device 2701. Push notification 2704 notifies the first user that Wearer A has requested assistance. Generally, each client device of each user in the facility with receive a push notification (e.g., push notification 2704) when a sensor wearer in the facility requests assistance. In this particular example, both client device 2701 and client device 2751 will receive the push notification. Push notification 2704 may provide first user with one or more response options 2708. As shown, one or more response options 2708 include "take" or "ignore." Take response option notifies each remaining client device (e.g., client device 2751) that first user has chosen to provide assistance to Wearer A. In this way, each user in the facility can be notified that assistance is to be provided to Wearer A.

Screenshot 2712 illustrates a second screenshot of client device 2701, responsive to the first user pressing "take," thereby choosing to assist Wearer A. Screenshot 2712 includes a floorplan 2714 of the facility. Floorplan 2714 illustrates a real-time location 2716 of Wearer A. For example, floorplan 2714 includes that last reported location of Wearer A's sensor. In some examples, floorplan 2714 may further include the last several reported locations of Wearer A, each location including a time-stamp. Real-time location 2716 allows the first user to quickly and more efficiently provide assistance to Wearer A. In some embodiments, management entity may further generate a message 2718 to be pushed to first user. For example, message 2718 may provide first user with a text-based location of Wearer A. In this example, message 2718 reads "Wearer A is in Room A."

Screenshot 2722 illustrates a third screenshot of client device 2701, after first user has provided assistance to Wearer A. Screenshot 2722 includes a list of options 2724. List of options 2724 includes a pre-generated list of possible actions first user undertook to provide assistance to Wearer A. For example list of options 2724 includes bathroom (bathroom assistance), transfer (assistance in transferring Wearer A in the facility), dressing (assistance in changing the clothes of Wearer A), medicine (assistance in providing medicine), health emergency, fall, or other. After assistance is provided to the user, first user may tap a box next to one or more of the items list of options 2724. After first user taps a respective one or more boxes, first user may press button 2726, which notifies management entity that assistance is complete.

Screenshot 2752 illustrates a first screenshot of client device 2751, after first user has notified management entity that assistance to Wearer A has been completed. Once management entity receives a completion notification, management entity generates a message to be pushed to each additional user in the facility that first user has completed assistance to Wearer A. For example, management entity transmits a message to client device 2751 to prompt client device 2751 to generate a push notification 2754 for display on a screen 2756 of client device 2751. Push notification 2754 alerts second user that "First User provided assistance to Wearer A."

Such system of alerting each user in the facility of when assistance is needed, who is requesting the assistance, who is providing the care, and when the assistance is complete, provides a more complete system for users and sensor wearers alike.

Figure 28:
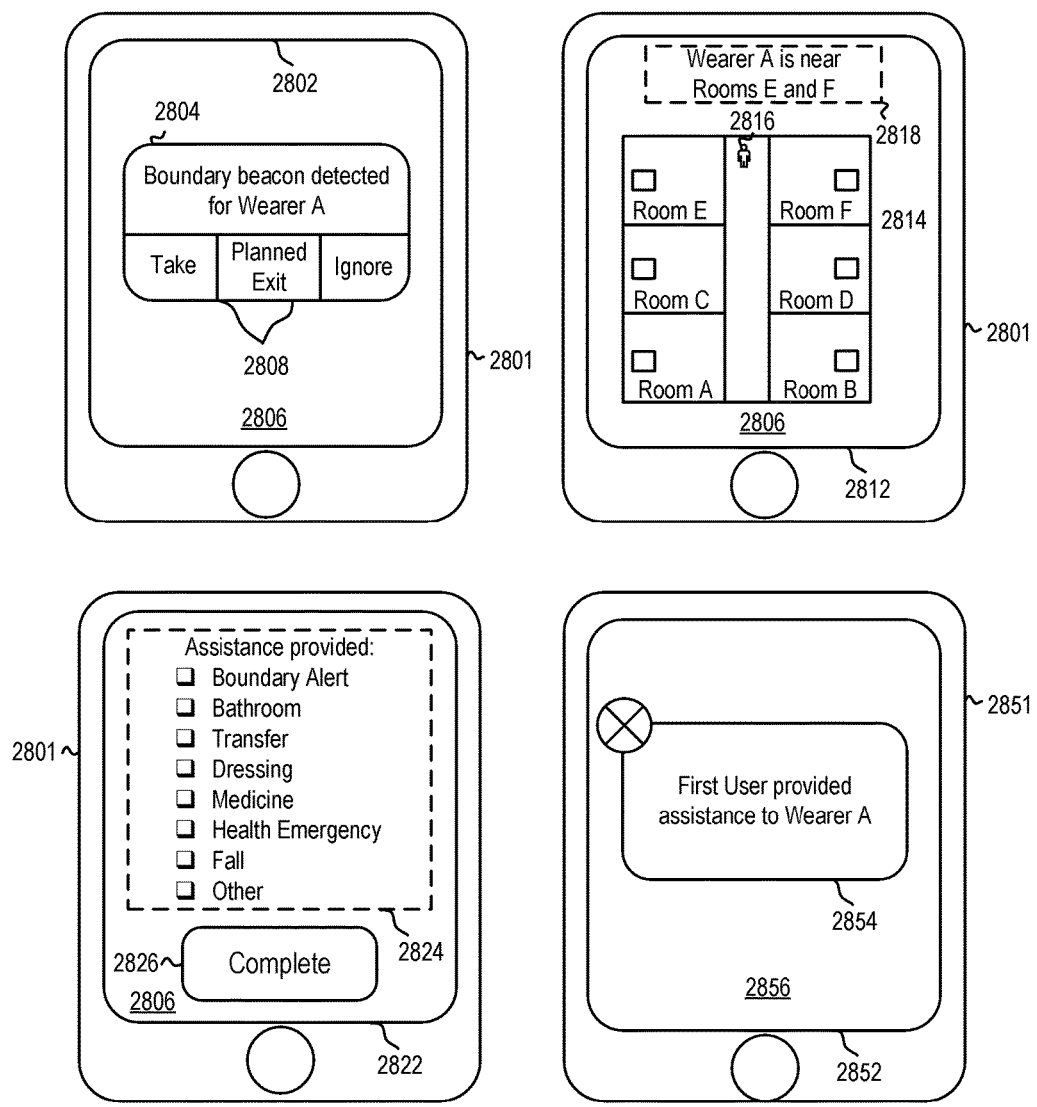
FIG. 28 is a block diagram of a series of screenshots of a client device, according to one embodiment of the present disclosure.

FIG. 28 illustrates a series of screenshots 2802, 2812, and 2822 of a first user's client device 2801 and second user's client device 2851, according to one embodiment. Client device 2801 and client device 2851 are examples of client device 1612 from FIGS. 16 and 25.

In operation, management entity 1610 may provide an indication to each client device in the facility that a sensor wearer has received a beacon hit from a pre-boundary or boundary beacon, and that assistance is needed for that specific sensor wearer. In this scenario, management entity may generate a message to be pushed to client devices of staff in the facility of Wearer A. Client device 2801 and client device 2851 are example client devices of respective users, first user and second user. Screenshot 2802 illustrates a first screenshot of client device 2801. Screenshot 2802 illustrates a push notification 2804 on a screen 2804 of client device 2801. Push notification 2804 notifies the first user that assistance is needed regarding Sensor A. For example, push notification 2804 may recite "Boundary beacon detected for Wearer A." Generally, each client device of each user in the facility will receive a push notification (e.g., push notification 2804) when management entity 1610 identifies that a sensor wearer has reached a pre-boundary or boundary beacon. In this particular example, both client device 2801 and client device 2851 will receive the push notification. Push notification 2804 may provide first user with one or more response options 2808. As shown, one or more response options 2808 include "take," "ignore," or "planned exit." Take response option notifies each remaining client device (e.g., client device 2851) that first user has chosen to provide assistance to Wearer A. In this way, each user in the facility can be notified that assistance is to be provided to Wearer A. Planned exit option notifies each remaining client device (e.g., client device 2851) that Wearer A, for example, has notified first user ahead of time of a planned exit from the facility, and that a response to the notification is not needed.

Screenshot 2812 illustrates a second screenshot of client device 2801, responsive to the first user pressing "take," thereby choosing to assist Wearer A. Screenshot 2812 includes a floorplan 2814 of the facility. Floorplan 2814 illustrates a real-time location 2816 of Wearer A. For example, floorplan 2814 includes that last reported location of Wearer A's sensor. In some examples, floorplan 2814 may further include the last several reported locations of Wearer A, each location including a time-stamp. Real-time location 2816 allows the first user to quickly and more efficiently provide assistance to Wearer A. In some embodiments, management entity may further generate a message 2818 to be pushed to first user. For example, message 2818 may provide first user with a text-based location of Wearer A. In this example, message 2718 reads "Wearer A is near Rooms E and F."

Screenshot 2822 illustrates a third screenshot of client device 2801, after first user has provided assistance to Wearer A. Screenshot 2822 includes a list of options 2824. List of options 2824 includes a pre-generated list of possible actions first user undertook to provide assistance to Wearer A. For example list of options 2824 includes boundary alert, bathroom (bathroom assistance), transfer (assistance in transferring Wearer A in the facility), dressing (assistance in changing the clothes of Wearer A), medicine (assistance in providing medicine), health emergency, fall, or other. After assistance is provided to the user, first user may tap a box next to one or more of the items list of options 2824. After first user taps a respective one or more boxes, first user may press button 2826, which notifies management entity that assistance is complete.

Screenshot 2852 illustrates a first screenshot of client device 2851, after first user has notified management entity that assistance to Wearer A has been completed. Once management entity receives a completion notification, management entity generates a message to be pushed to each additional user in the facility that first user has completed assistance to Wearer A. For example, management entity transmits a message to client device 2851 to prompt client device 2851 to generate a push notification 2854 for display on a screen 2856 of client device 2851. Push notification 2784 alerts second user that "First User provided assistance to Wearer A."

Such system of alerting each user in the facility of when assistance is needed, who is requesting the assistance, who is providing the care, and when the assistance is complete, provides a more complete system for users and sensor wearers alike.

While the foregoing discussion presents the teachings in an exemplary fashion with respect to the disclosed methods and systems for remotely determining levels of healthcare interventions, it will be apparent to those skilled in the art that the present disclosure may apply to any type of method and system for monitoring a patient for healthcare purposes. Further, while the foregoing has described what are considered to be the best mode and/or other examples, it is understood that various modifications may be made therein and that the subject matter disclosed herein may be implemented in various forms and examples, and that the method(s) and system(s) may be applied in numerous applications, only some of which have been described herein.

What is claimed:

1. A system for locating an individual within a space, comprising:
   a beacon positioned in a location of the space, the beacon comprising:
      an infrared emitter; and
      a first processor, the first processor in communication with the infrared emitter, the first processor configured to instruct the infrared emitter to periodically emit an infrared emission, wherein the first processor modulates the infrared emission with a unique identification of the beacon that corresponds to the location of the beacon; and
a sensor worn by a sensor wearer, the sensor comprising:
an infrared receiver;
a second processor in communication with the infrared receiver; and
a memory having programming instructions stored thereon, which, when executed by the second processor, performs an operation, comprising:
receiving, in the sensor, an infrared emission emitted by the beacon proximate the sensor wearer;
demodulating the infrared emission to extract the unique identification of the infrared sensor;
determining whether the beacon that emitted the infrared emission is in a list of recent locations; and
responsive to determining that the beacon is not in the list of recent locations,
reporting to a remote management entity, the location of the sensor wearer and current time based on information received in the infrared emission.

2. The system of claim 1, wherein the beacon further comprises:
a light sensor configured to measure a level of ambient light about the beacon; and
one or more environmental sensor configured to measure one or more environmental levels about the beacon,
wherein the first processor further modulates the infrared emission based on the level of ambient light and the one or more environmental levels.

3. The system of claim 1, wherein the beacon further comprises:
a power source, wherein the first processor further modulates the infrared emission based on a level of the power source.

4. The system of claim 1, further comprising:
a further beacon positioned within a further location of the space.

5. The system of claim 4, wherein the sensor comprises:
an interference agent configured to filter simultaneous emissions from the beacon and the further beacon.

6. The system of claim 1, wherein the sensor comprises:
a boundary agent configured to generate an alert message responsive to determining that infrared emission was emitted by a beacon in a restricted area.

7. The system of claim 1, further comprising:
a management entity remote from the space, wherein the management entity is in communication with the sensor.

8. The system of claim 1, further comprising:
a user device of the sensor wearer, wherein the user device of the sensor wearer is in selective communication with the sensor.

9. The system of claim 8, wherein the sensor wearer communicates with the user device, responsive to the sensor no longer sensing the beacon.

10. The system of claim 8, wherein the user device is in communication with a management entity that receives infrared emission information from the sensor.

11. The system of claim 1, wherein the sensor further comprises:
a long-range radio agent in communication with a long-range radio emitter.

12. The system of claim 1, further comprises:
an intelligent personal assistance device.

13. The system of claim 12, wherein the sensor further comprises:
one or more microphone devices allowing communication between the sensor and the intelligent personal assistance device.

14. The system of claim 1, wherein the operation further comprises:
receiving a further infrared emission emitted by a further beacon proximate the sensor wearer;
determining whether the further beacon that emitted the infrared emission is in the list of recent locations;
responsive to determining that the further beacon is in the list of recent locations, determining whether a predetermined period of time has elapsed since receiving a prior infrared emission from the further beacon; and
responsive to determining that the predetermined period of time has elapsed since receiving the prior infrared emission from the further beacon,
reporting to a remote management entity, a further location of the sensor wearer and further time based on information received in the further infrared emission.

15. The system of claim 1, wherein the operation further comprises:
receiving a further infrared emission emitted by a further beacon proximate the sensor wearer;
determining whether the further beacon that emitted the infrared emission is in the list of recent locations;
responsive to determining that the further beacon is in the list of recent locations, determining whether the further beacon is the same as a most recently recorded beacon; and
responsive to determining that the further beacon is not the same as a most recently recorded beacon, filtering the further infrared emission.

16. The system of claim 1, wherein the operation further comprises:
receiving a further infrared emission emitted by a further beacon proximate the sensor wearer;
determining whether the further beacon that emitted the infrared emission is in the list of recent locations;
responsive to determining that the further beacon is in the list of recent locations, determining whether the further beacon is the same as a most recently recorded beacon;
responsive to determining that the further beacon is the same as a most recently recorded beacon, determining whether there are a predetermined amount of consecutive infrared emissions received from the further beacon; and
responsive to determining that the consecutive infrared emissions received from the further beacon exceeds the predetermined amount,
reporting to a remote management entity, a further location of the sensor wearer and further time based on information received in the further infrared emission.

17. The system of claim 1, wherein the operation further comprises:
receiving a further infrared emission emitted by a further beacon proximate the sensor wearer;
determining whether the further beacon that emitted the infrared emission is in the list of recent locations;
responsive to determining that the further beacon is in the list of recent locations, determining whether the further beacon is the same as a most recently recorded beacon;
responsive to determining that the further beacon is the same as a most recently recorded beacon, determining whether there are a predetermined amount of consecutive infrared emissions received from the further beacon;

responsive to determining that the consecutive infrared emissions received from the further beacon does not exceed the predetermined amount, filtering the further infrared emission.

18. The system of claim 1, wherein receiving, in a sensor positioned on the sensor wearer, an infrared emission emitted by a beacon proximate the sensor wearer, comprises:

determining whether the sensor is in motion; and responsive to determining that the sensor is in motion, enabling an infrared receiver of the sensor to receive infrared emissions.

19. The system of claim 1, wherein the operation further comprises:

receiving a further infrared emission emitted by a further beacon proximate the sensor wearer;

determining whether the further beacon that emitted the infrared emission is in the list of recent locations;

responsive to determining that the further beacon is not a last reported beacon;

examining a history of the further beacon to determine whether a predetermined amount of time has elapsed since last seeing the further beacon;

responsive to determining that the predetermined amount of time has elapsed, clearing the list of recent locations.

20. The system of claim 19, wherein the operation further comprises:

receiving another infrared emission emitted by the further beacon;

determining that the further beacon is not in the list of recent locations; and reporting to a remote management entity, a further location of the sensor wearer based on information received in the further infrared emission.

* * * * *